(12) United States Patent
Hwang et al.

(10) Patent No.: US 8,247,090 B2
(45) Date of Patent: Aug. 21, 2012

(54) HETEROCYCLIC COMPOUND AND ORGANIC ELECTROLUMINESCENT DEVICE COMPRISING THE SAME

(75) Inventors: Seok-Hwan Hwang, Yongin (KR); Young-Kook Kim, Yongin (KR); Yoon-Hyun Kwak, Yongin (KR); Jeoung-In Yi, Yongin (KR); Il-Soo Oh, Yonngin (KR)

(73) Assignee: Samsung Mobile Display Co., Ltd. (KR)

( * ) Notice: Subject to any disclaimer, the term of this patent is extended or adjusted under 35 U.S.C. 154(b) by 460 days.

(21) Appl. No.: 12/536,287

(22) Filed: Aug. 5, 2009

(65) Prior Publication Data

US 2010/0033088 A1    Feb. 11, 2010

(30) Foreign Application Priority Data

Aug. 7, 2008  (KR) .................... 10-2008-0077548

(51) Int. Cl.
*H01L 51/54* (2006.01)
*C09K 11/06* (2006.01)
*C07D 209/04* (2006.01)

(52) U.S. Cl. ........ 428/690; 428/917; 313/504; 313/506; 257/E51.05; 548/440; 548/469

(58) Field of Classification Search .................. None
See application file for complete search history.

(56) References Cited

U.S. PATENT DOCUMENTS

| | | | |
|---|---|---|---|
| 2001/0023029 A1 | 9/2001 | Shi et al. | |
| 2001/0033944 A1* | 10/2001 | Onikubo et al. | 428/690 |
| 2002/0028346 A1 | 3/2002 | Shi et al. | |
| 2004/0013903 A1* | 1/2004 | Lin | 428/690 |
| 2007/0057250 A1* | 3/2007 | Takiguchi et al. | 257/40 |

* cited by examiner

*Primary Examiner* — Marie R. Yamnitzky

(74) *Attorney, Agent, or Firm* — Knobbe Martens Olson & Bear LLP

(57) ABSTRACT

Provided are a heterocyclic compound represented by Formula 1 below and an organic electroluminescent device including an organic layer comprising the heterocyclic compound:

Formula 1

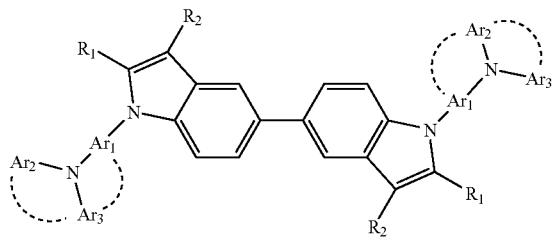

wherein $Ar_1$, $Ar_2$, $Ar_3$, $R_1$, and $R_2$ are the same as defined in the detailed description. The heterocyclic compound represented by Formula 1 has excellent electrical characteristics and an excellent charge transporting capability, and thus the heterocyclic compound of Formula 1 can be used as a hole injecting material, a hole transporting material, and/or a light emitting material that are suitable for all-color fluorescent and phosphorescent organic light emitting devices such as red, green, blue, and white fluorescent and phosphorescent organic light emitting devices. In addition, the organic electroluminescent device including an organic layer comprising the heterocyclic compound represented by Formula 1 can have a high efficiency, a low driving voltage, and high luminosity.

21 Claims, 1 Drawing Sheet

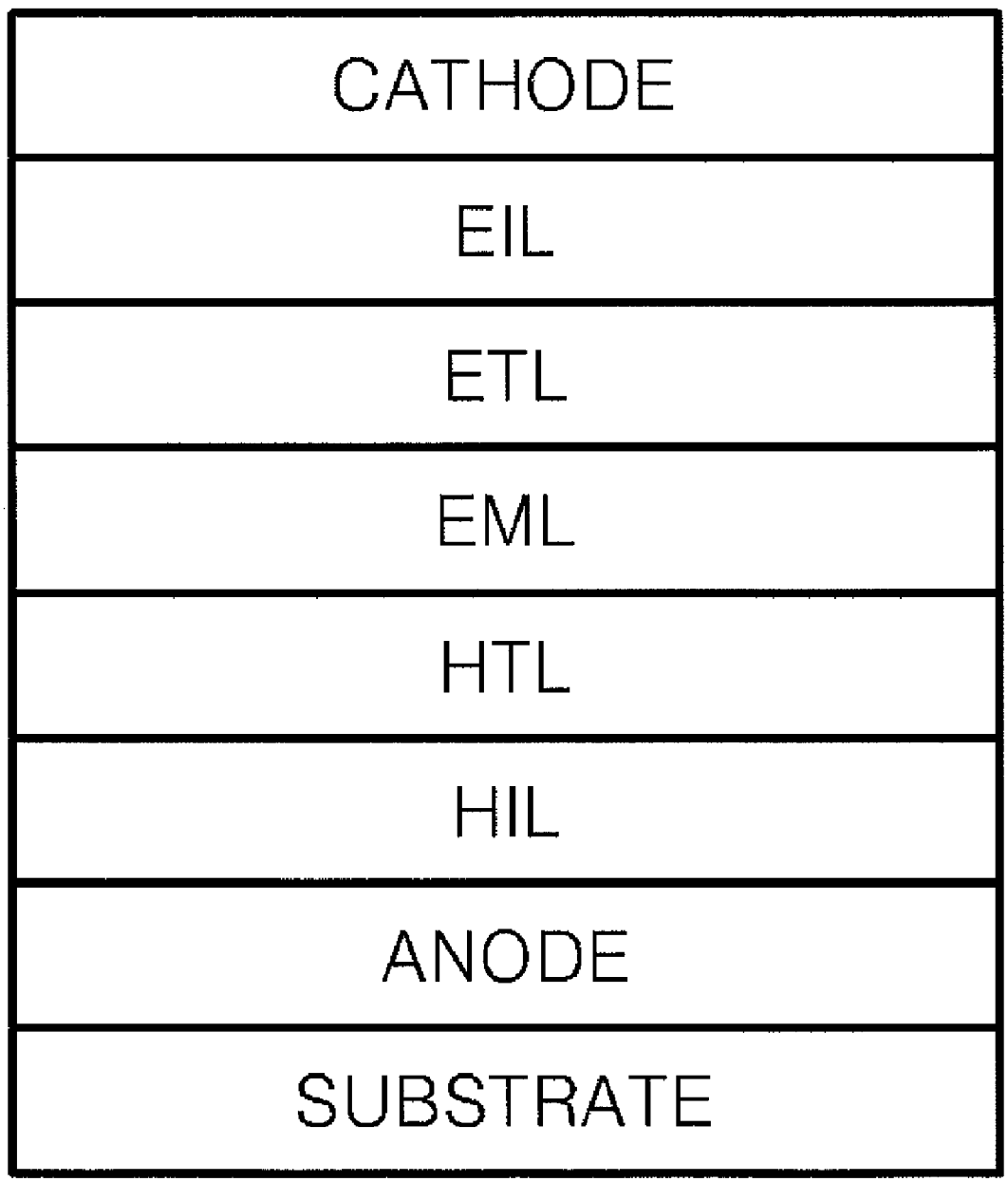

HETEROCYCLIC COMPOUND AND ORGANIC ELECTROLUMINESCENT DEVICE COMPRISING THE SAME

CROSS-REFERENCE TO RELATED PATENT APPLICATION

This application claims the benefit of Korean Patent Application No. 10-2008-0077548, filed on Aug. 7, 2008, in the Korean Intellectual Property Office, the disclosure of which is incorporated herein in its entirety by reference.

BACKGROUND

1. Field

The present embodiments relate to a heterocyclic compound and an organic electroluminescent device comprising the same, and more particularly, to a heterocyclic compound having a high electrical stability, a high charge transporting capability, a high glass transition temperature, and a crystallization preventing capability, and an organic electroluminescent device including an organic layer comprising the same.

2. Description of the Related Art

Electroluminescent devices are a self-emission type display device and have a wide viewing angle, a high contrast ratio, and a short response time. Due to such characteristics, electroluminescent devices are getting more attention. Electroluminescent devices are generally classified into inorganic electroluminescent devices including an emitting layer employing an inorganic compound and organic electroluminescent devices including an emitting layer employing an organic compound. Specifically, organic electroluminescent devices have higher luminescent characteristics, a lower driving voltage, and a shorter response speed than inorganic electroluminescent devices. In addition, organic electroluminescent devices produce various colors. Due to those characteristics, much research into organic electroluminescent devices is being performed. In general, an organic electroluminescent device has a stack structure of anode/organic emitting layer/cathode, or when a hole injection layer and/or a hole transport layer and/or an electron injection layer are further stacked between the anode and the emitting layer or between the emitting layer and the cathode, a stack structure of anode/hole transport layer/organic emitting layer/cathode or a stack structure of anode/hole transport layer/organic emitting layer/electron transport layer/cathode.

Meanwhile, a polyphenyl compound or anthracene derivatives are well known as a hole transport layer forming material (see U.S. Pat. No. 6,596,415 and U.S. Pat. No. 6,465,115). However, organic electroluminescent devices employing conventional hole injection layer and/or hole transport layer forming materials still needs to be improved in terms of lifetime, efficiency, and power consumption.

SUMMARY

The present embodiments provide a heterocyclic compound having a high electrical stability, a high charge transporting capability, a high glass transition temperature, and a crystallization preventing capability, which is used as an organic layer forming material that is suitable for use in all-color fluorescent and phosphorescent organic light emitting devices such as red, green, blue, and white fluorescent and phosphorescent organic light emitting devices.

The present embodiments also provide an organic electroluminescent device including an organic layer comprising the heterocyclic compound, thereby having high efficiency, a low driving voltage, and high luminosity, and a flat panel display device including the organic electroluminescent device.

According to an aspect of the present embodiments, there is provided a heterocyclic compound represented by Formula 1 below:

Formula 1

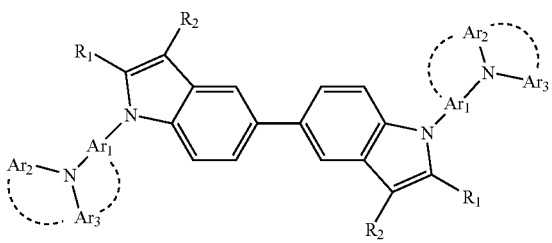

wherein $Ar_1$, $Ar_2$, and $Ar_3$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group, $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group, and $Ar_1$ and $Ar_3$ or $Ar_2$ and $Ar_3$ may be bound to each other to form a ring.

According to another aspect of the present embodiments, there is provided an organic electroluminescent device comprising: a first electrode; a second electrode; and an organic layer interposed between the first electrode and the second electrode, wherein the organic layer comprises the heterocyclic compound described above.

The organic layer may be a hole injection layer, a hole transport layer, or an emitting layer.

The organic layer may be an emitting layer, and the heterocyclic compound represented by Formula 1 may be used as a fluorescent or phosphorescent host.

BRIEF DESCRIPTION OF THE DRAWINGS

The above and other features and advantages of the present embodiments will become more apparent by describing in detail exemplary embodiments thereof with reference to the attached drawing in which:

FIG. 1 is a diagram illustrating a structure of an organic light emitting device according to an embodiment.

DETAILED DESCRIPTION

One embodiment provides a heterocyclic compound represented by Formula 1 below that is a symmetrical heterocyclic compound in which two indole groups are linked to each other at the center of a molecule through the $C_5$ position of the indole group, wherein the heterocyclic compound may be used as an organic layer forming material of an organic electroluminescent device, Formula 1

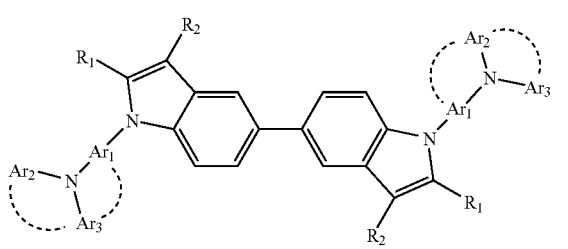

wherein $Ar_1$, $Ar_2$, and $Ar_3$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group, and wherein $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group.

In Formula 1, if $Ar_1$, $Ar_2$, $Ar_3$, $R_1$, or $R_2$ is an aryl group, heterocyclic group, or condensed polycyclic group that is substituted with a substituent having at least 21 carbon atoms, the resultant heterocyclic compound of Formula 1 has a very large molecular weight, and thus it is difficult to deposit the compound. Therefore, the aryl compound, the heterocyclic group, or the condensed polycyclic group may be substituted with a substituent having 20 or less carbon atoms.

The heterocyclic compound of Formula 1 can be used as a hole injecting material, a hole transporting material, and/or a light emitting material. In addition, the heterocyclic compound of Formula 1 has at least two indole groups therein, thus having a high glass transition temperature (Tg) or a high melting point. Accordingly, when electroluminescence occurs, the heterocyclic compound of Formula 1 has high heat resistance to Joule heat occurring in an organic layer, between organic layers, or between an organic layer and a metallic electrode and high durability in high-temperature environment. An organic electroluminescent device manufactured using the heterocyclic compound of Formula 1 according to an embodiment has high durability during storage and operation.

In the heterocyclic compound of Formula 1, $Ar_1$, $Ar_2$, and $Ar_3$ may be each independently a substituted or unsubstituted $C_6$-$C_{20}$ aryl group or a substituted or unsubstituted $C_4$-$C_{20}$ heteroaryl group, wherein, if these organic groups are introduced as $Ar_1$, the groups are bivalent connecting groups.

Examples of $Ar_1$, $Ar_2$, and $Ar_3$ include a phenyl group, an ethylphenyl group, a methylbiphenyl group, an ethylbiphenyl group, an o-, m-, or p-fluorophenyl group, a chlorophenyl group, a cyanophenyl group, a trifluorophenyl group, a methoxyphenyl group, an o-, m-, or p-tolyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, a naphthyl group, a methylnaphthyl group, an anthracenyl group, a phenanthrenyl group, a pyrenyl group, an azrenyl group, a heptarenyl group, an acenaphthylenyl group, a fluorenyl group, an anthraquinolyl group, a phenanthryl group, a triphenylene group, a pentaphenyl group, a hexaphenyl group, and a carbazolyl group.

$Ar_1$, $Ar_2$, and $Ar_3$ are each independently 1 to 4 cyclic aromatic ring selected from a phenyl group, a naphthyl group, an anthryl group, a phenanthryl group, a pyrenyl group, a biphenyl group, a terphenyl group, a fluorenyl group, and a carbazolyl group, or these aromatic rings substituted with 1 to 3 substituents selected from the group consisting of a $C_1$-$C_4$ alkyl group, a $C_1$-$C_5$ alkoxy group, a cyano group, an amine group, a phenoxy group, a phenyl group, and a halogen atom.

In the heterocyclic compound of Formula 1, $Ar_1$ and $Ar_3$ or $Ar_2$ and $Ar_3$ may be bound to each other to form a ring. When $Ar_1$ and $Ar_3$ or $Ar_2$ and $Ar_3$ are bound to each other to form a ring, any one of $Ar_1$ and $Ar_3$ and $Ar_2$ and $Ar_3$ may form a carbazolyl group.

$R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group.

$R_1$ and $R_2$ may be each independently hydrogen, methyl, phenyl, naphthyl, biphenyl, fluorophenyl, cyanophenyl, or methylphenyl.

The unsubstituted alkyl group used herein may be methyl, ethyl, propyl, isobutyl, sec-butyl, pentyl, iso-amyl, hexyl, or the like. In those alkyl groups, at least one hydrogen atom may be substituted with a halogen atom, a hydroxyl group, a nitro group, a cyano group, an amino group, an amidino group, hydrazine, hydrazone, a carboxyl group or salt thereof, a sulfuric acid or salt thereof, a phosphoric acid or salt thereof, a $C_1$-$C_{10}$ alkyl group, a $C_1$-$C_{10}$ alkenyl group, a $C_1$-$C_{10}$ alkynyl group, a $C_6$-$C_{10}$ aryl group, a $C_7$-$C_{10}$ arylalkyl group, a $C_2$-$C_{10}$ heteroaryl group, or a $C_3$-$C_{10}$ heteroarylalkyl group.

The unsubstituted alkoxy group used herein may be methoxy, ethoxy, phenyloxy, cyclohexyloxy, naphthyloxy, isopropyloxy, diphenyloxy, or the like. At least one hydrogen atom of the alkoxy group may be substituted with the same substituents as those recited in the above definition of the alkyl group.

The unsubstituted aryl group used herein may be used alone or in combination, and refers to an aromatic carbocyclic system containing at least one rings. The rings may be attached to each other or fused with each other using a pendant method. At least one hydrogen atom of the aryl group may be substituted with the same substituents as those recited in the above definition of the alkyl group.

Examples of the unsubstituted aryloxy group used herein include phenyloxy, naphthyleneoxy, and diphenyloxy. At least one hydrogen atom of the aryloxy group may be substituted with the same substituents as those recited in the above definition of the alkyl group.

The unsubstituted heterocyclic group used herein refers to a monovalent monocyclic or bicyclic aromatic bivalent organic compound which contains 1, 2 or 3 hetero atoms selected from the group consisting of N, O, P, and S and has 4 to 30 carbon atoms. At least one hydrogen atom of the heterocyclic group may be substituted with the same substituents as those recited in the above definition of the alkyl group.

Examples of the heterocyclic group include a pyrazolyl group, an imidazolyl group, an oxazolyl group, a thiazolyl group, a triazolyl group, a tetrazolyl group, an oxadiazolyl group, a pyridinyl group, a pyridazinyl, a pyrimidinyl group, a triazinyl group, a carbazolyl group, and an indolyl group.

Examples of the heterocyclic compound represented by Formula 1 may include Compounds 1 through 144 represented by the following structural formulae. However, the heterocyclic compound of Formula 1 is not limited thereto.
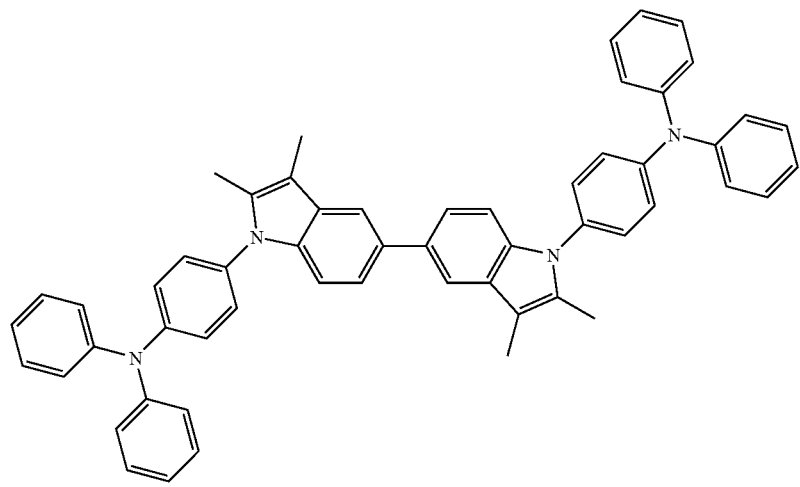
1
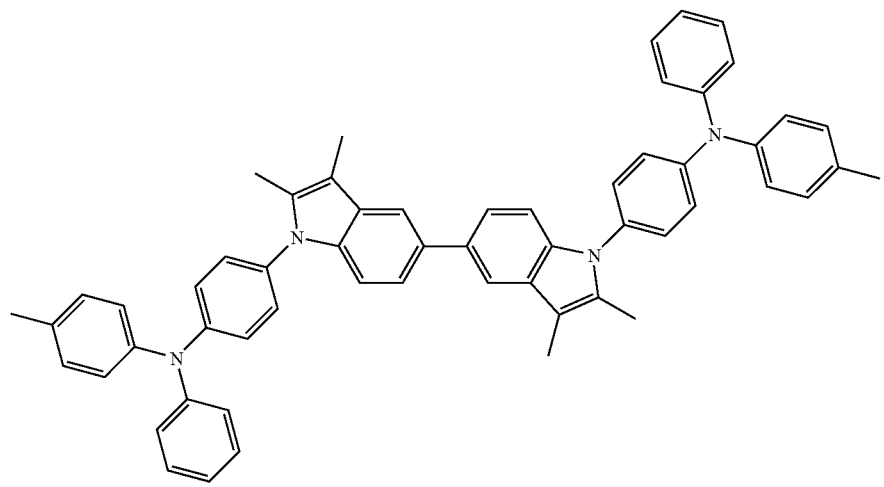
2
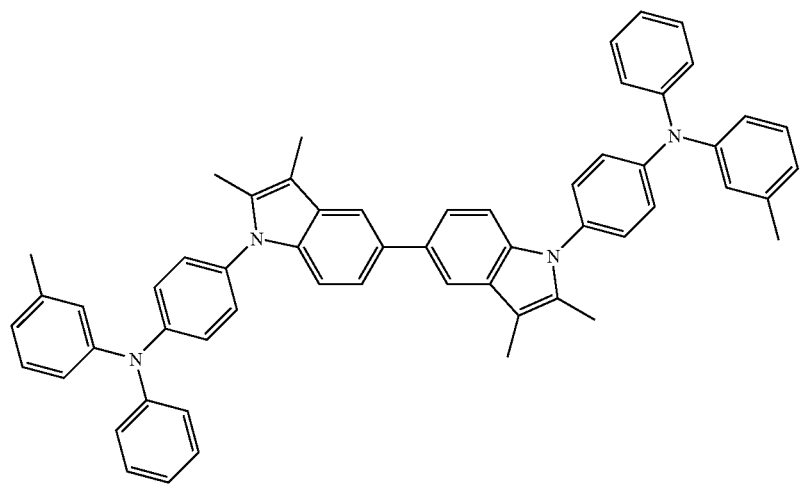
3

-continued
4
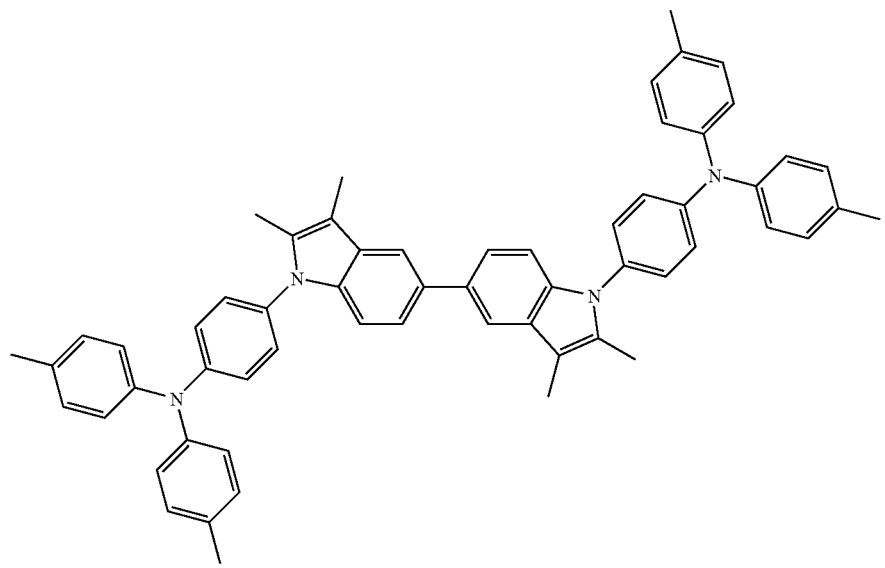
5
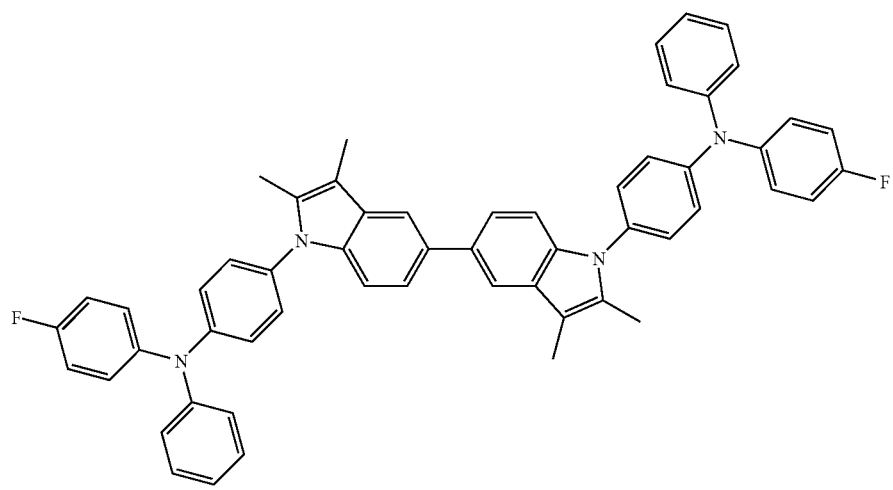
6
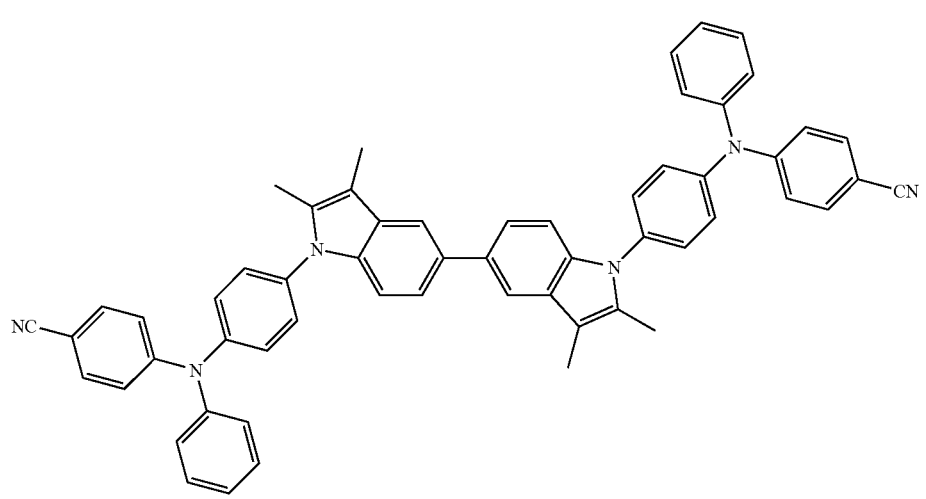

-continued
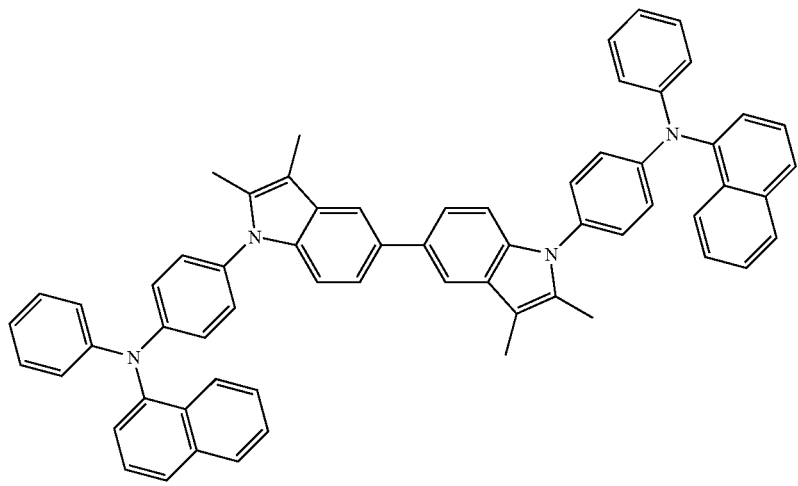
7
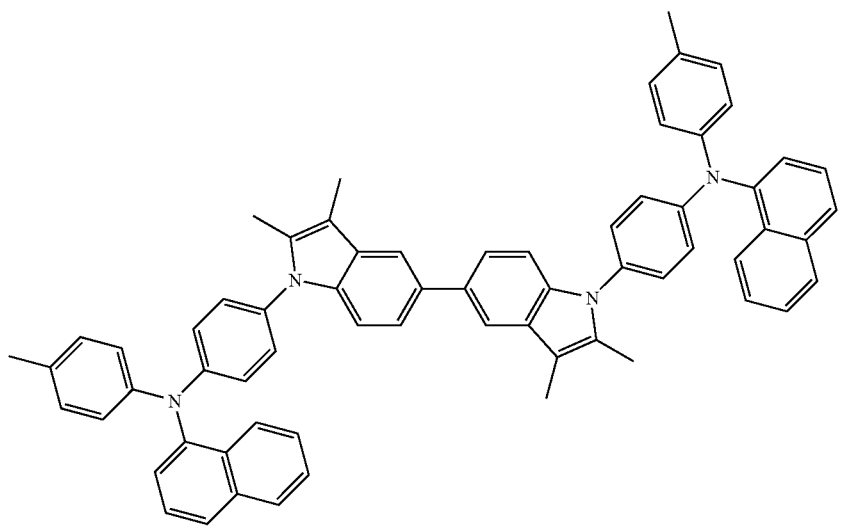
8
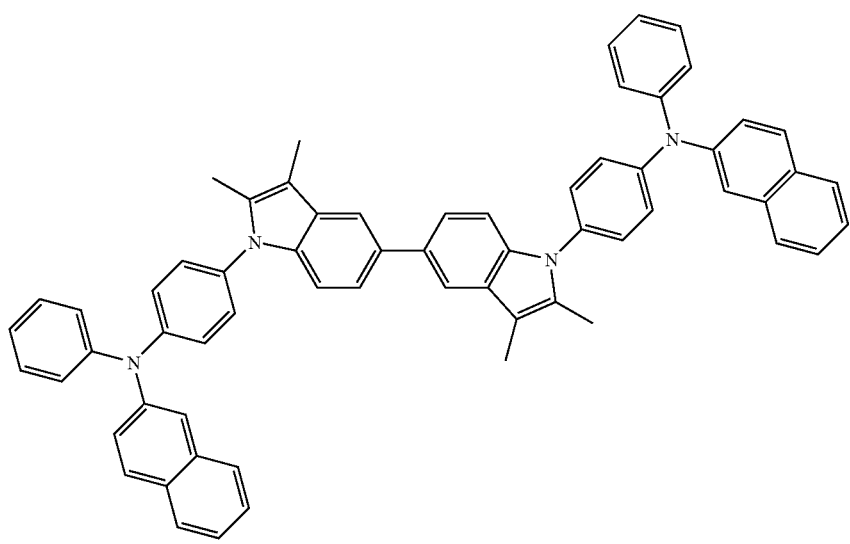
9

-continued
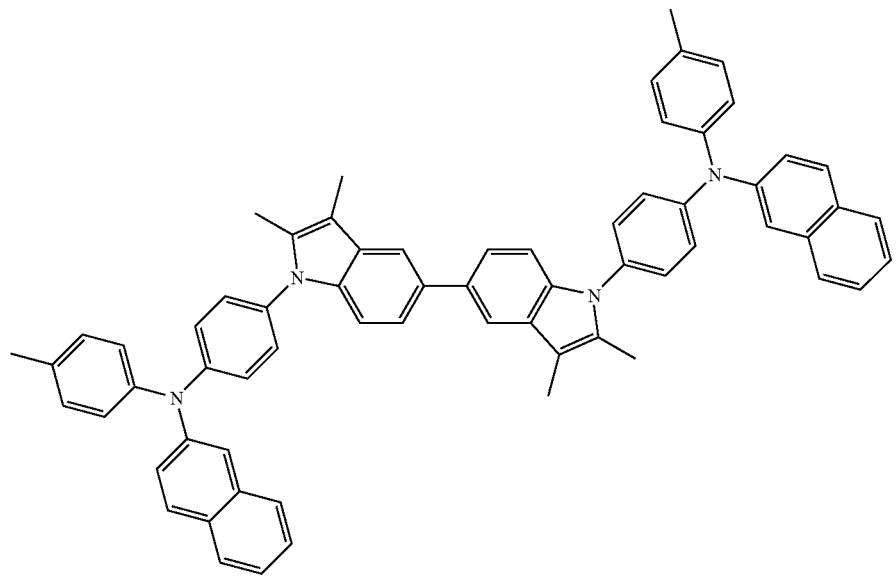
10
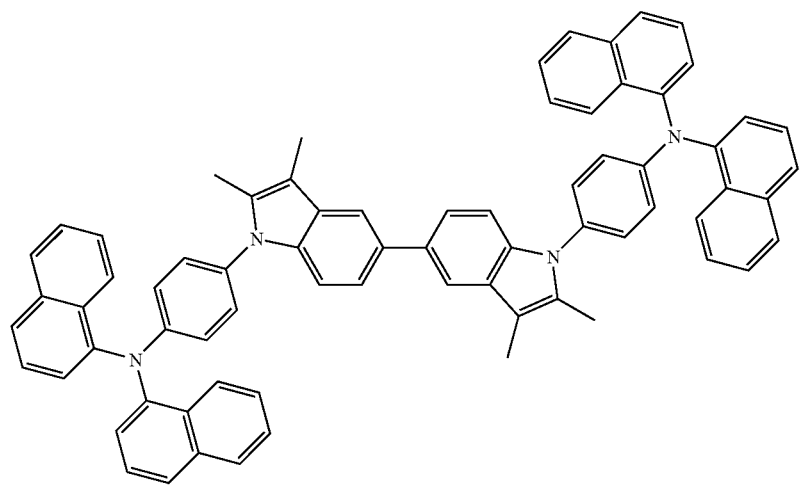
11

-continued
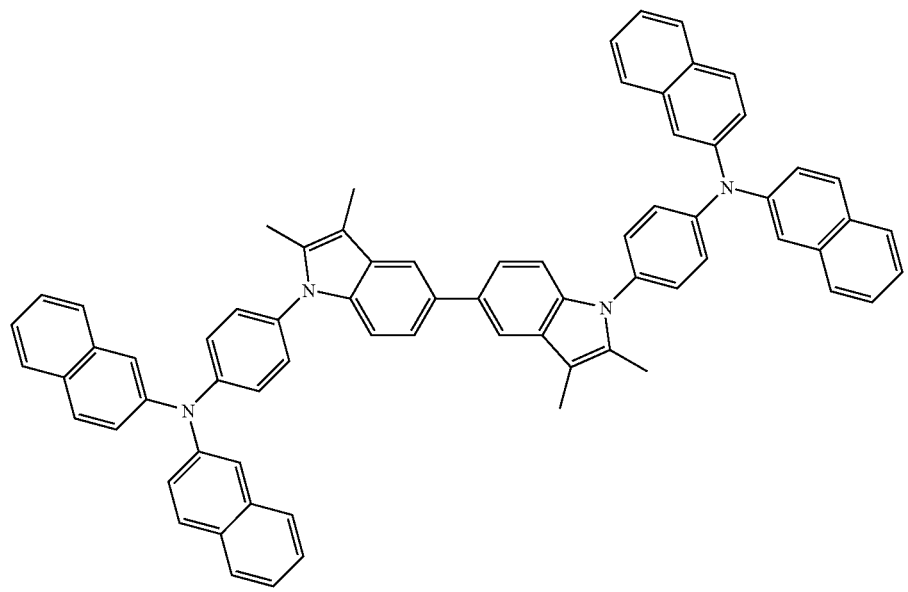
12
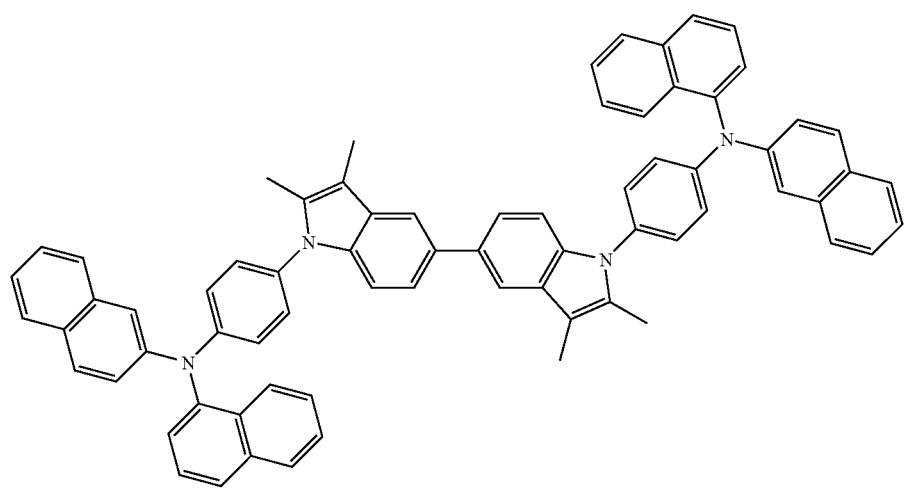
13
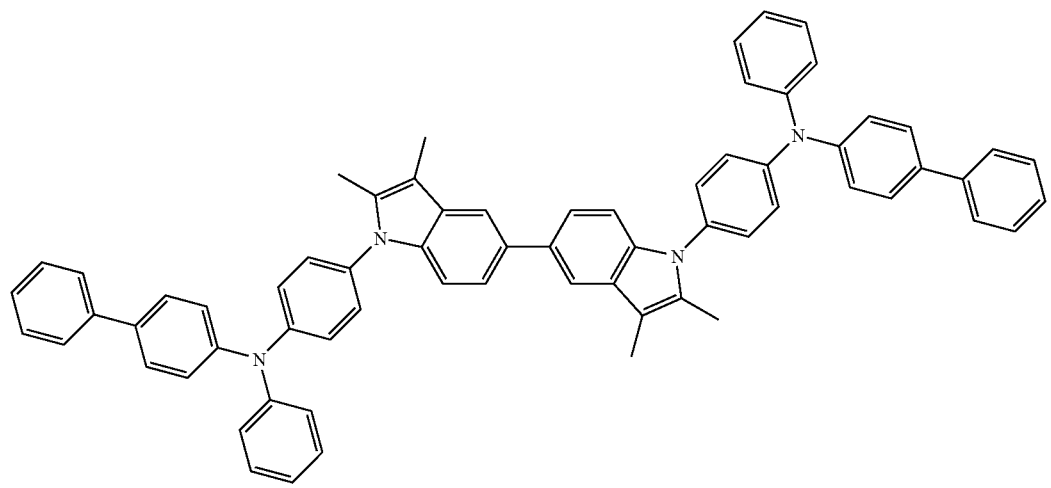
14

-continued
15
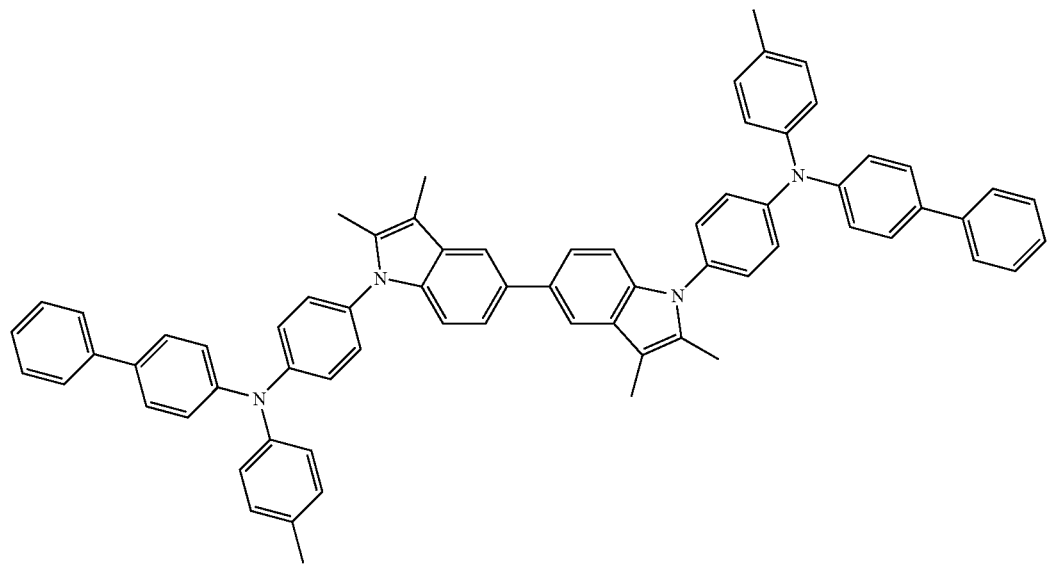
16
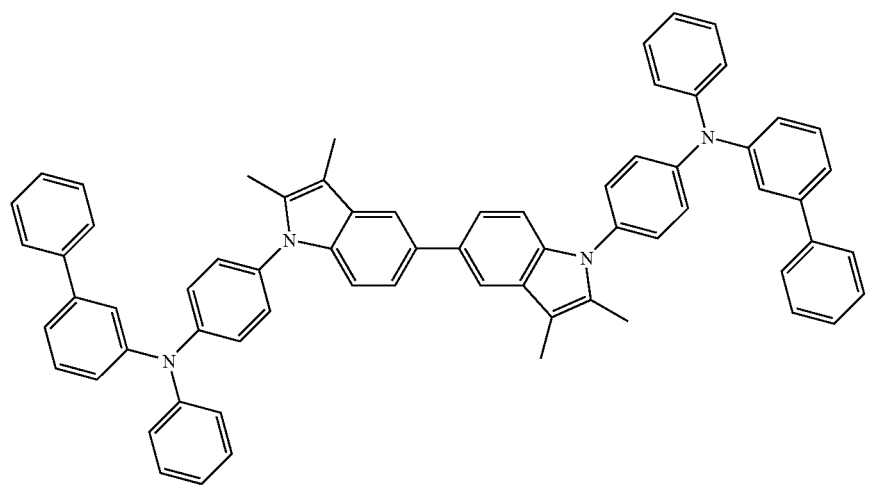
17
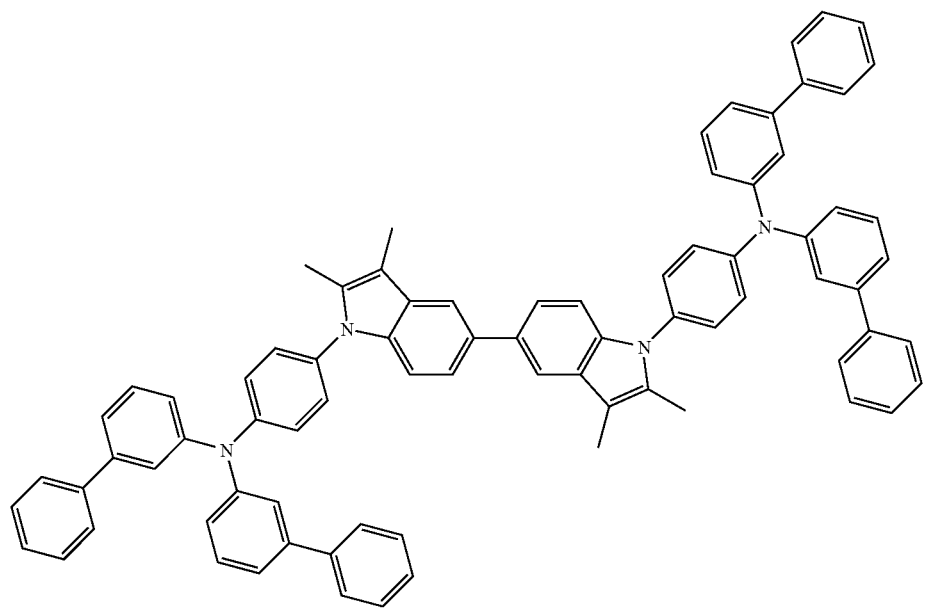

-continued
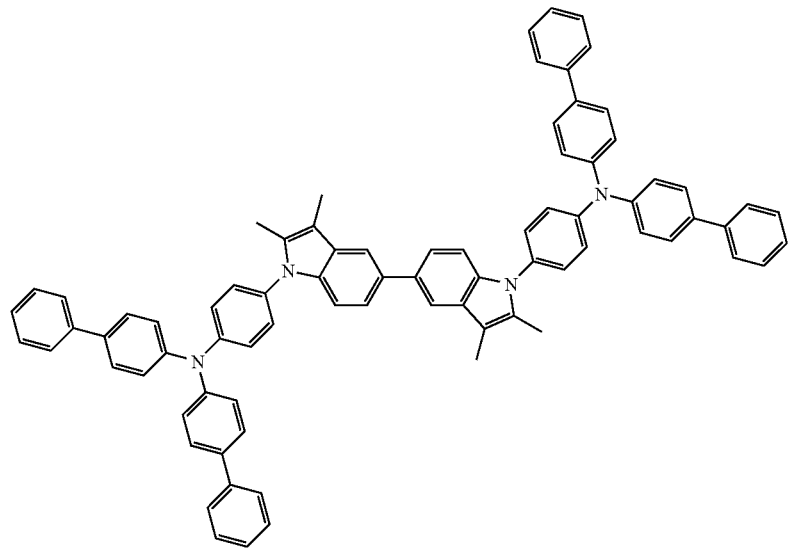
18
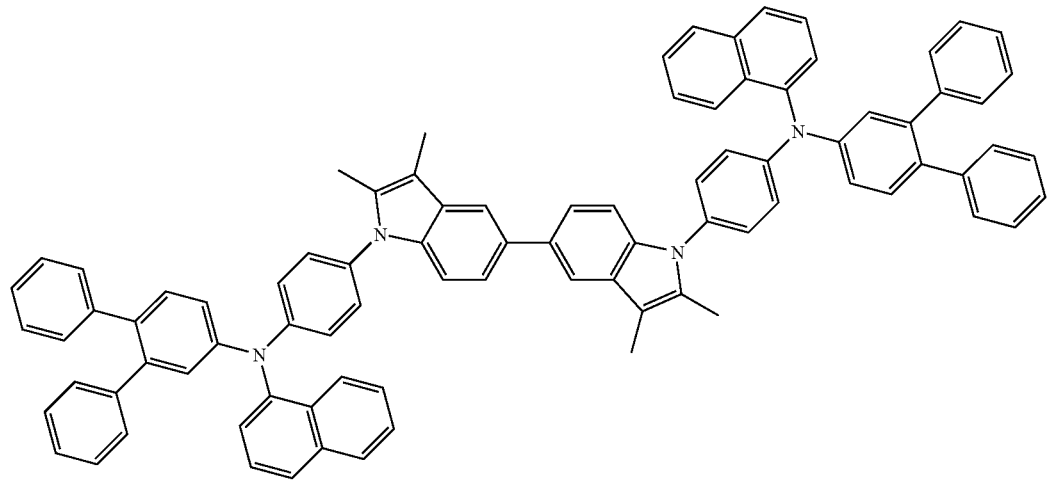
19
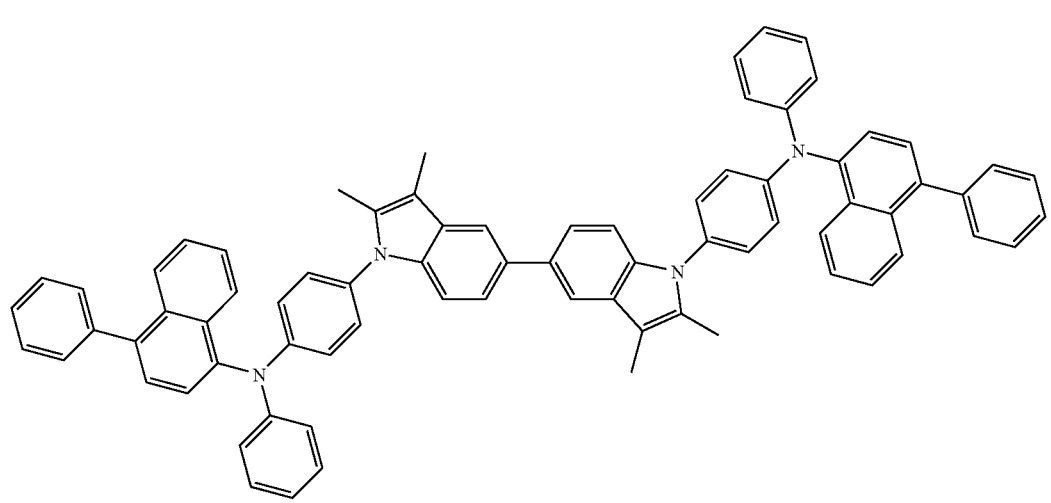
20

-continued
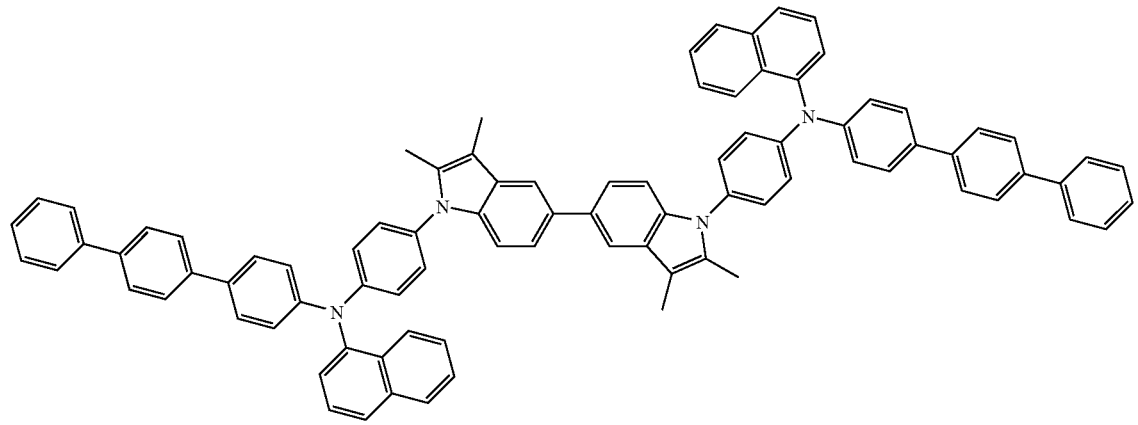
21
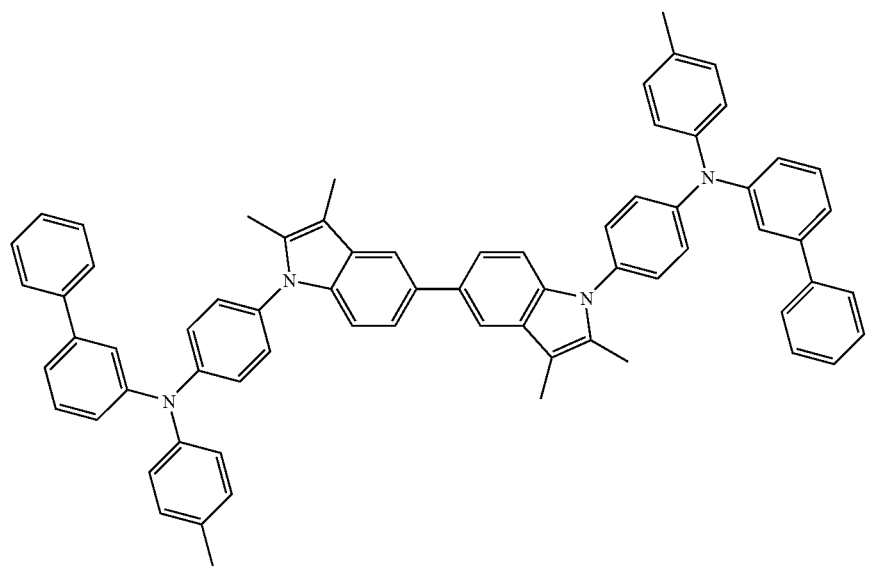
22
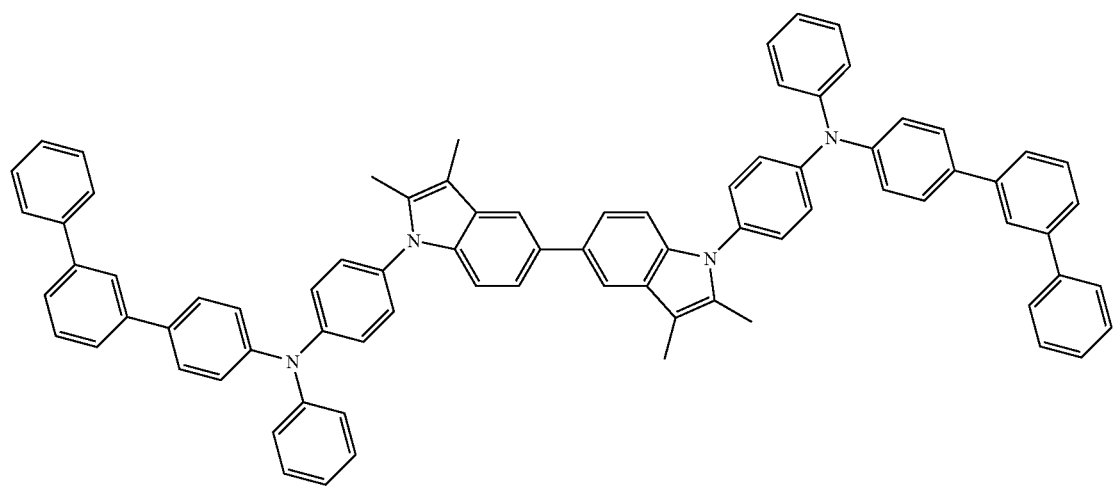
23

24
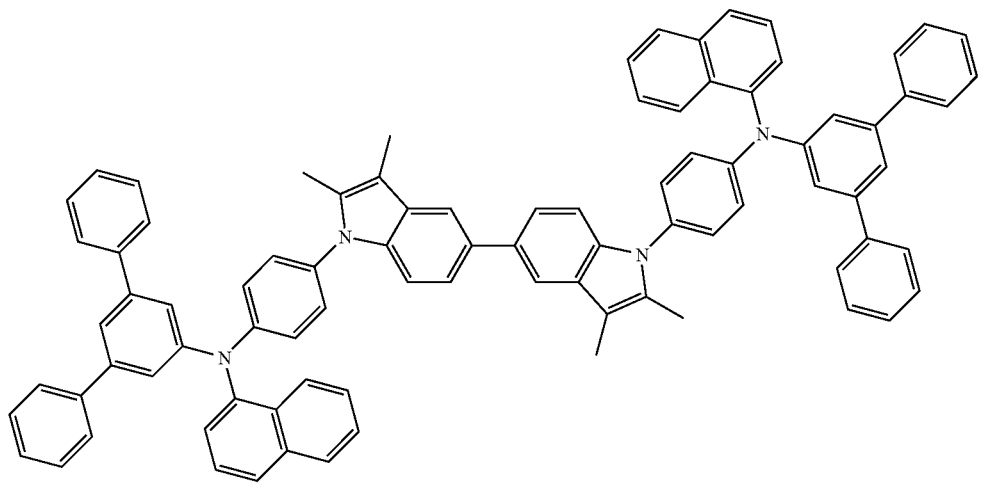
25
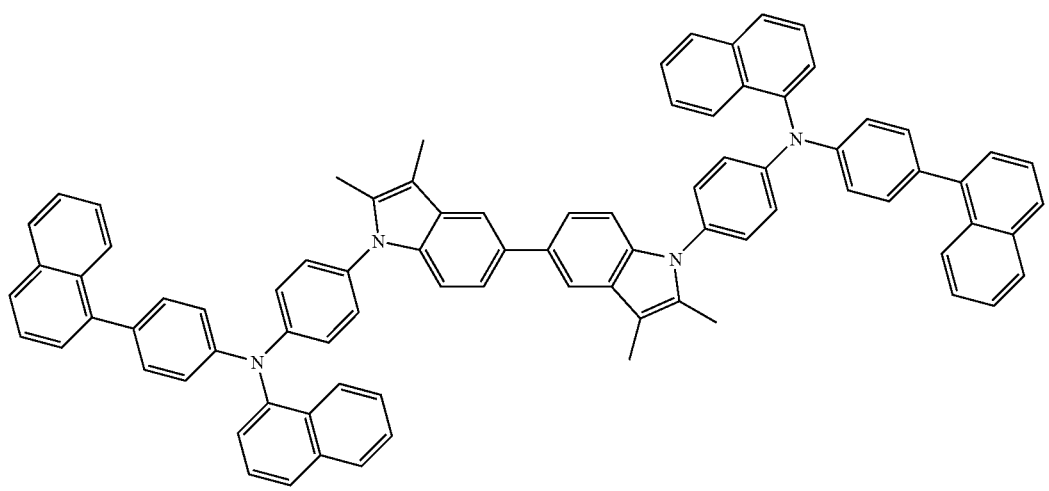
26
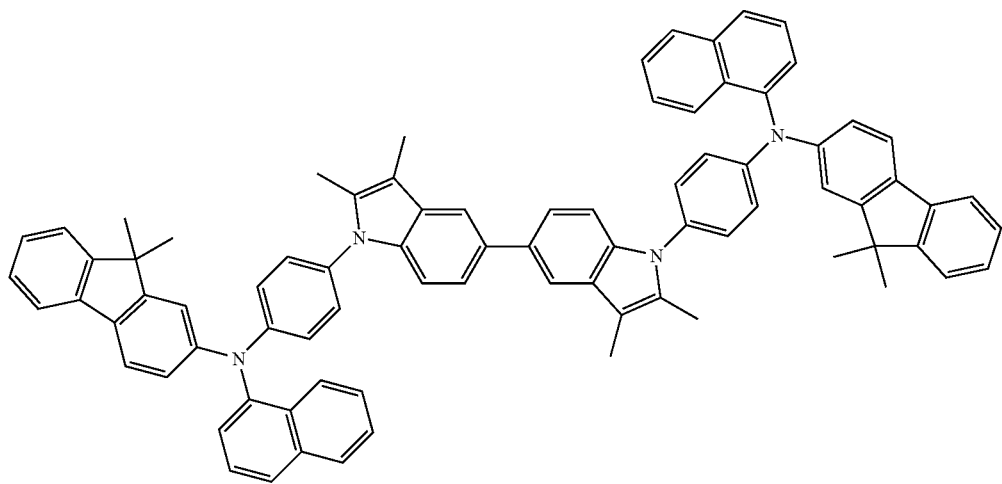

-continued
27
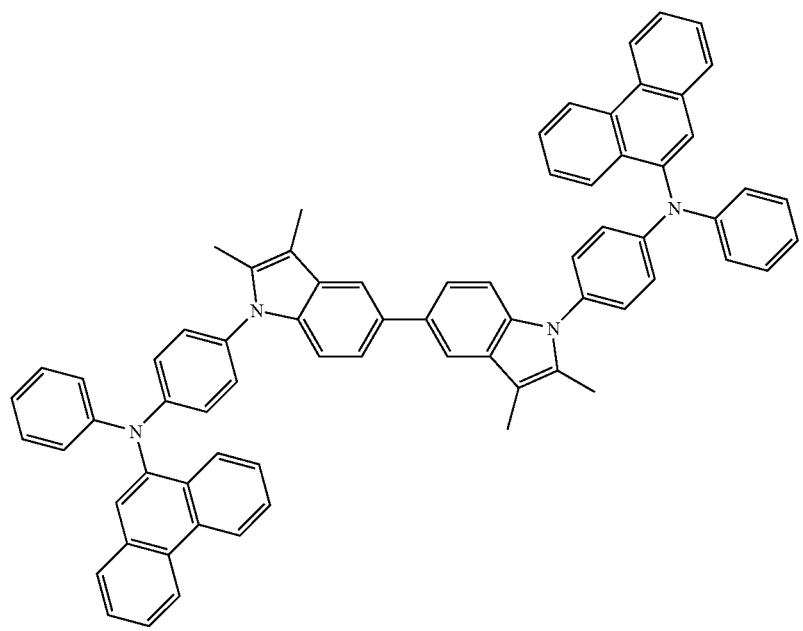
28
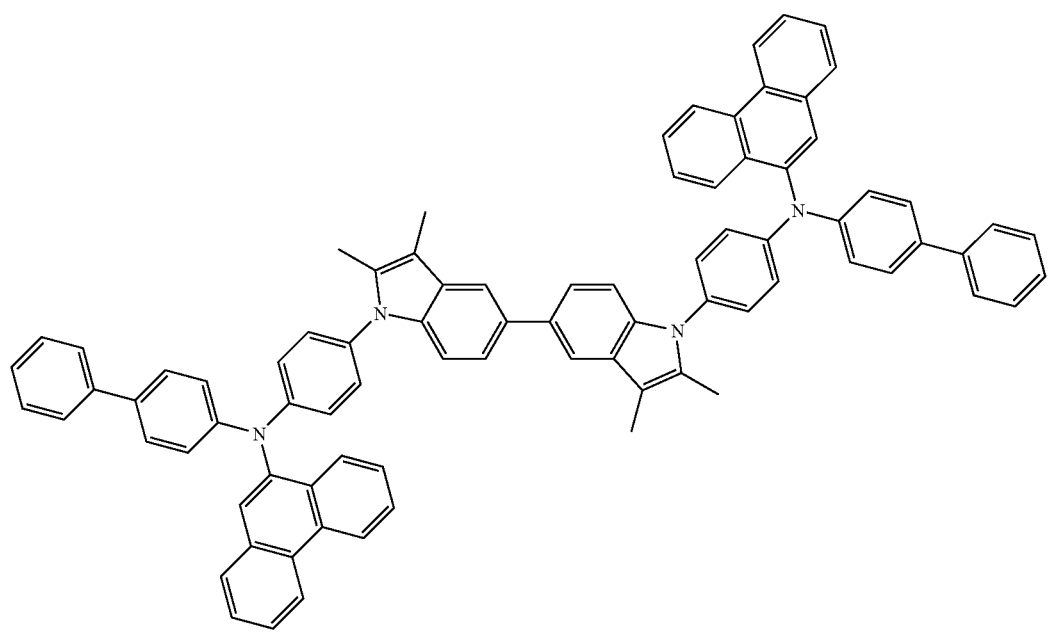

29
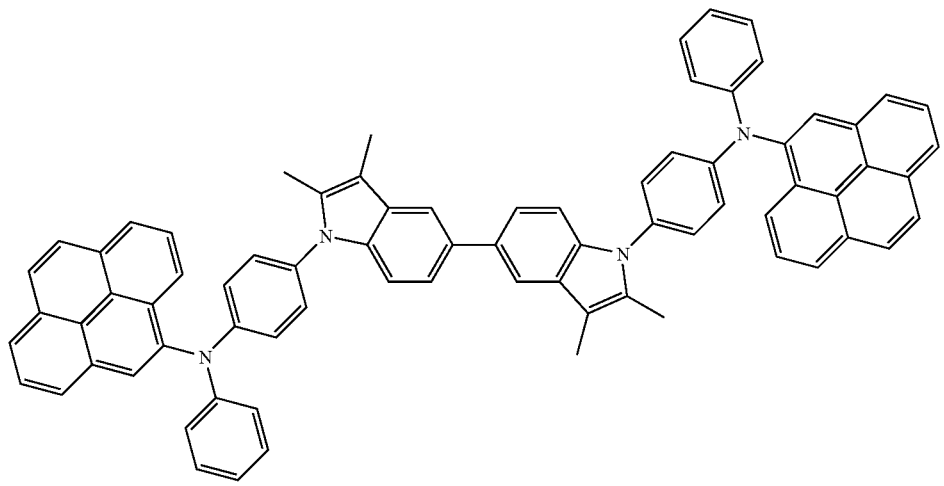
30
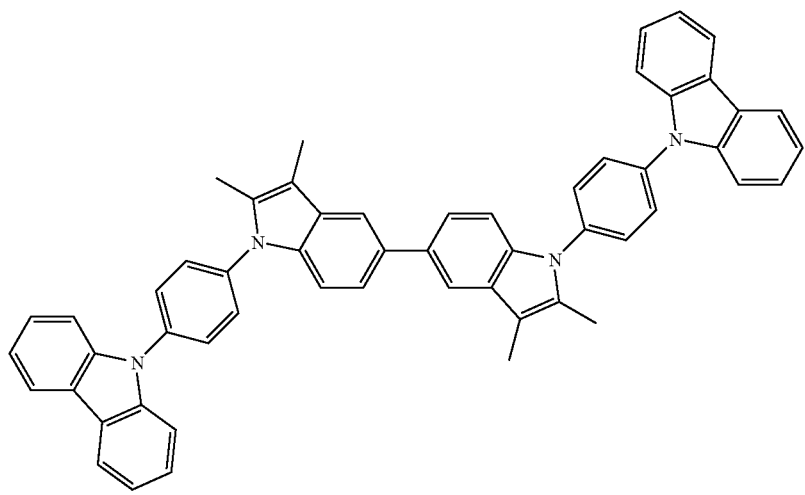
31
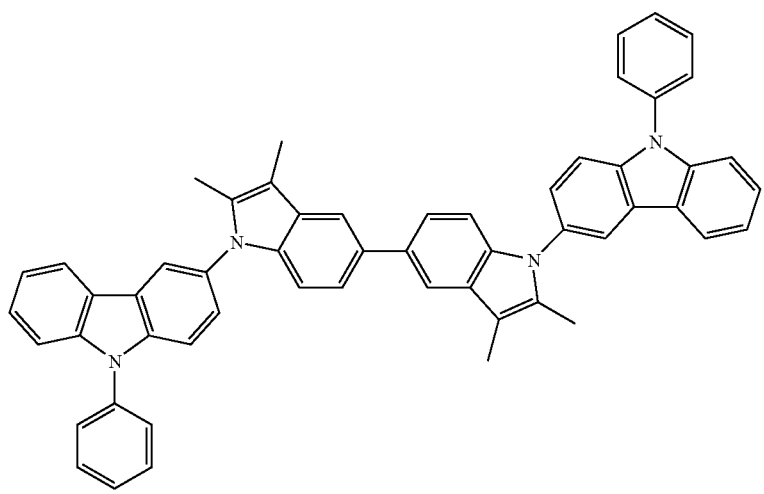

32
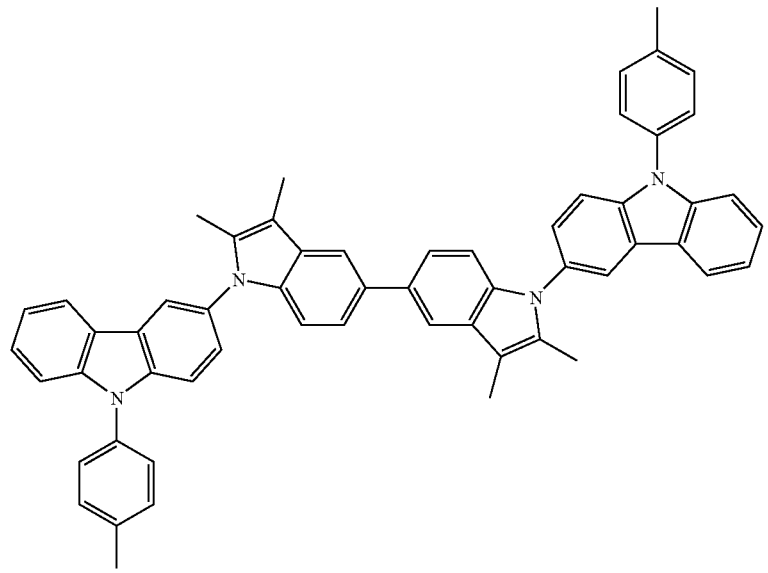
33
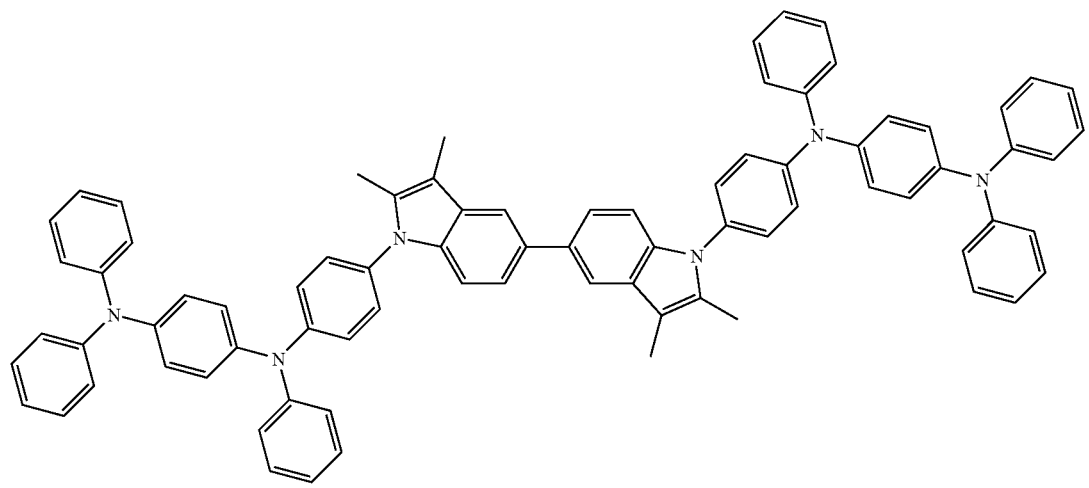
34
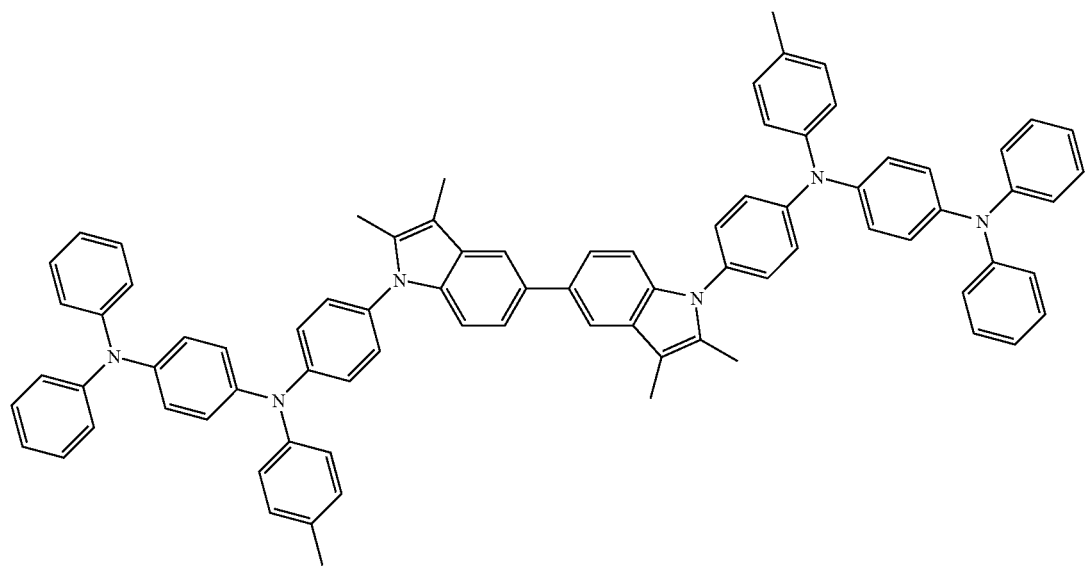

35
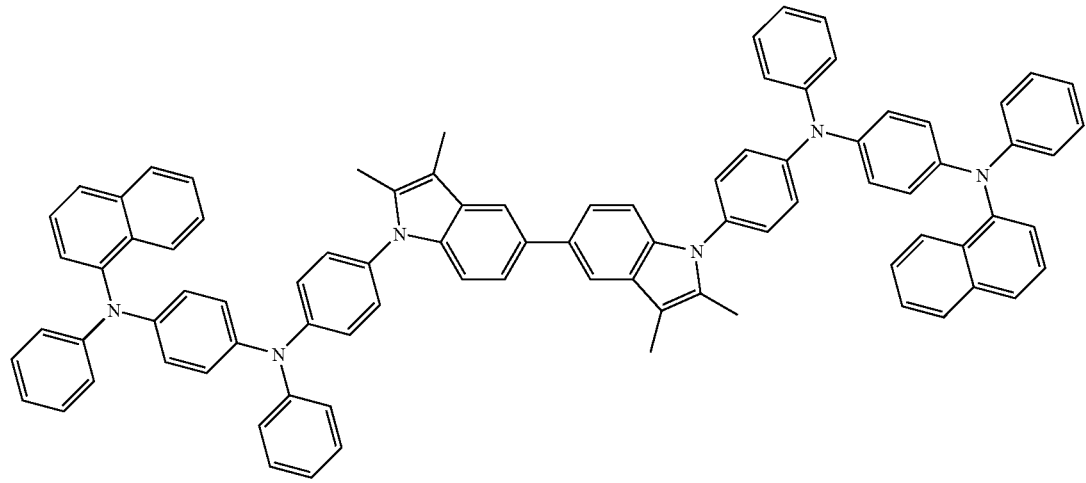
36
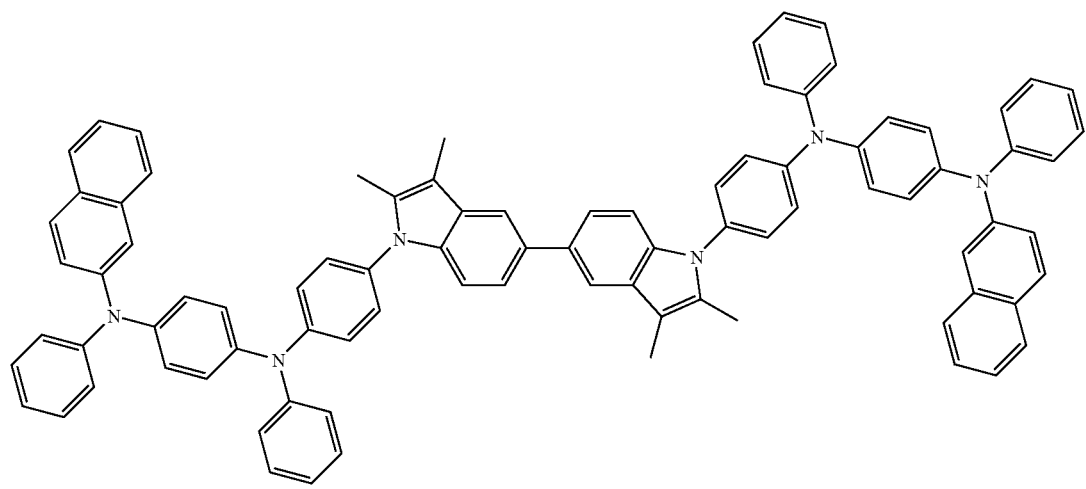
37
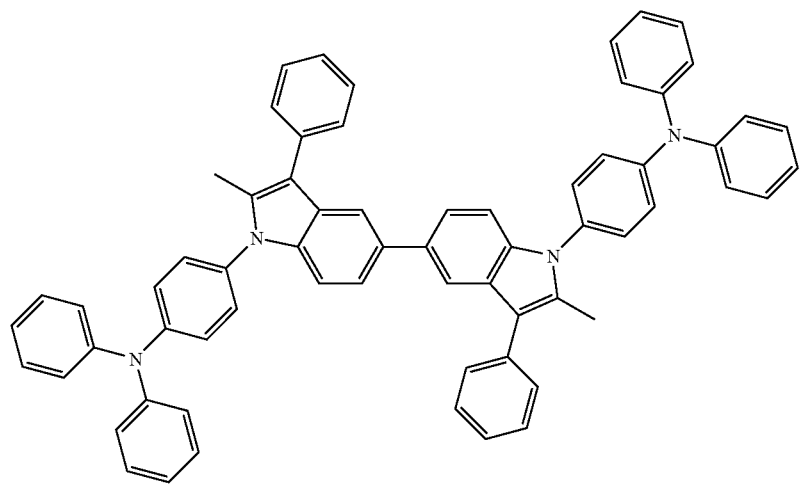

38
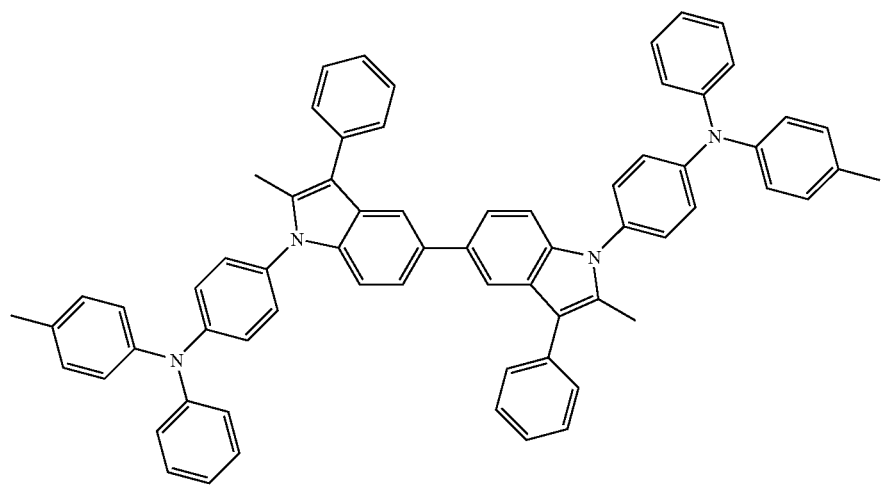
39
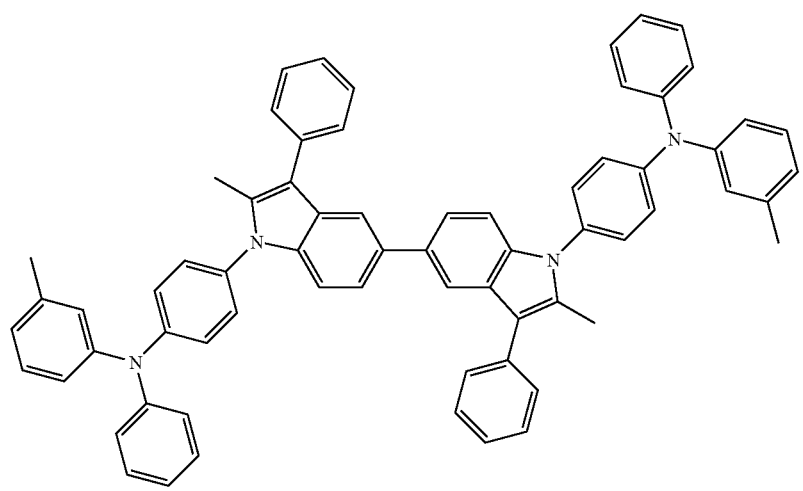
40
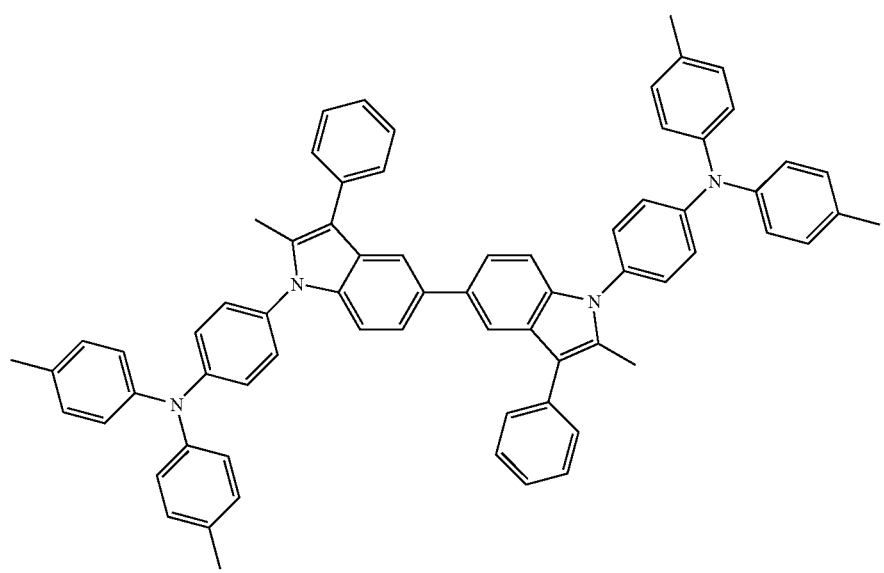

41
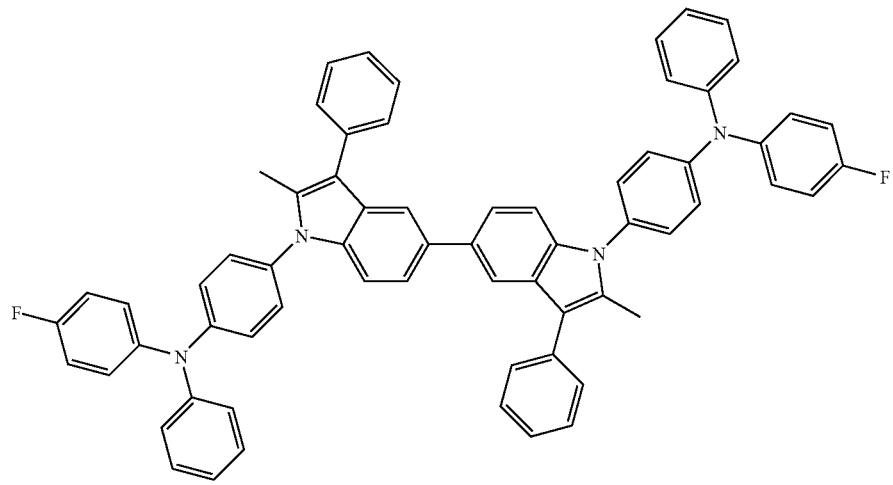
42
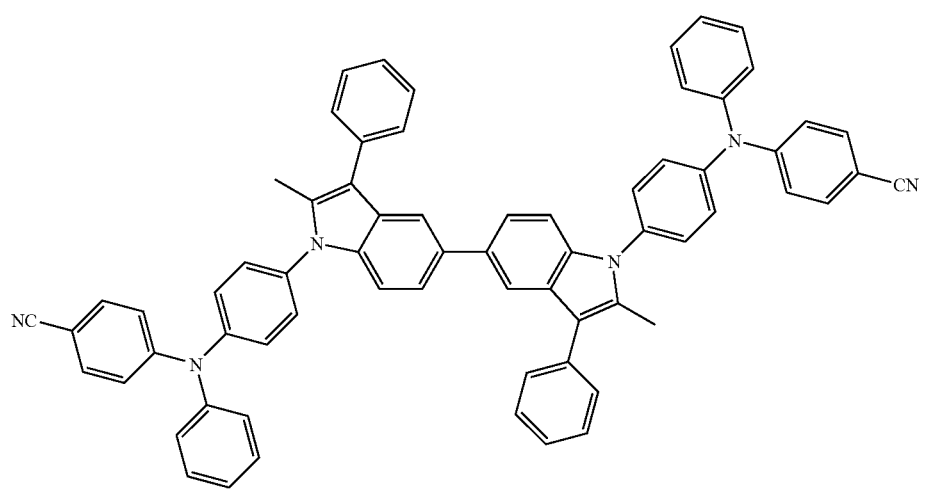
43
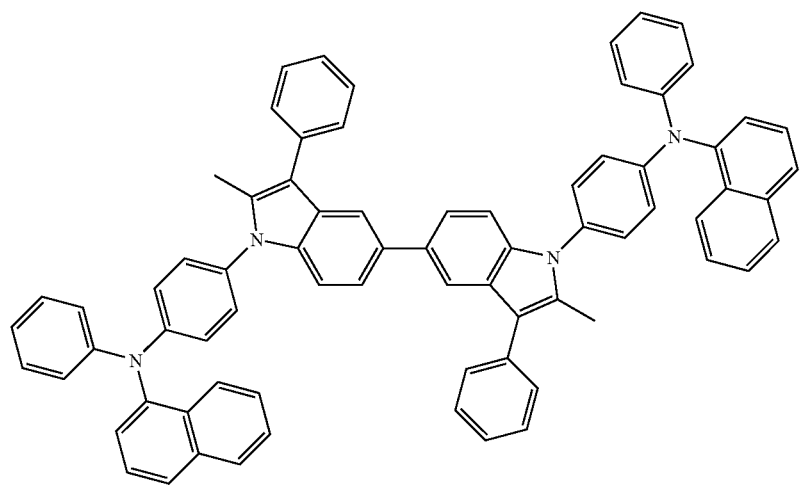

44
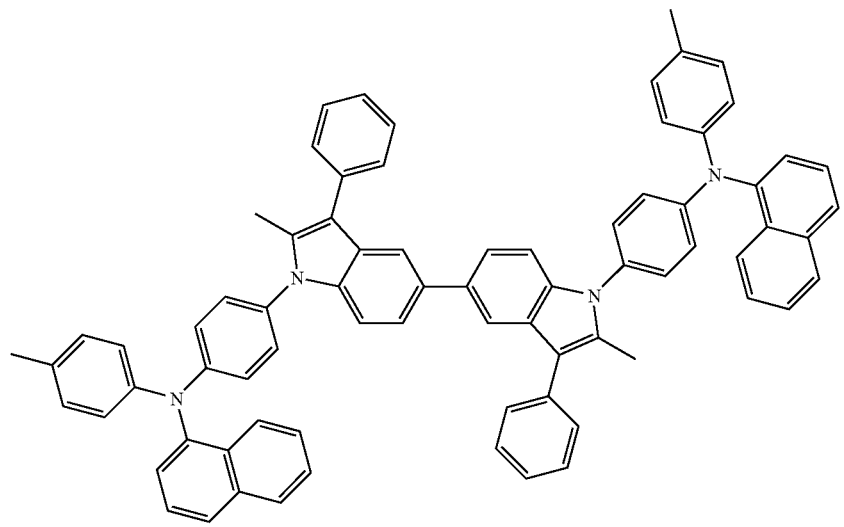
45
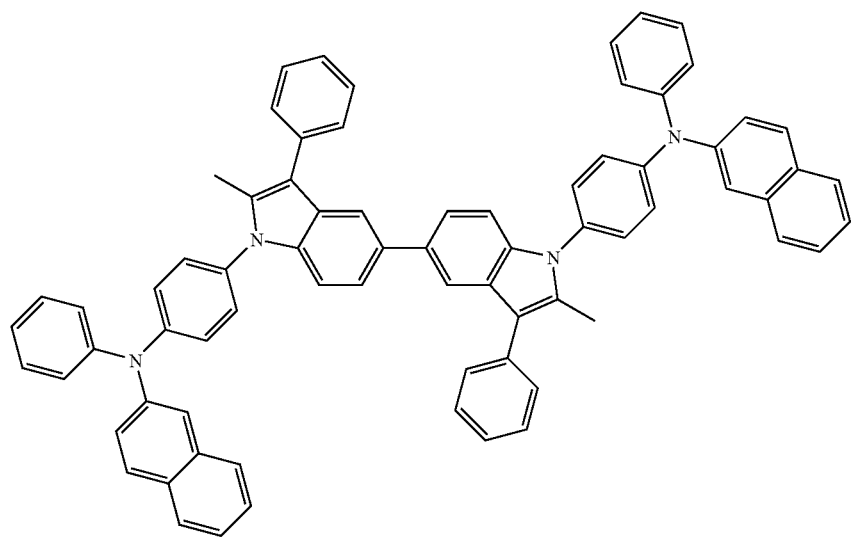
46
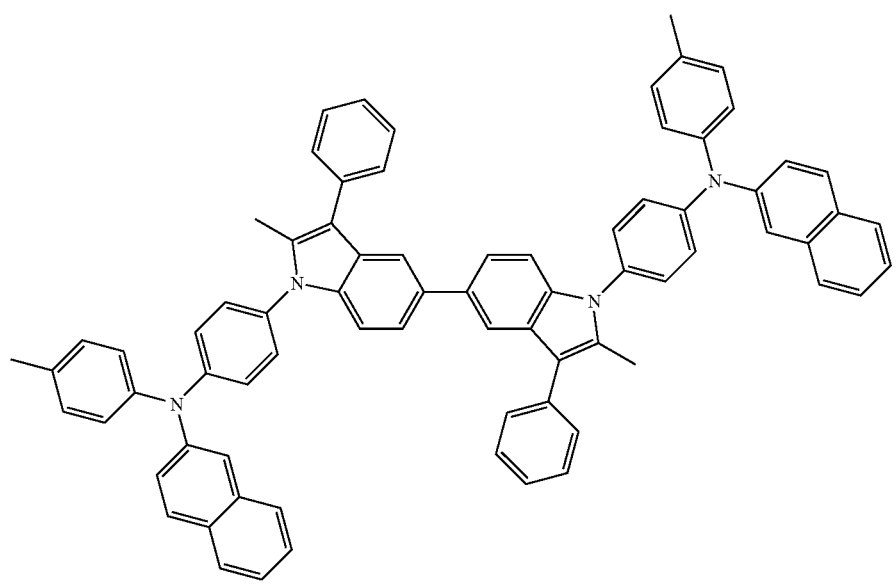

47
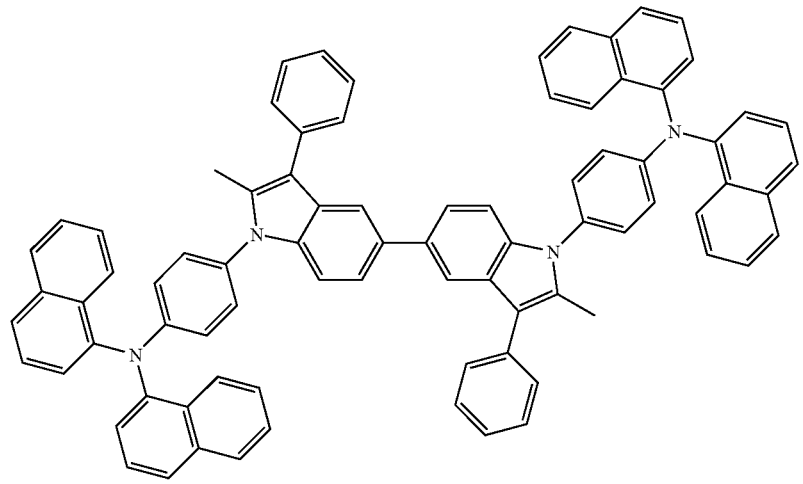
48
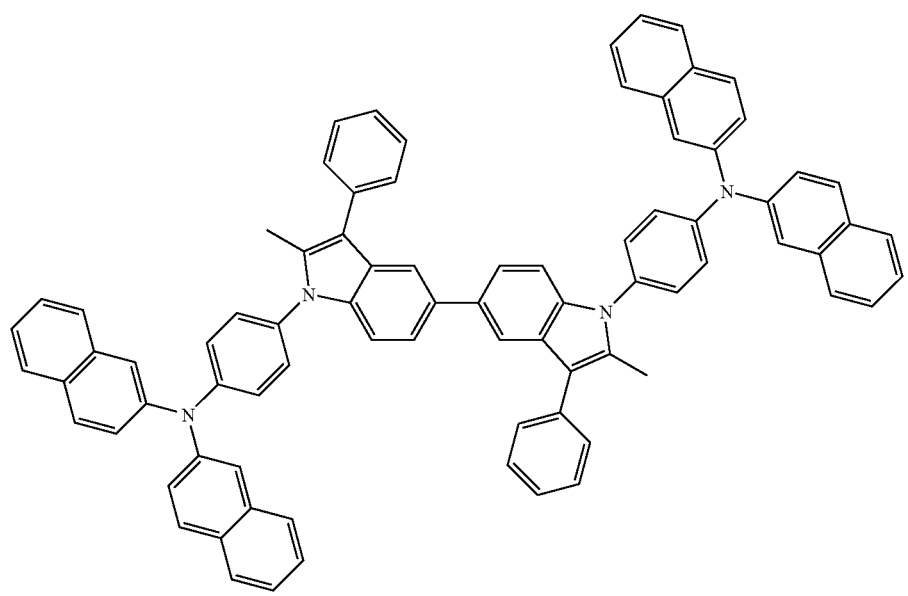
49
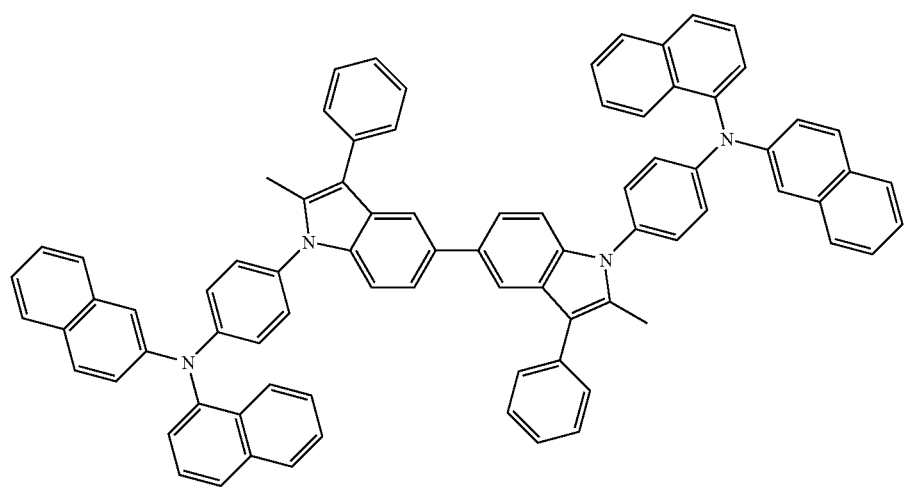

-continued
50
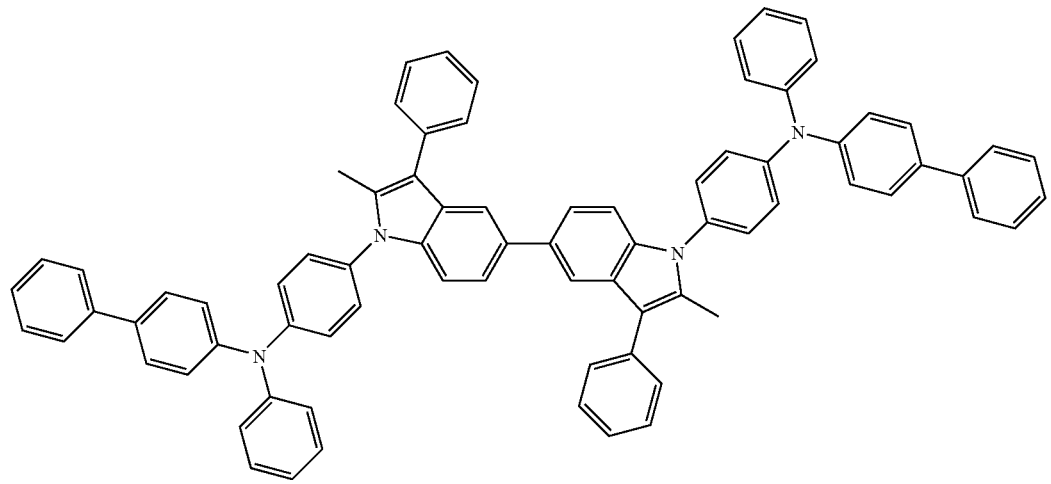
51
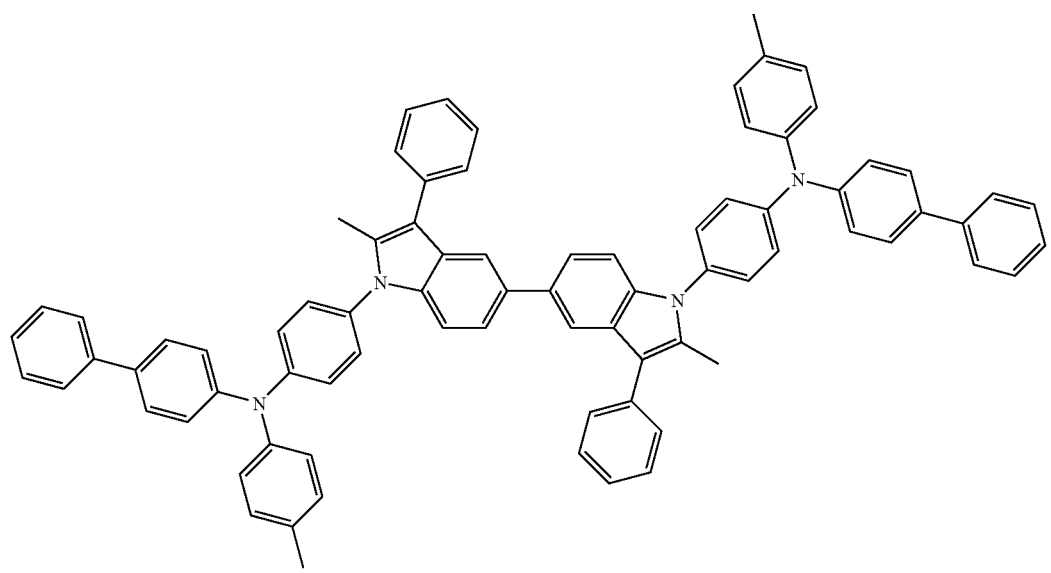
52
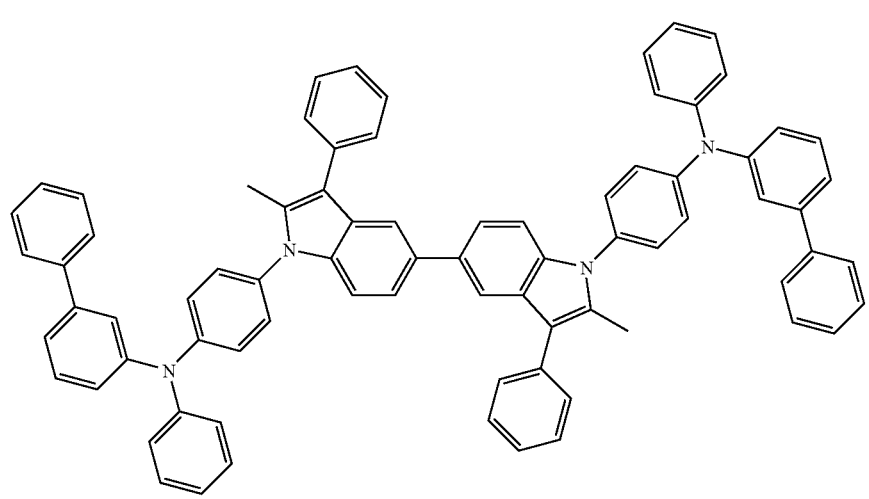

-continued
53
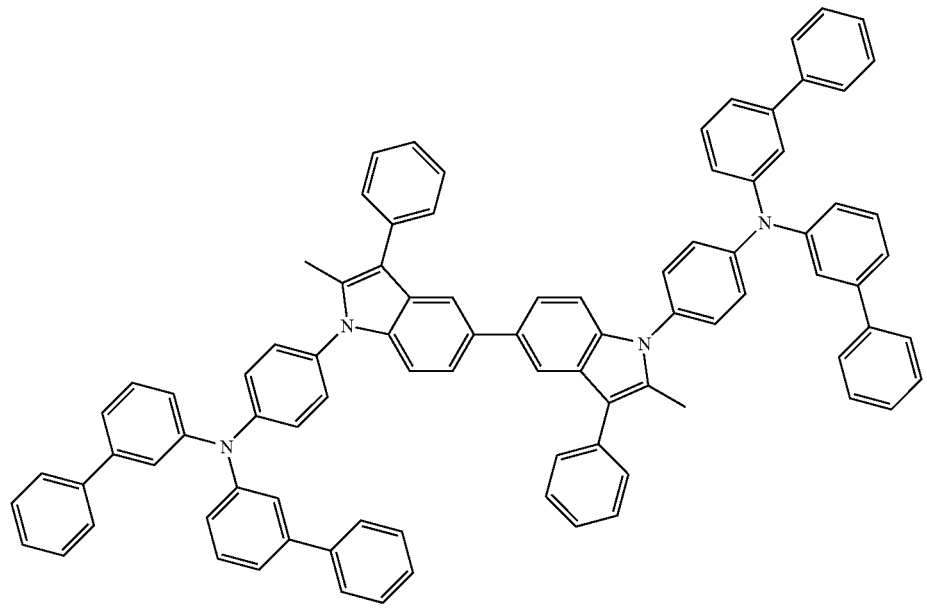
54
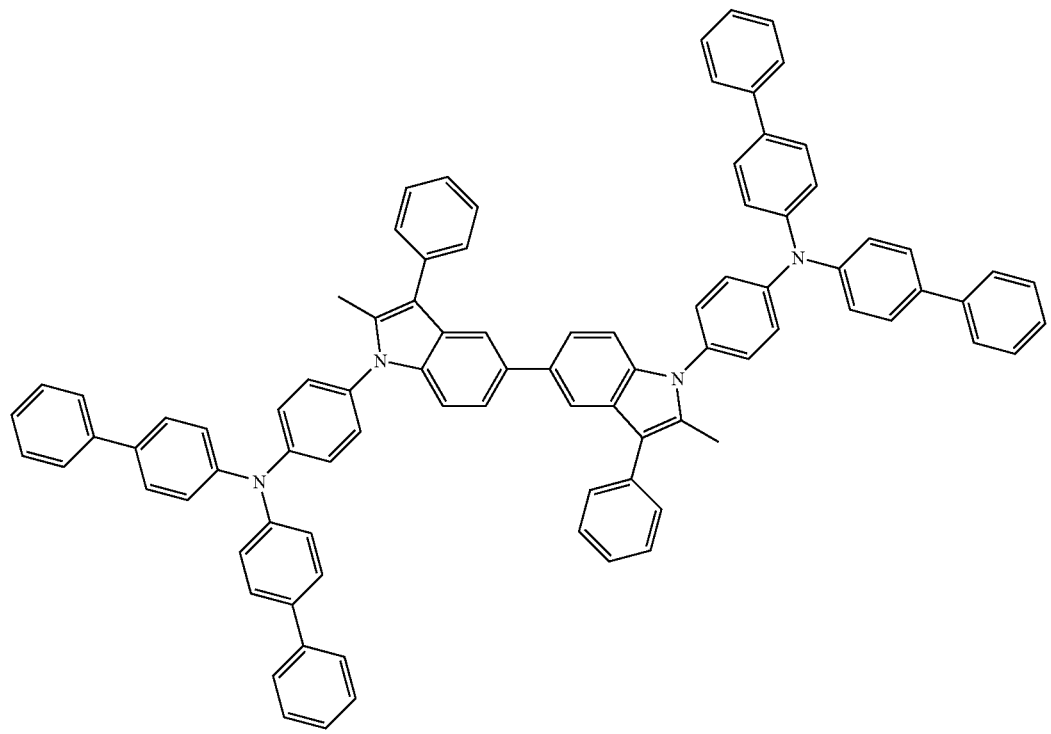

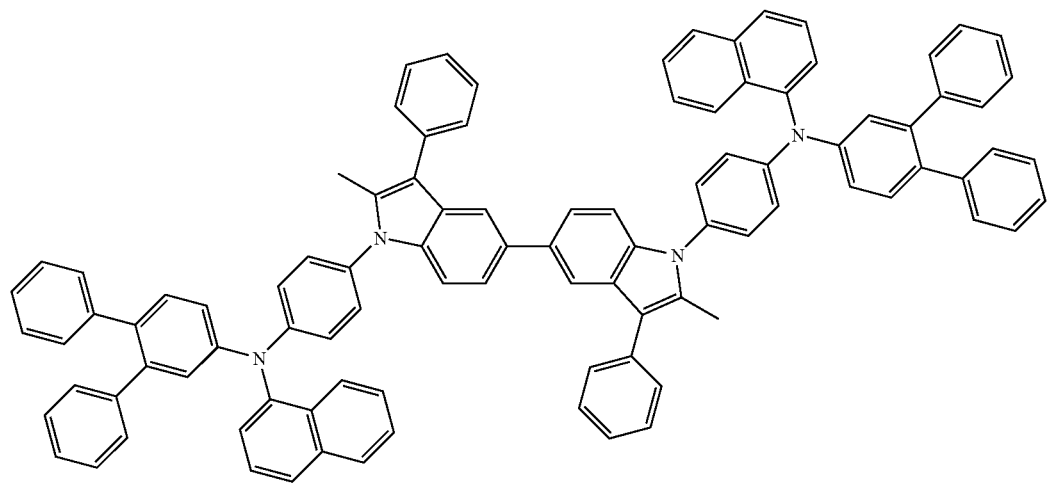
55
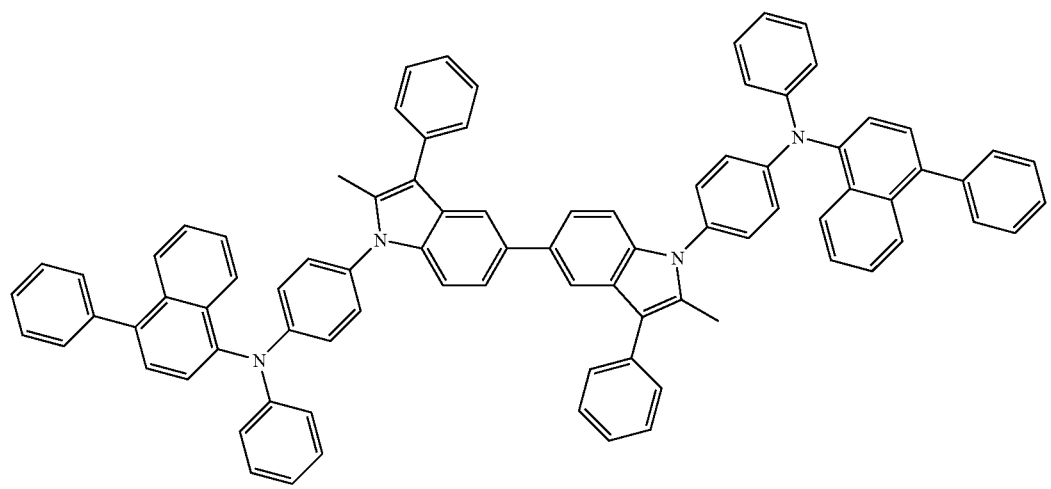
56
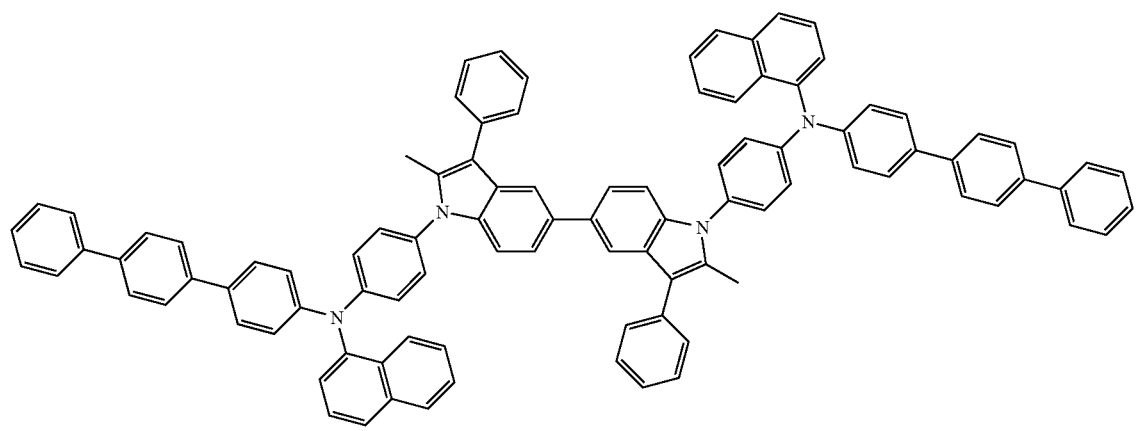
57

58
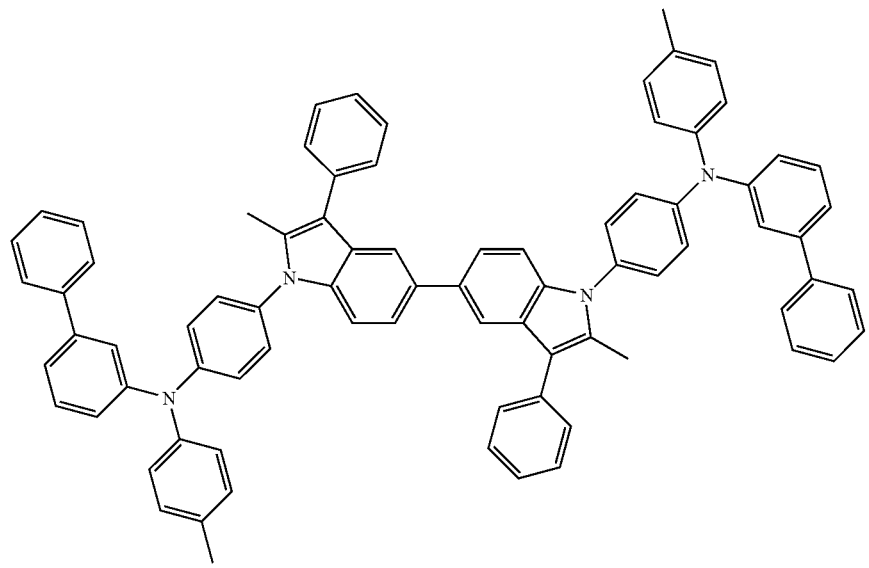
59
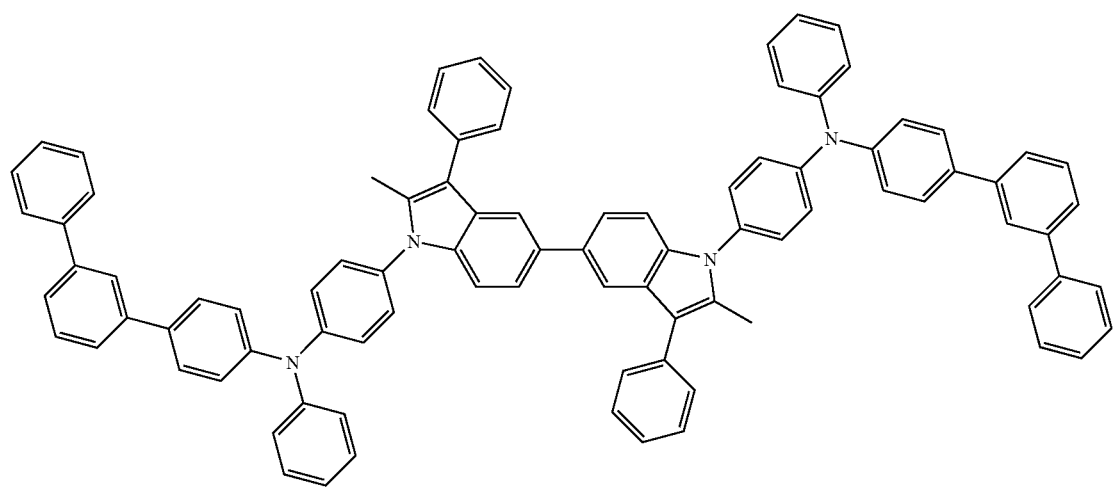
60
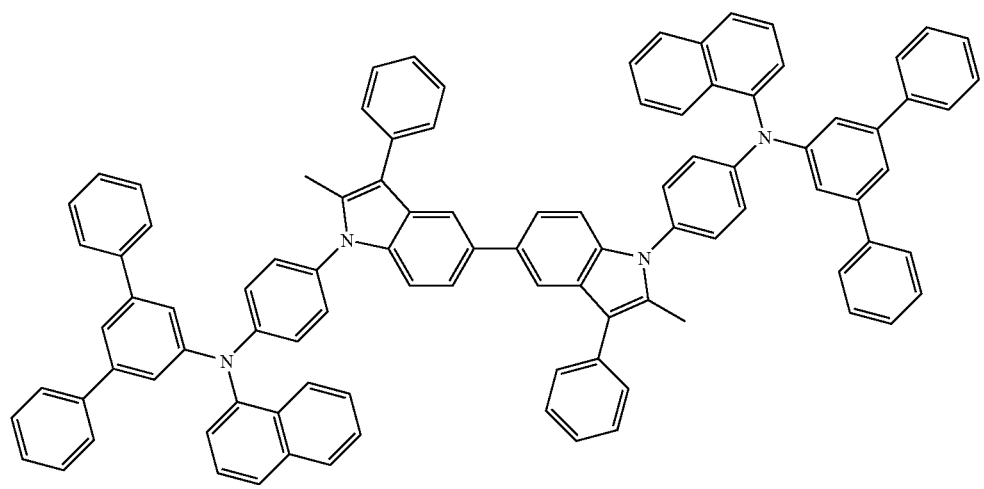

61
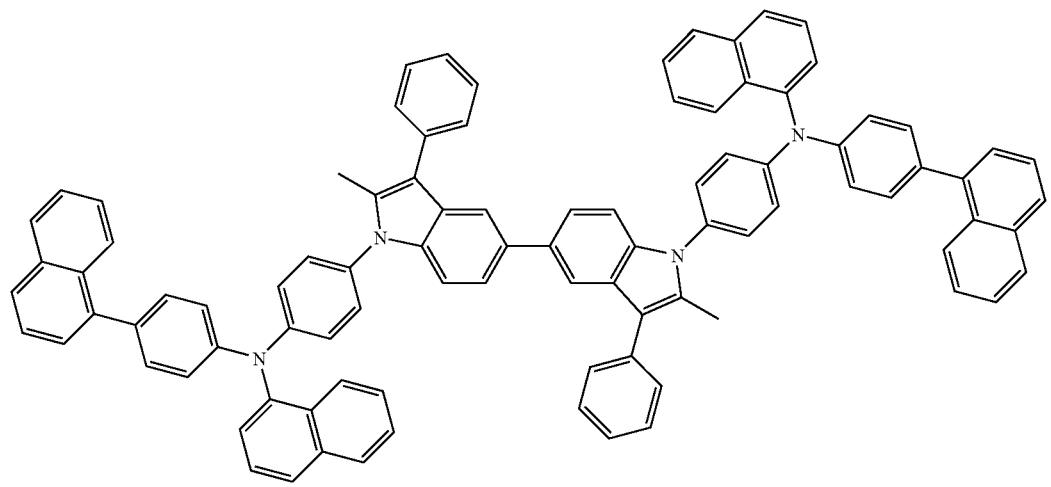
62
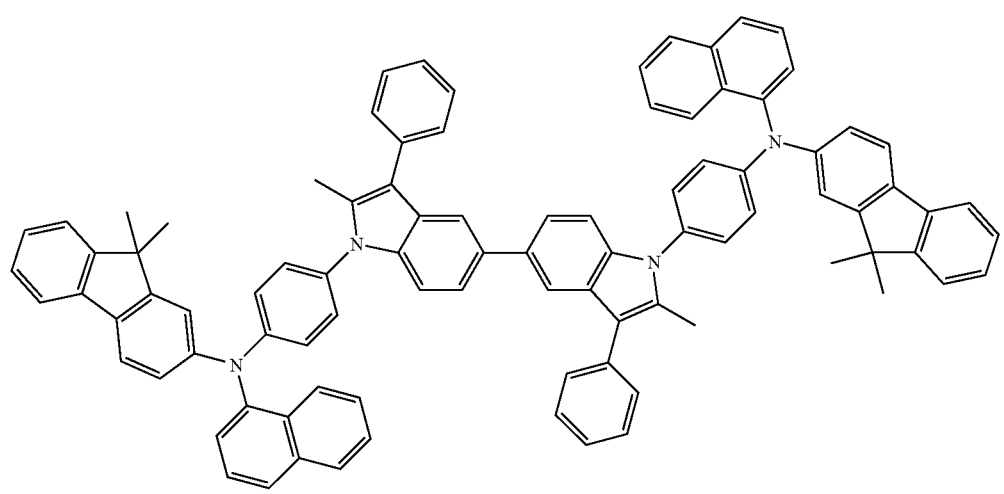
63
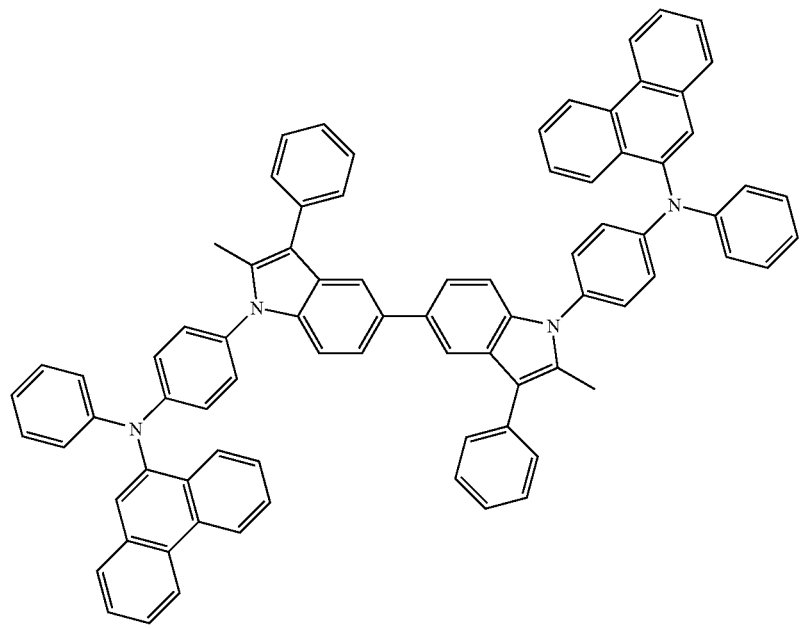

-continued
64
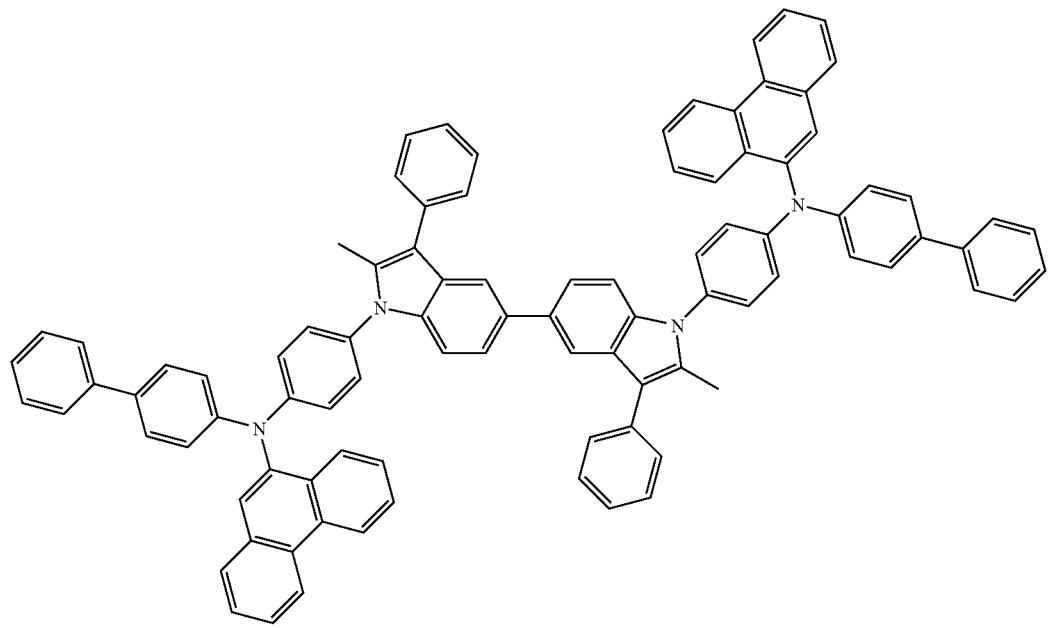
65
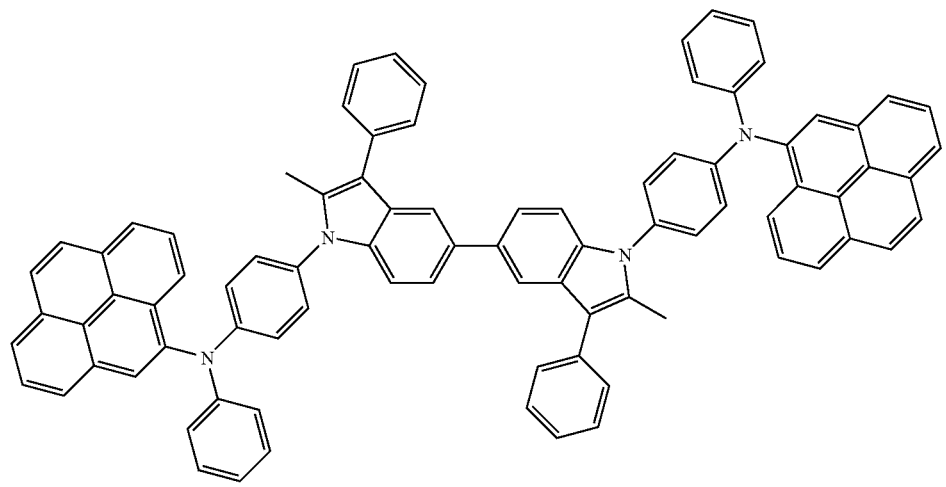
66
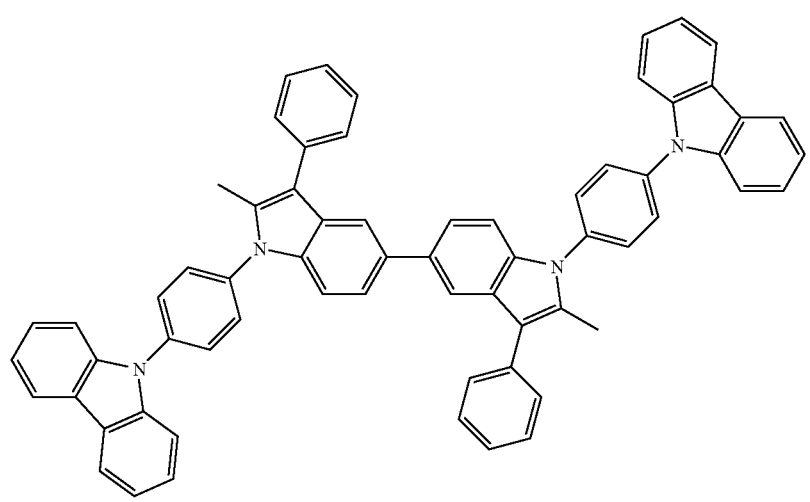

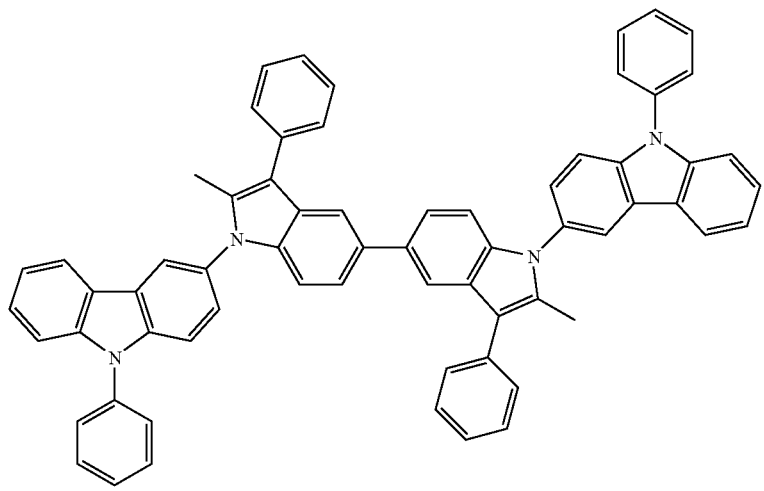
67
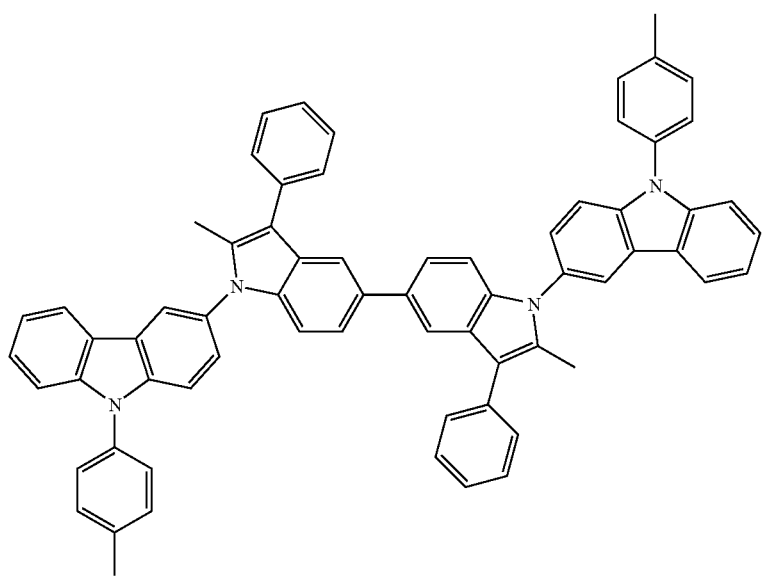
68
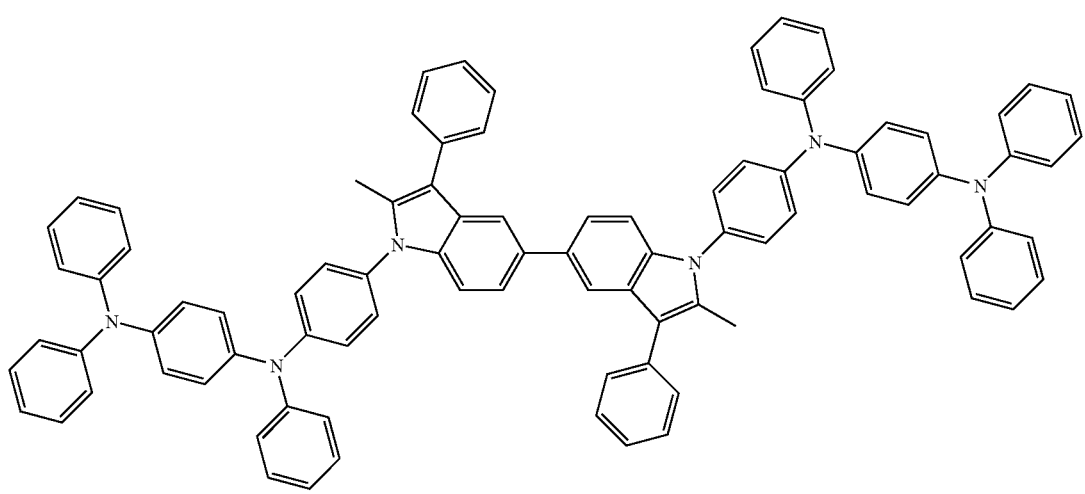
69

70
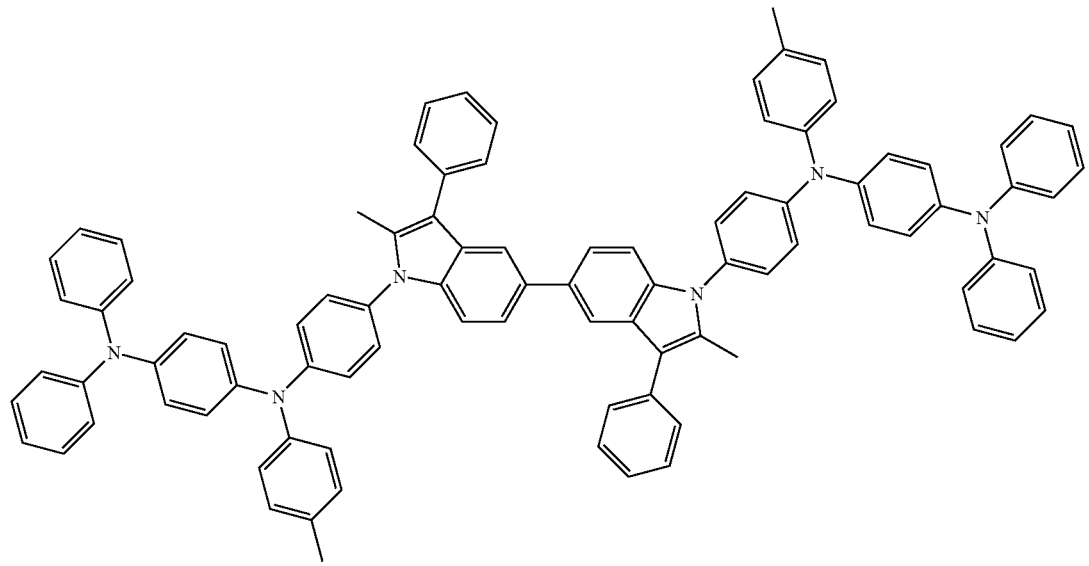
71
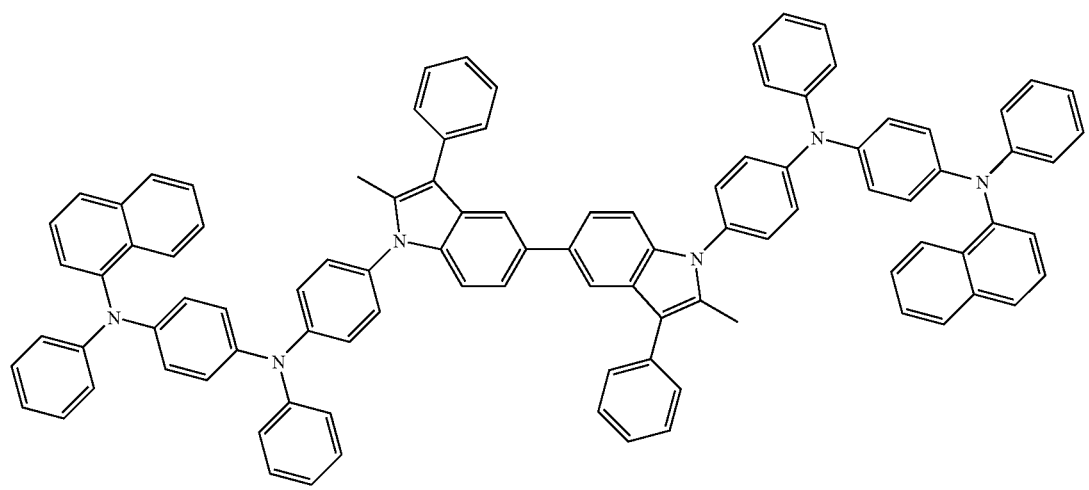
72
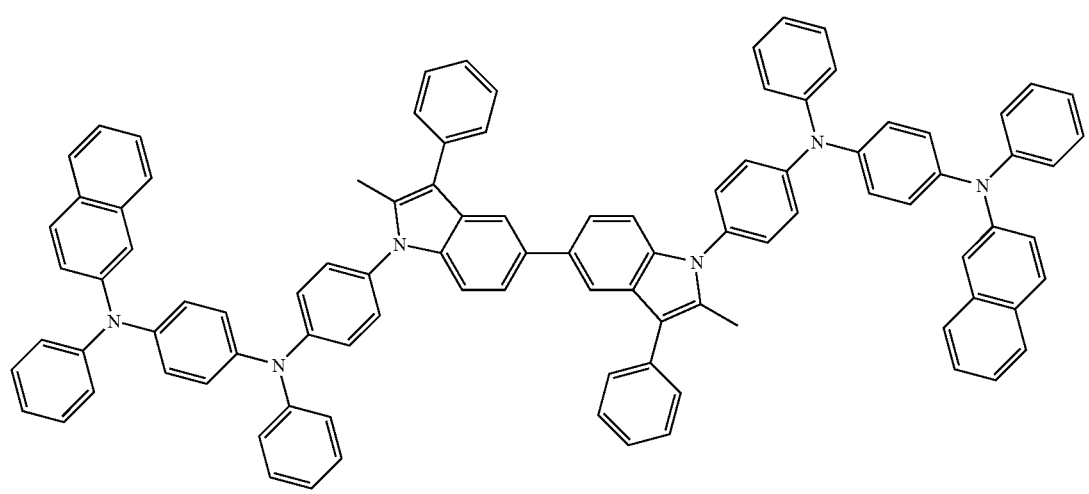

73
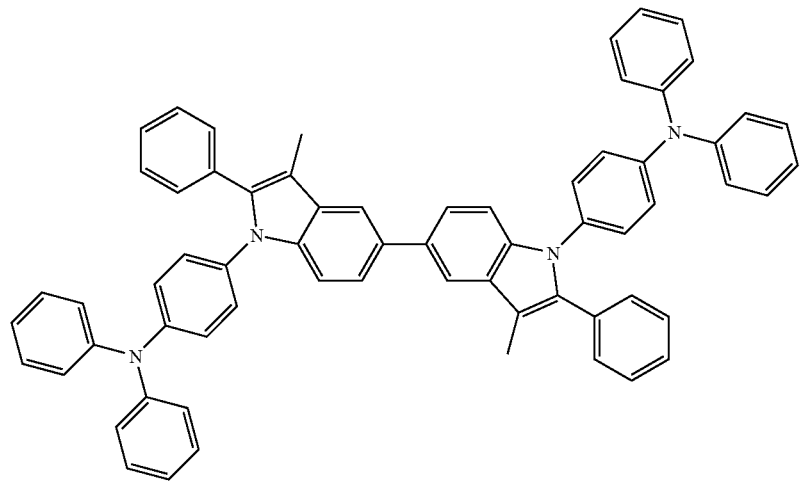
74
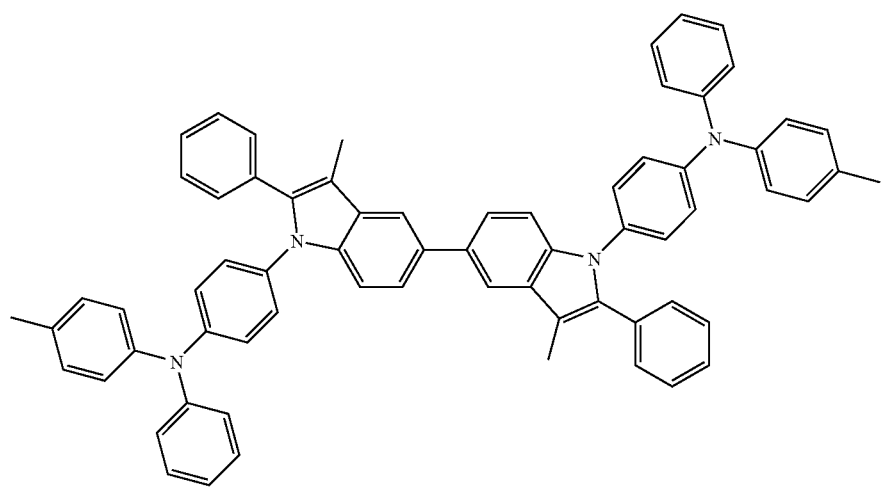
75
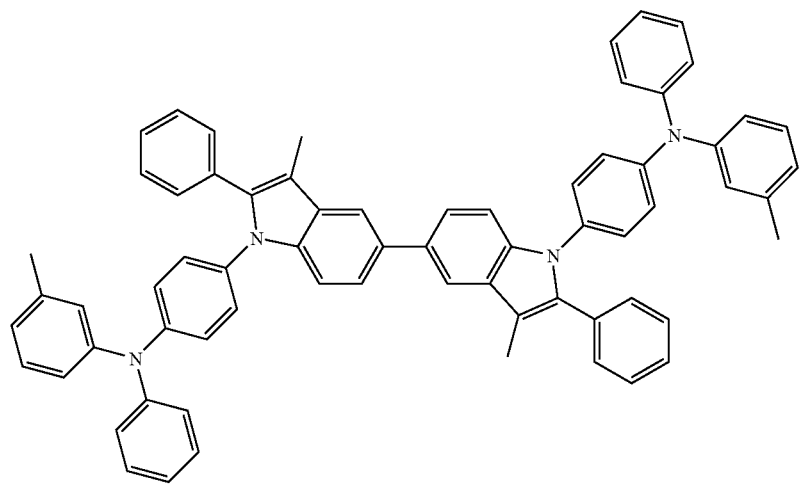

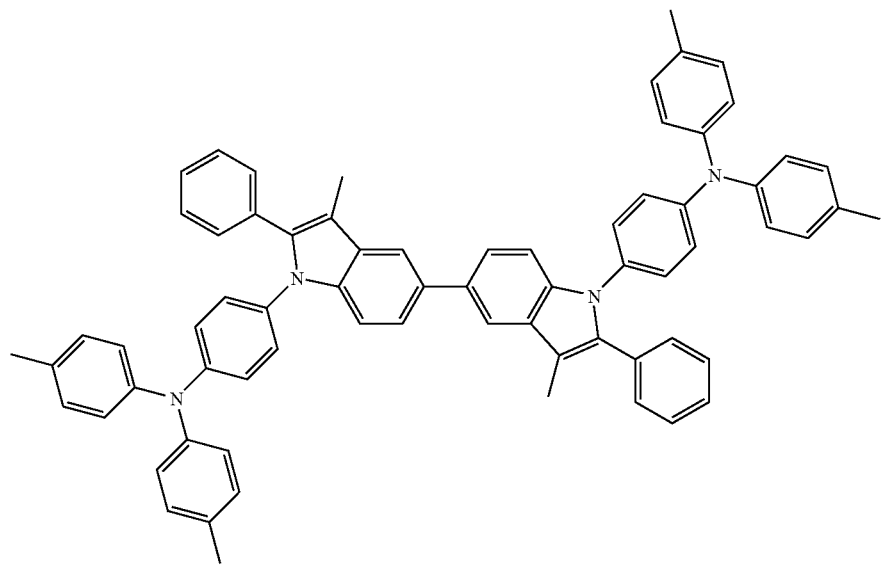
76
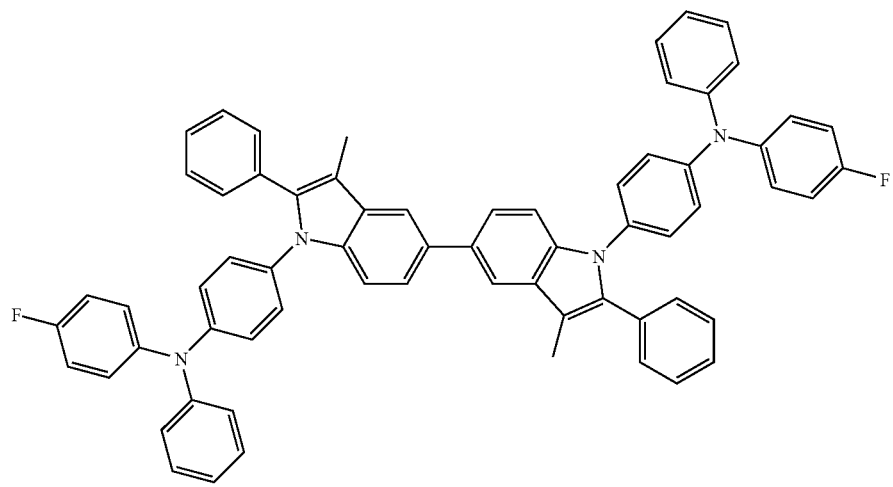
77
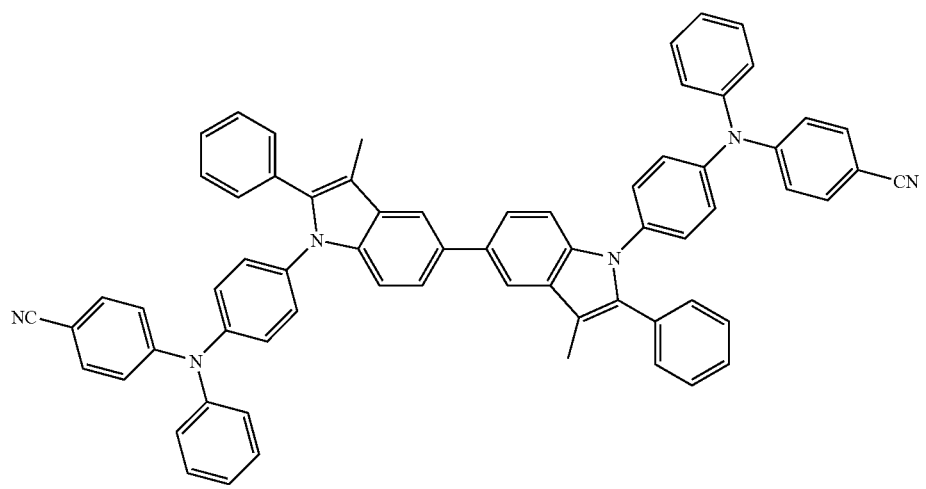
78

79
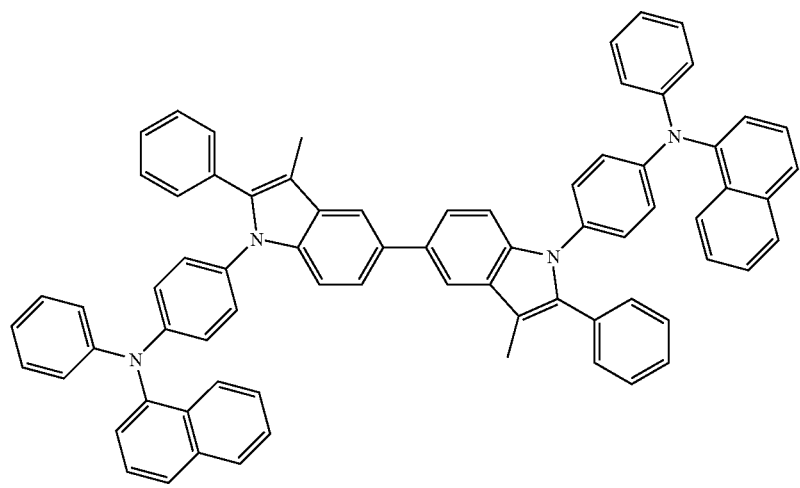
80
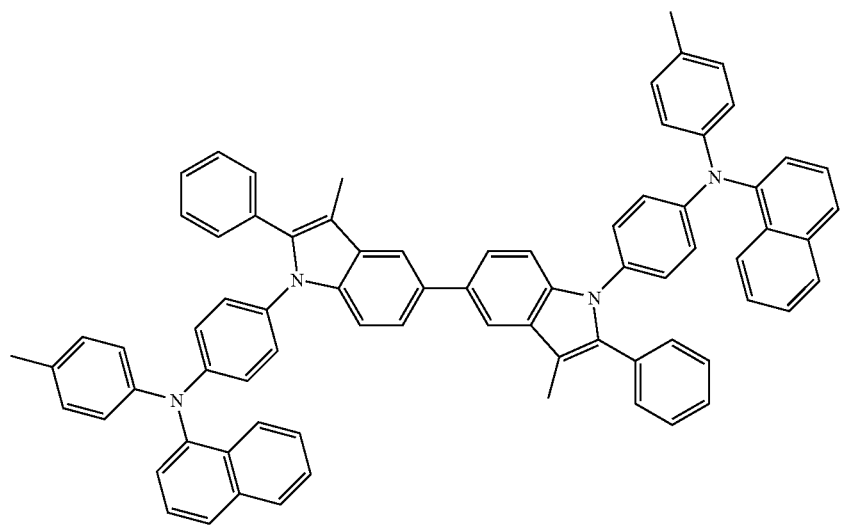
81
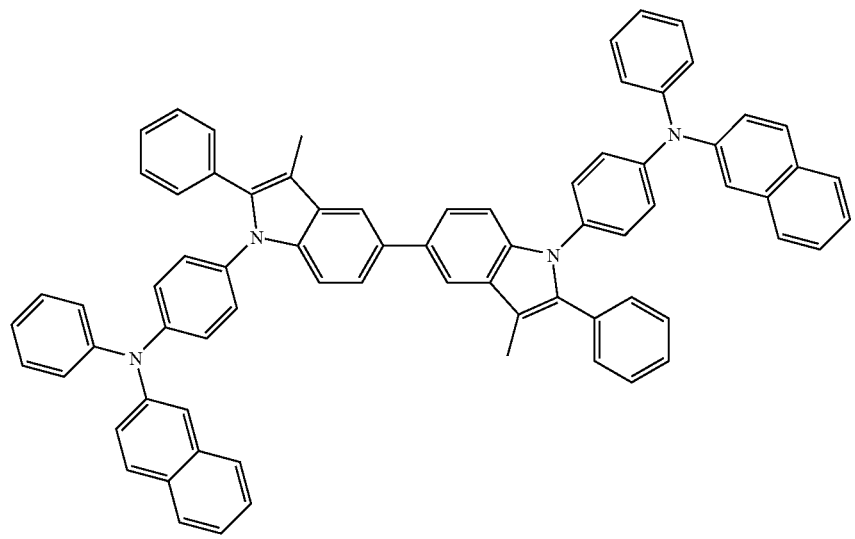

82
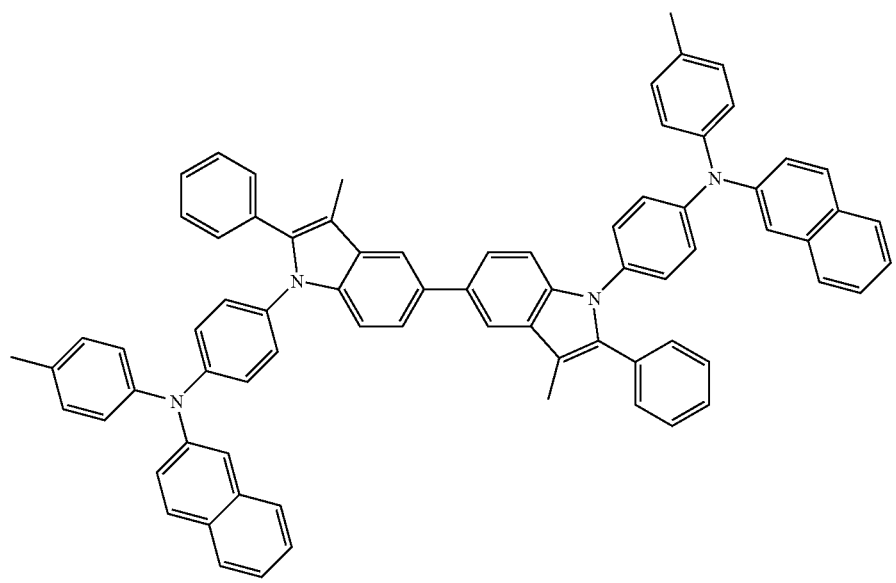
83
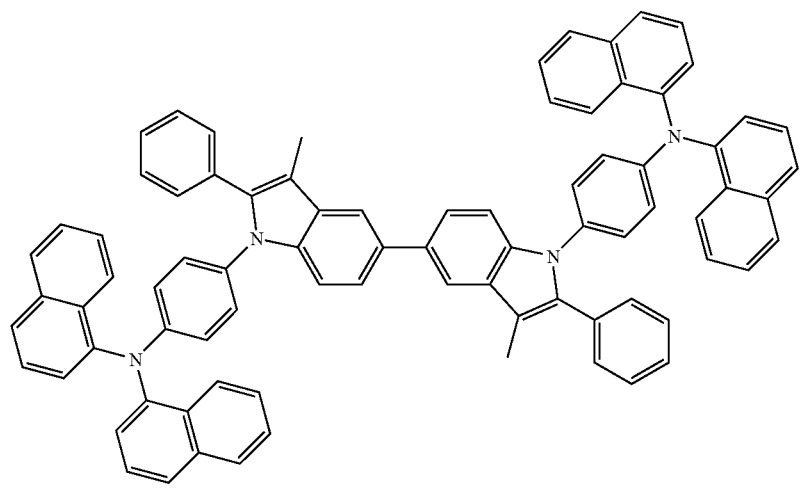
84
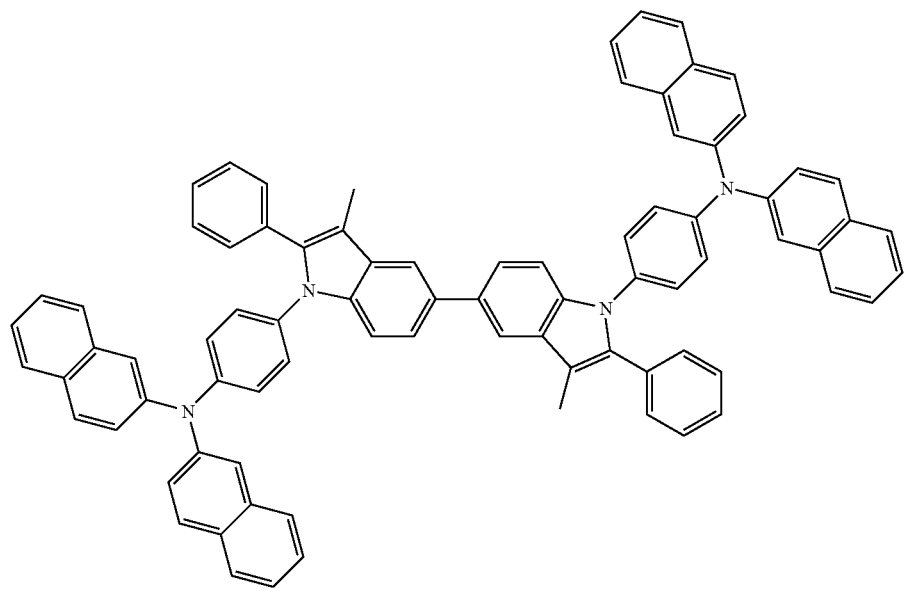

85
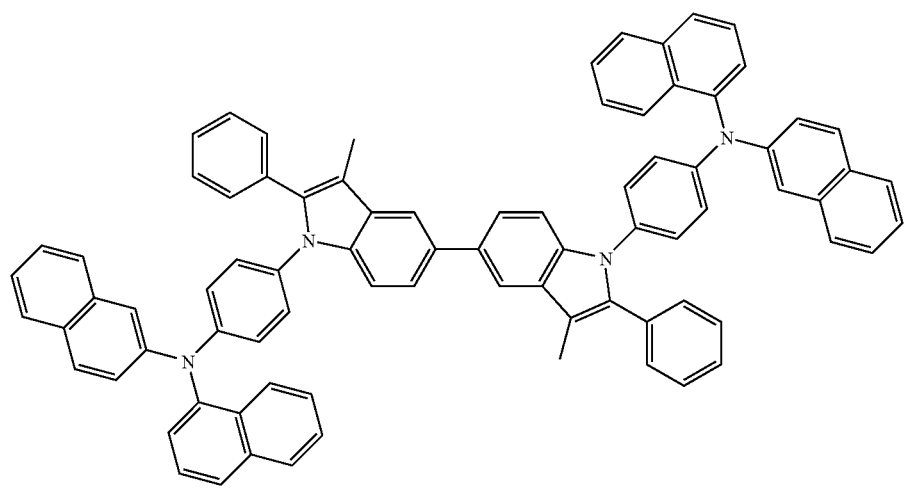
86
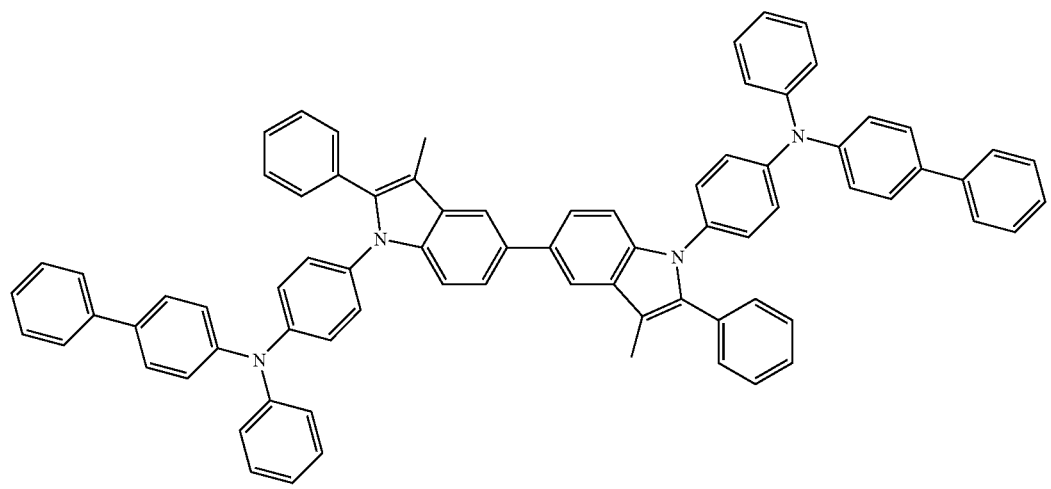
87
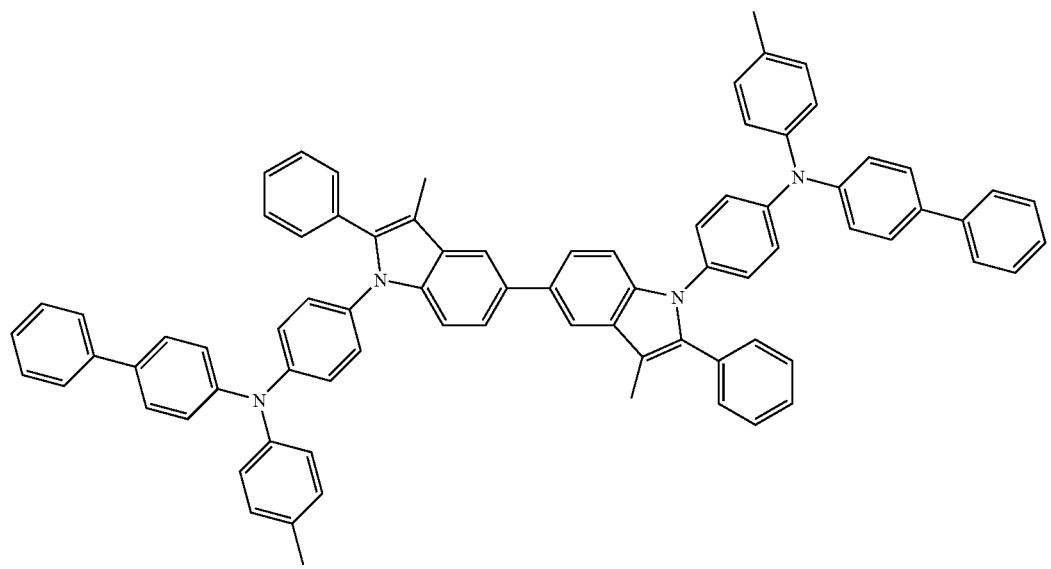

88
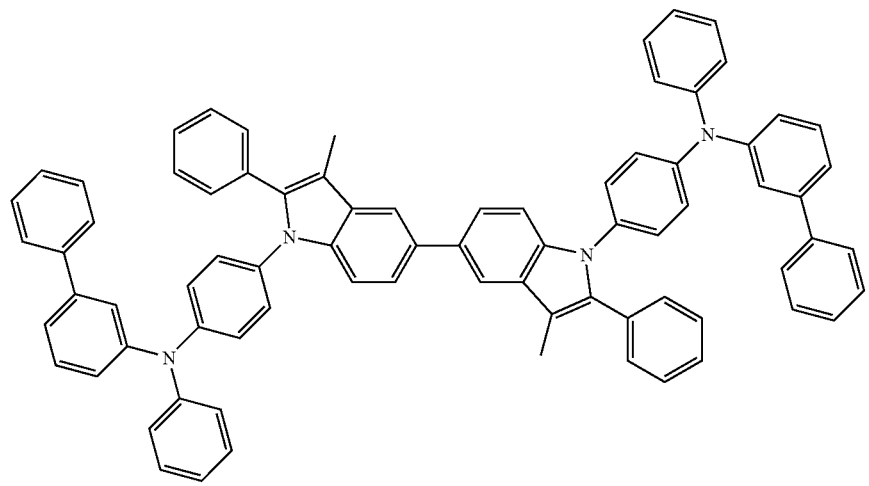
89
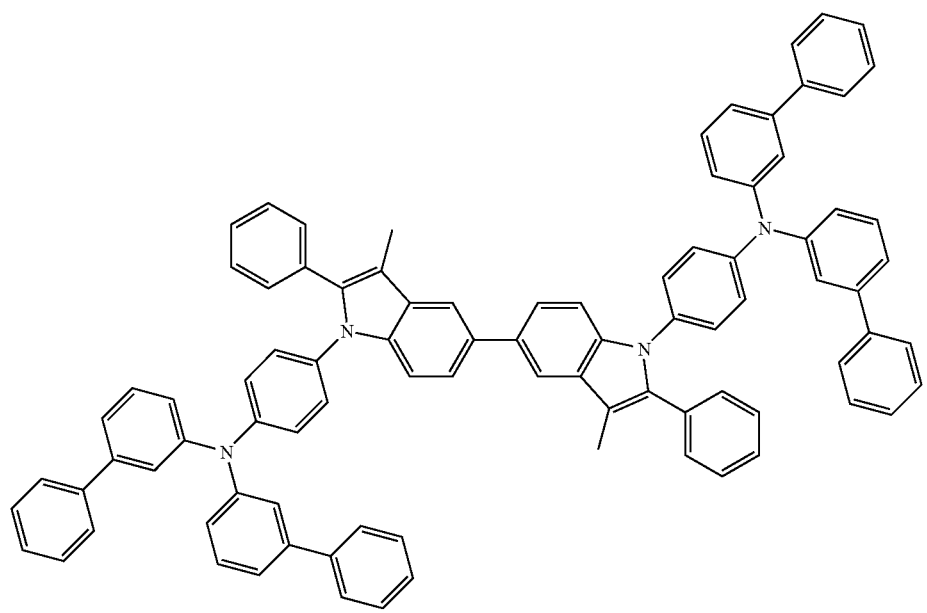

-continued
90
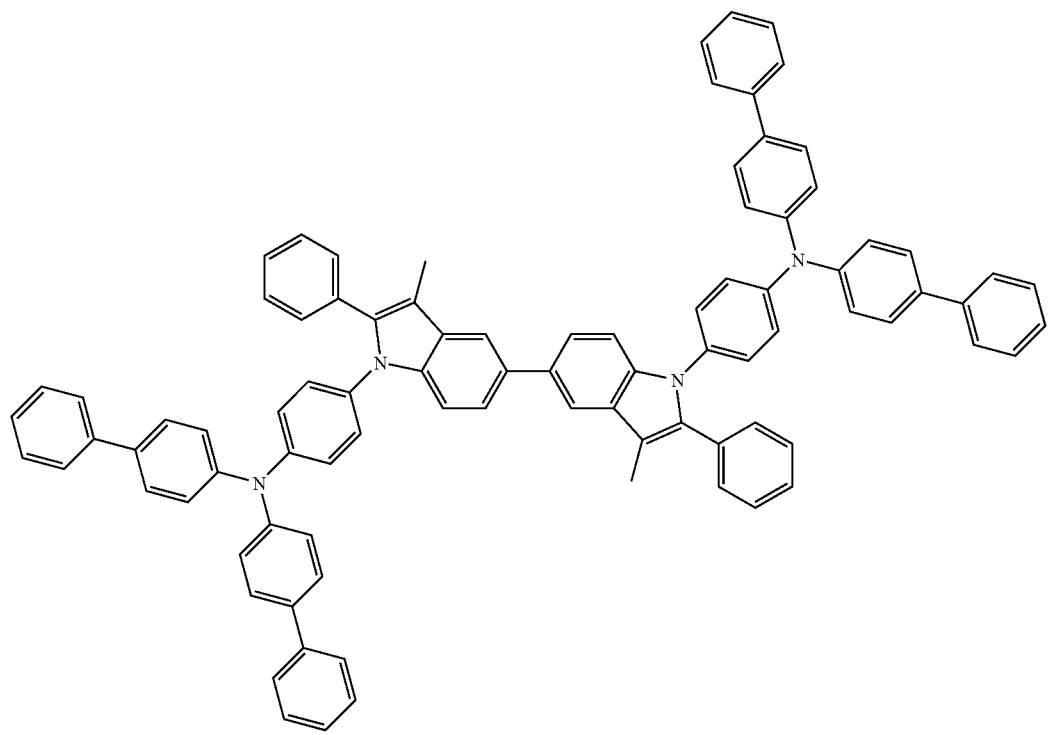
91
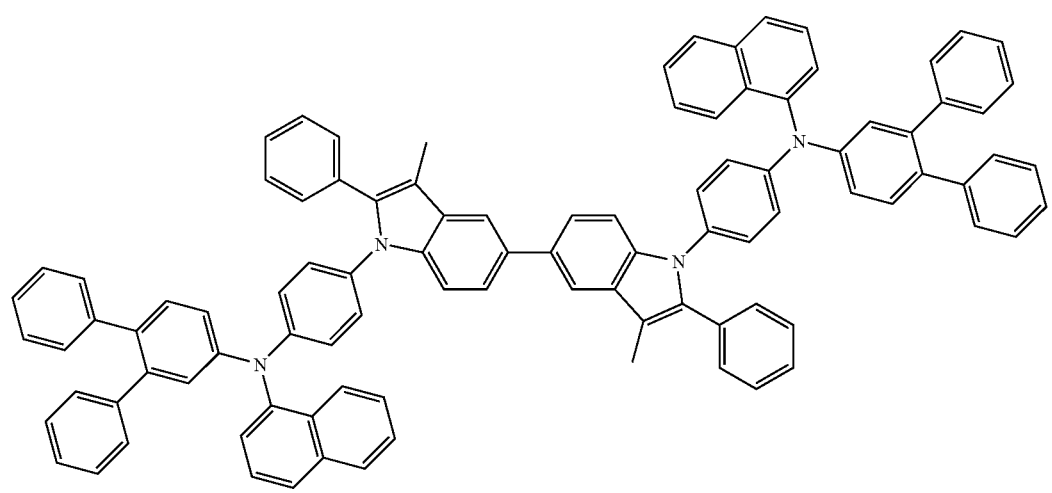

92
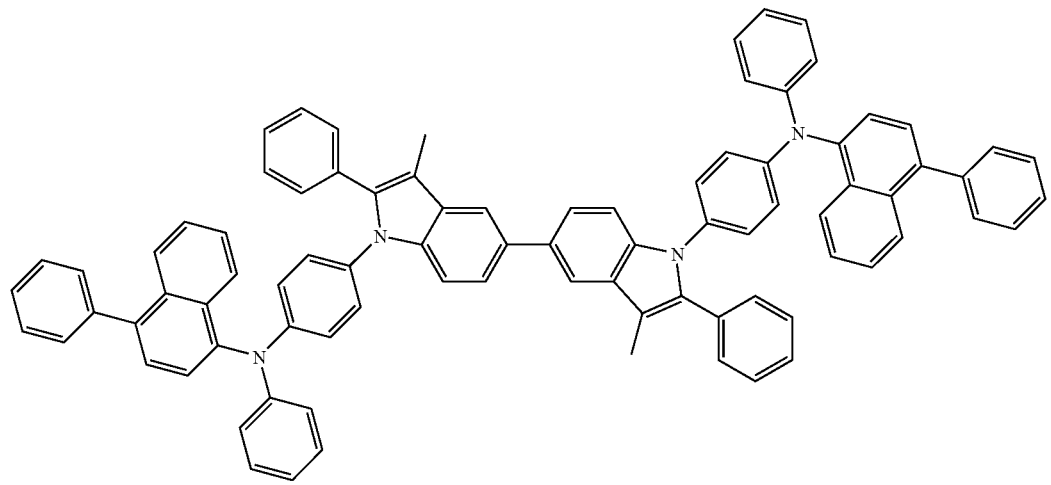
93
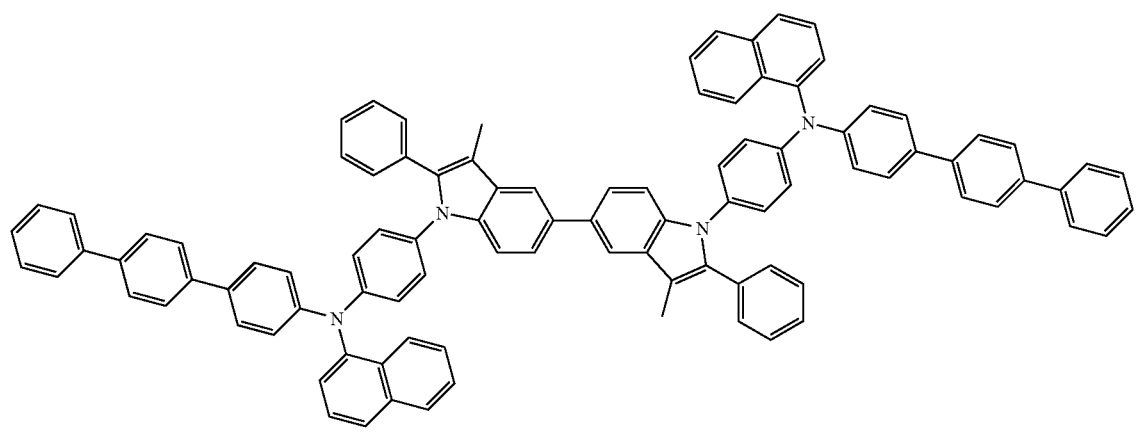
94
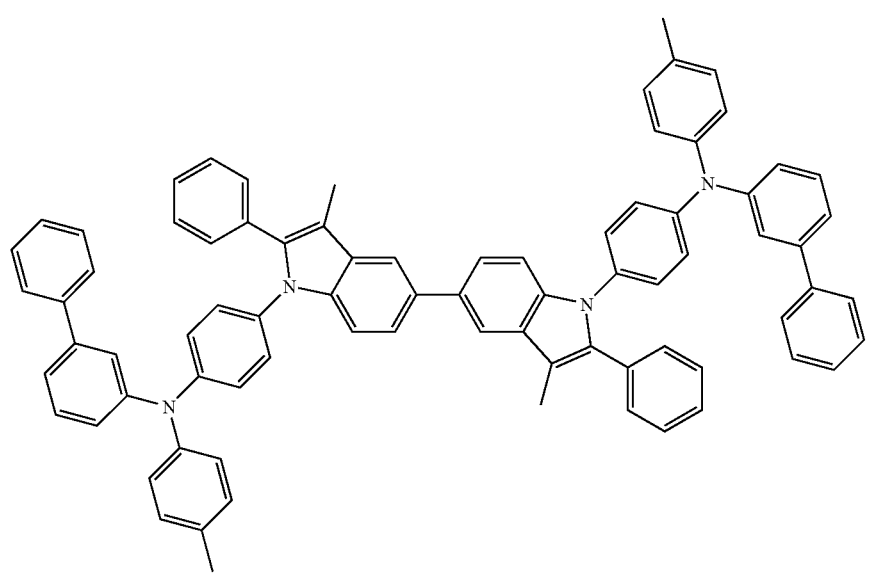

-continued
95
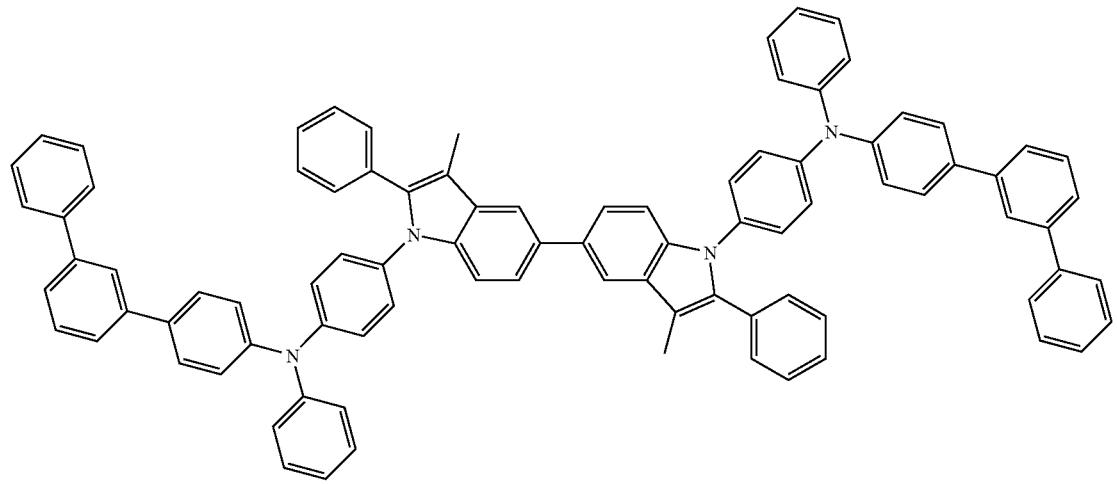
96
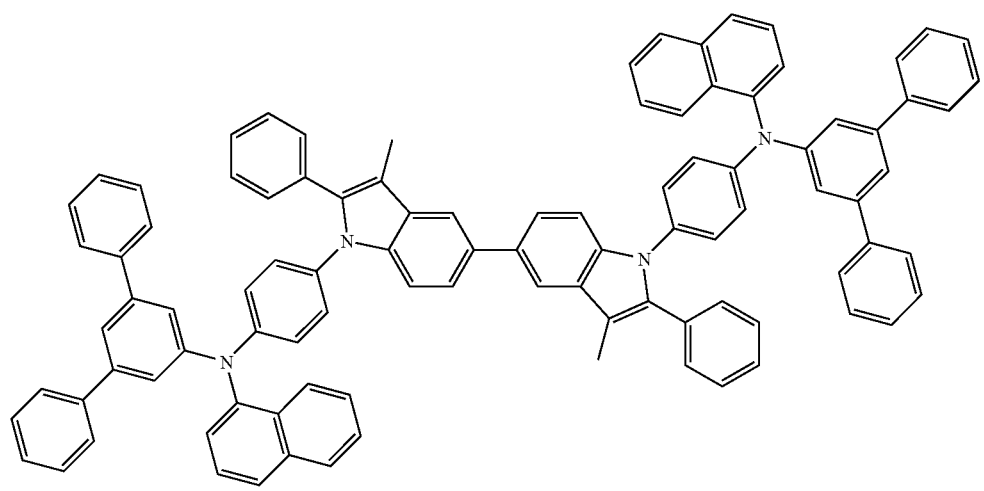
97
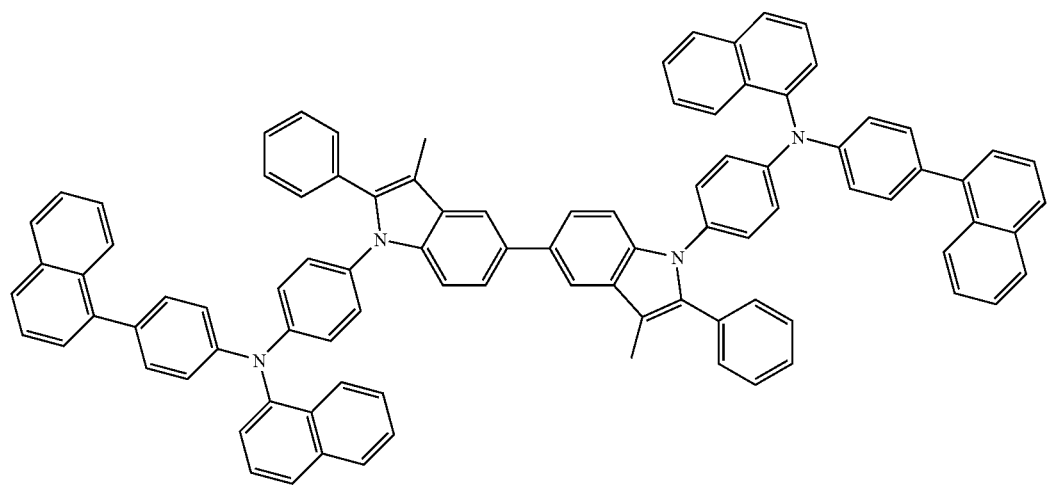

98
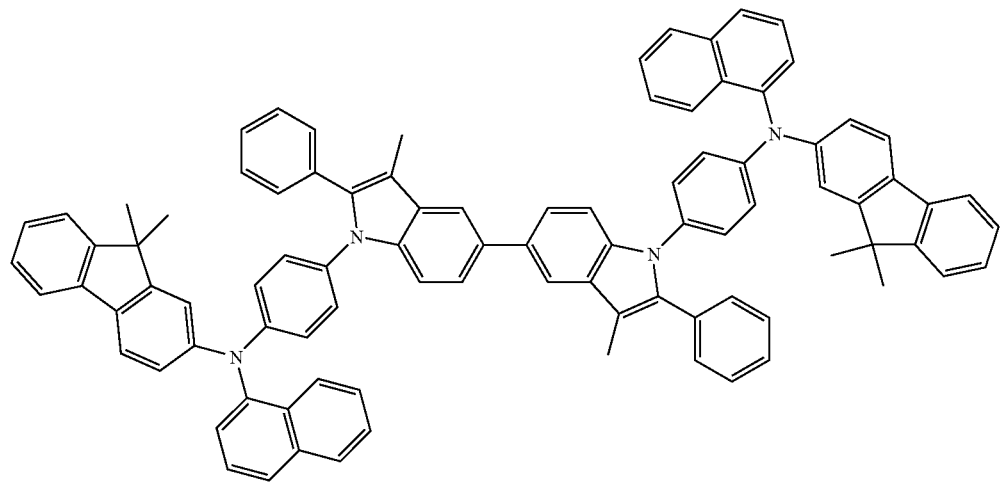
99
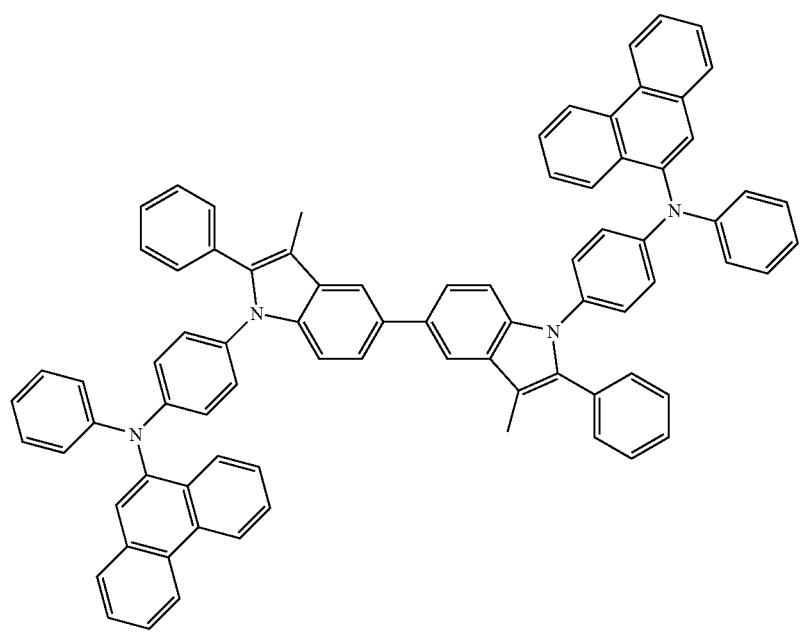

100
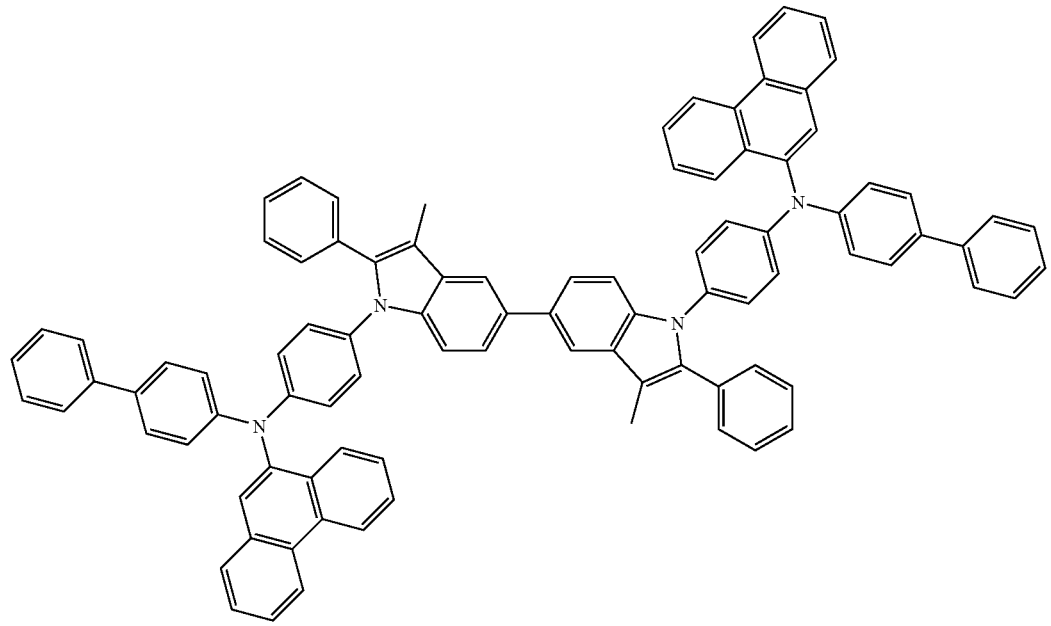
101
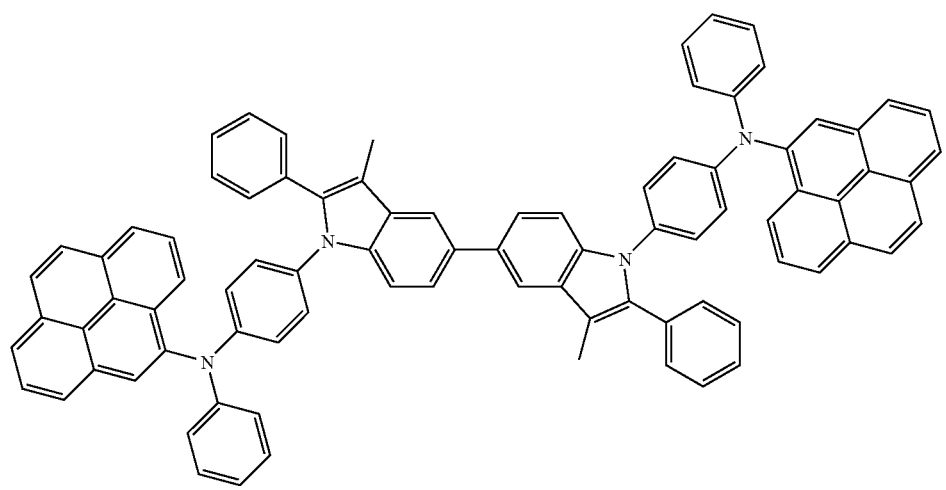
102
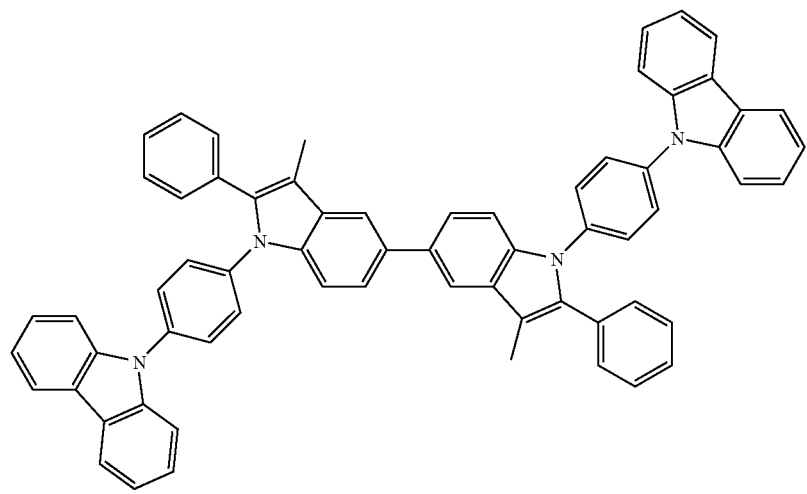

103
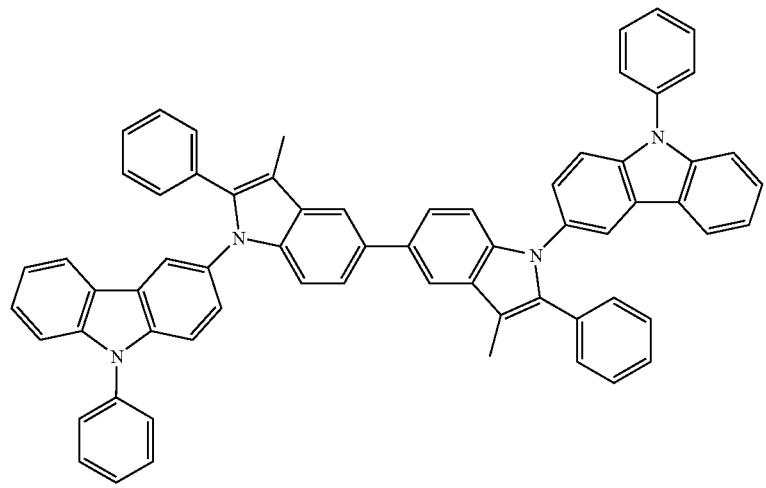
104
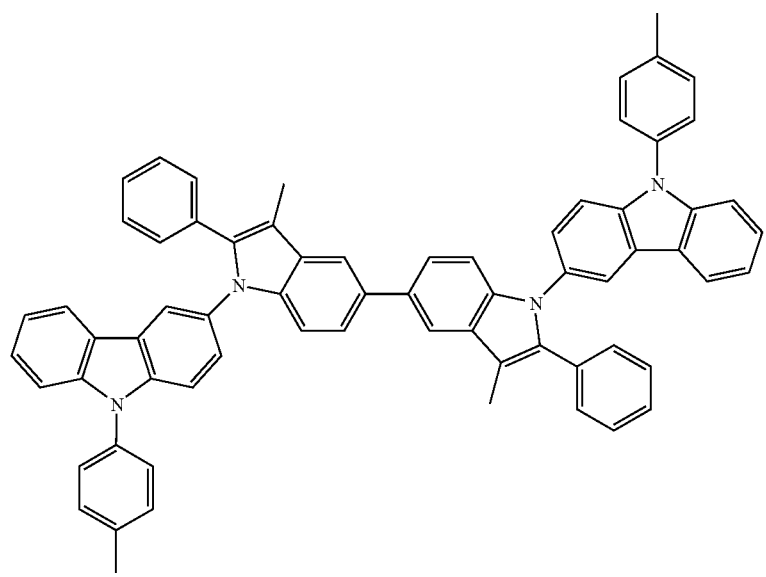
105
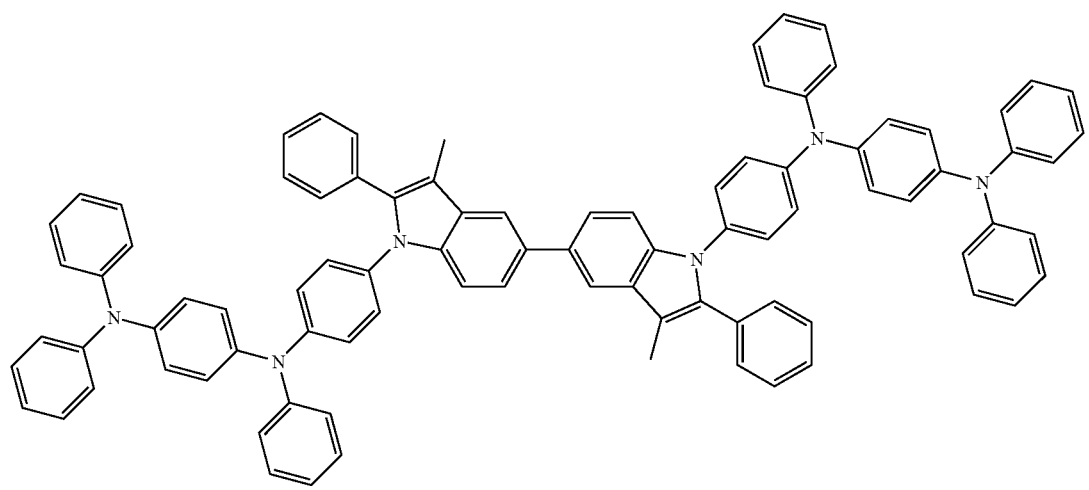

106
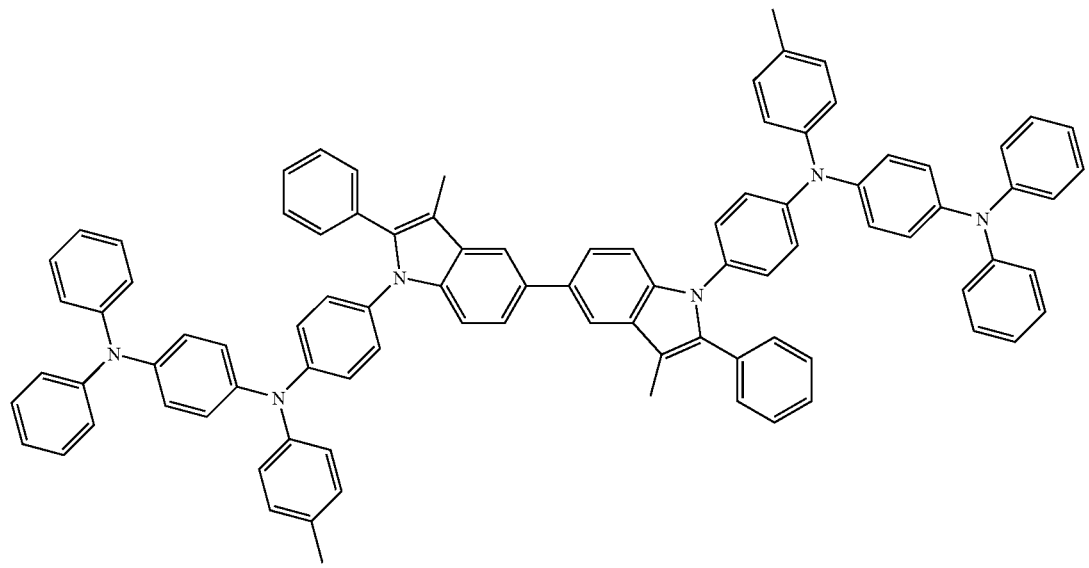
107
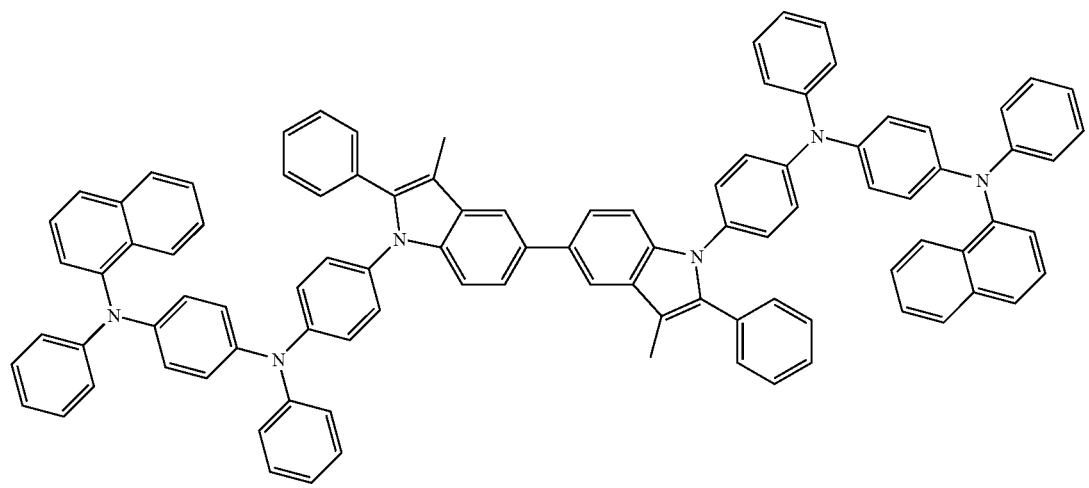
108
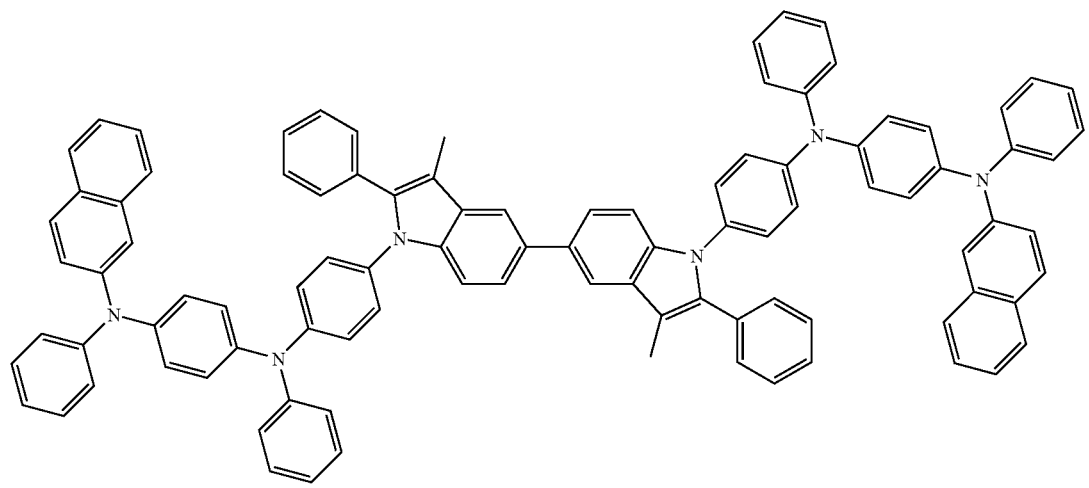

109
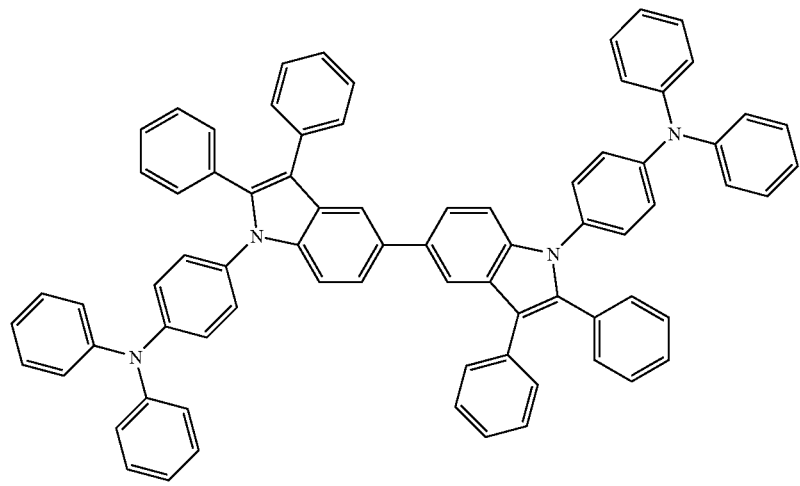
110
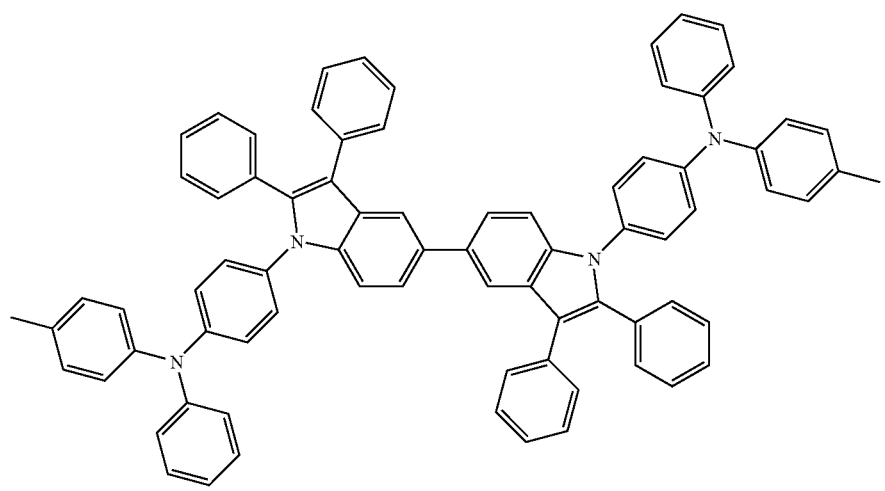
111
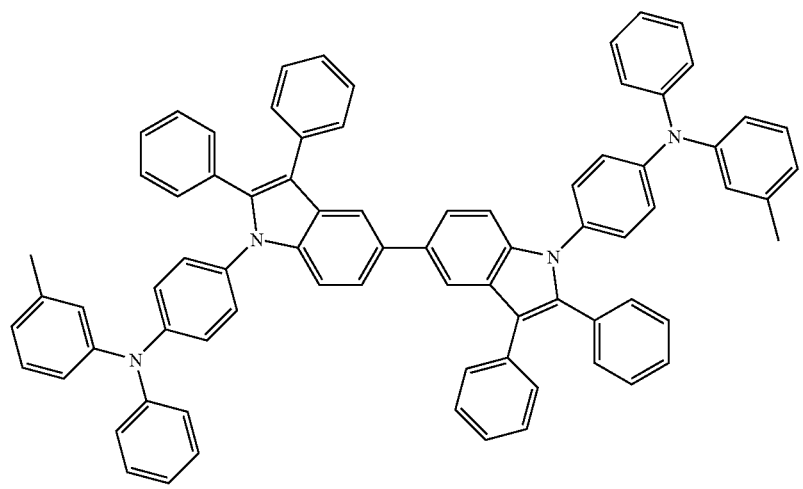

-continued
112
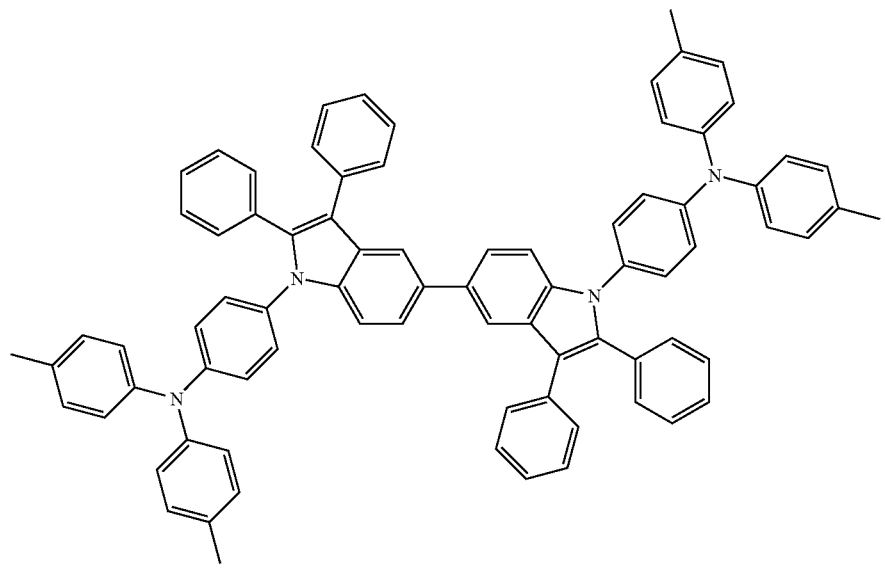
113
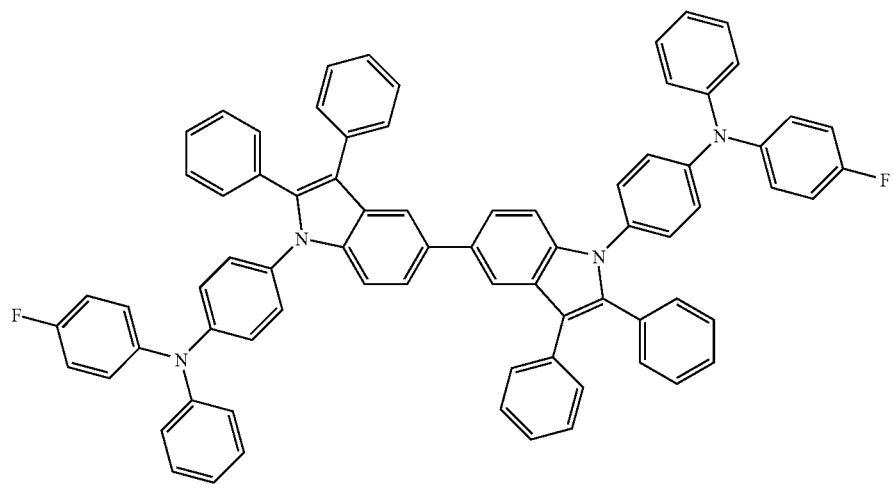
114
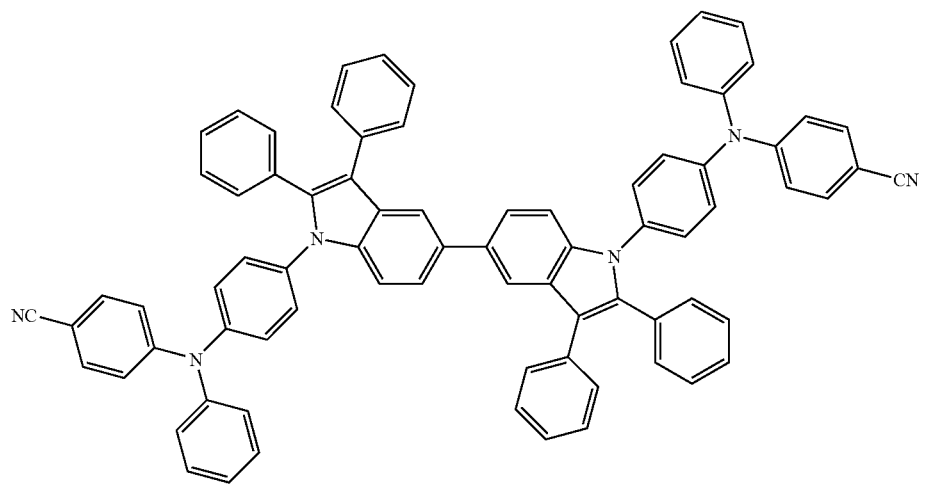

115
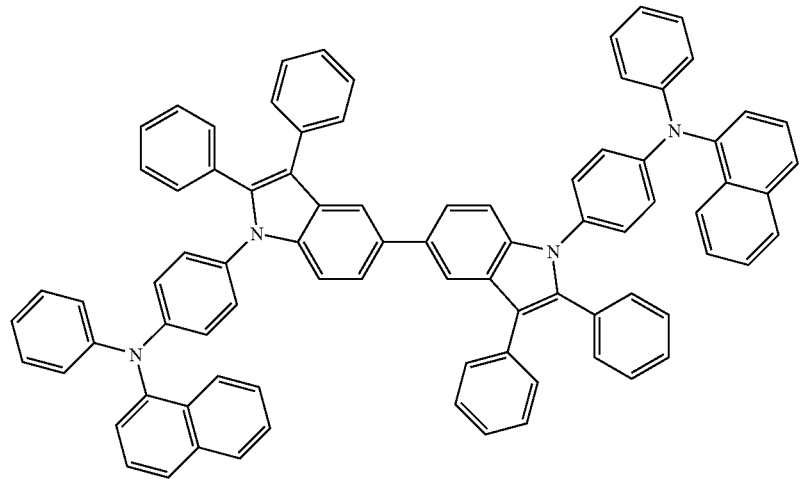
116
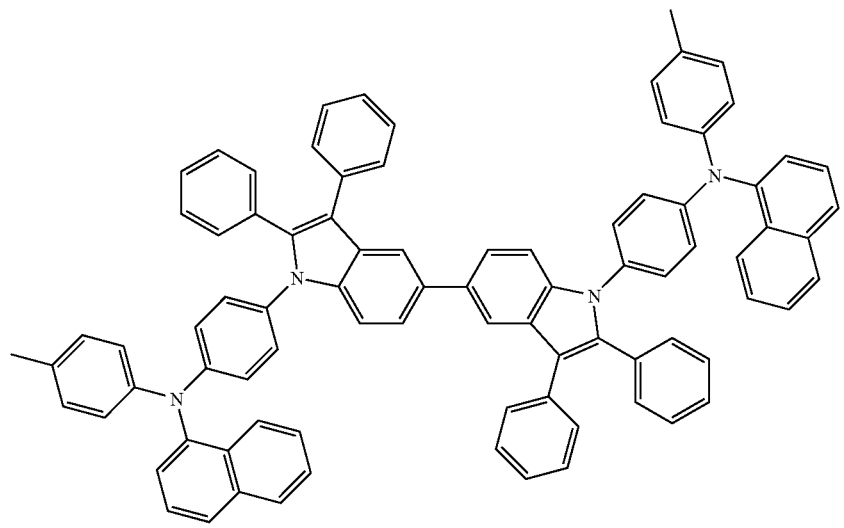
117
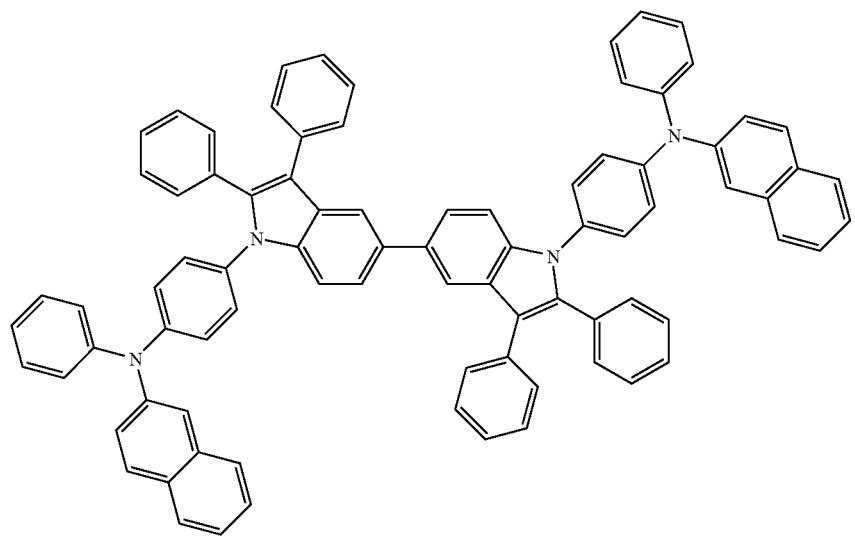

118
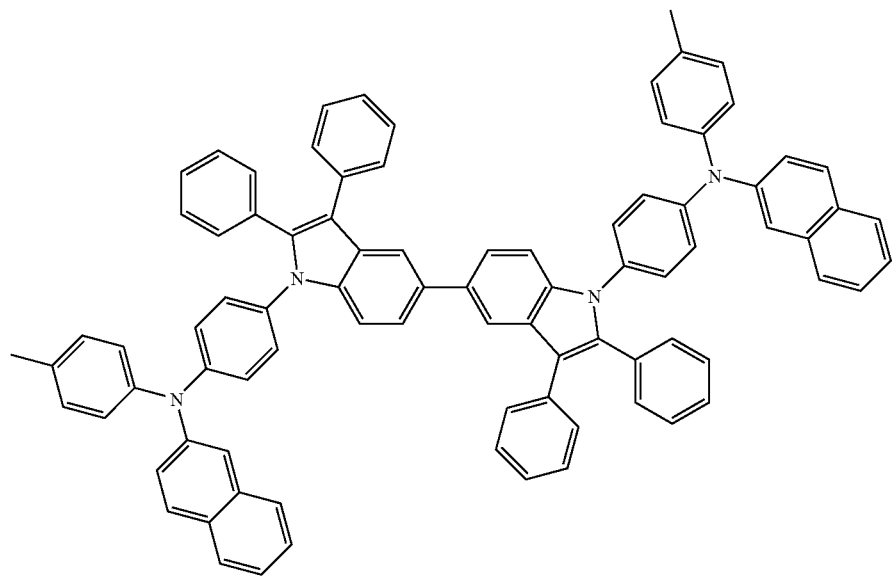
119
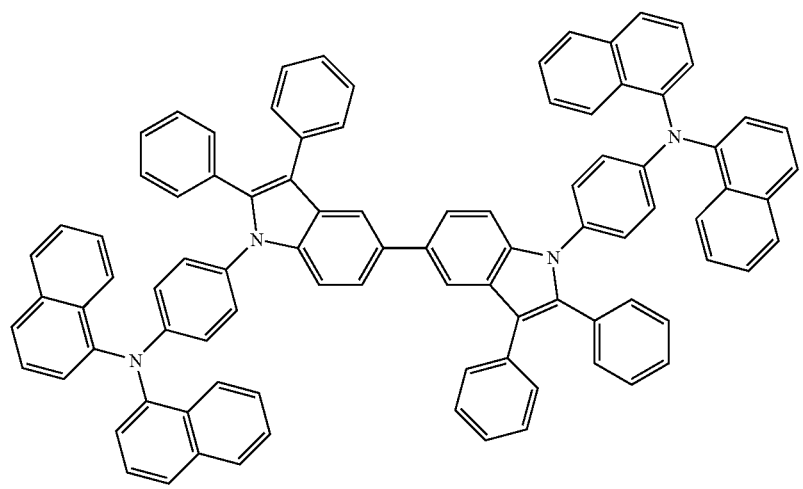

120
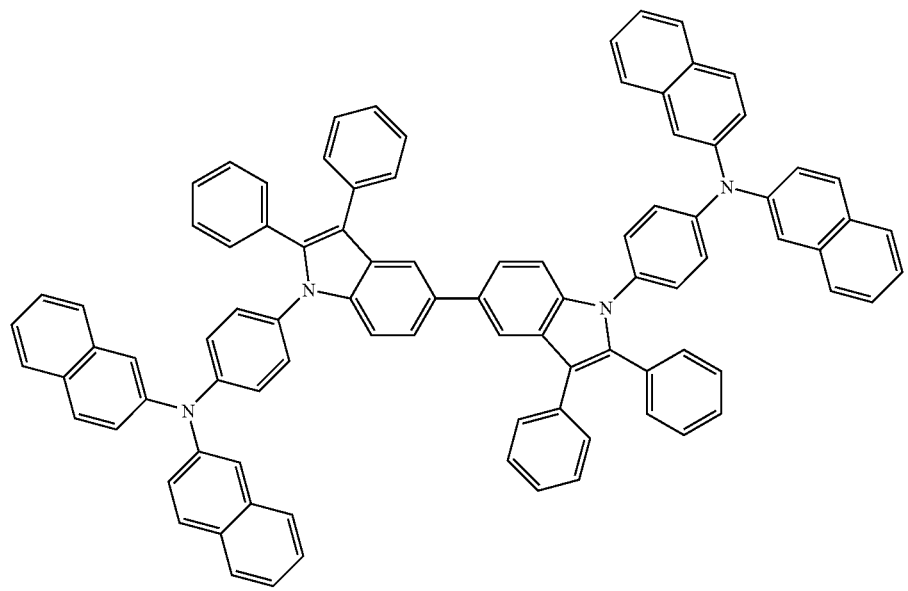
121
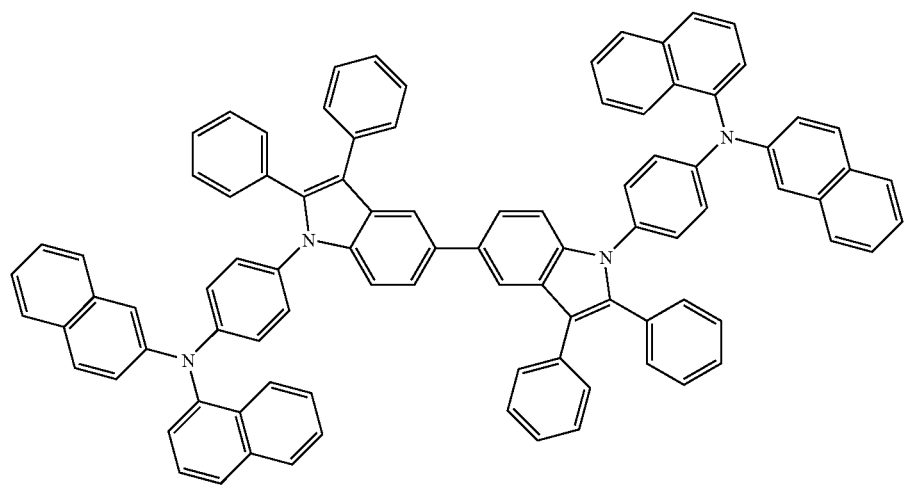
122
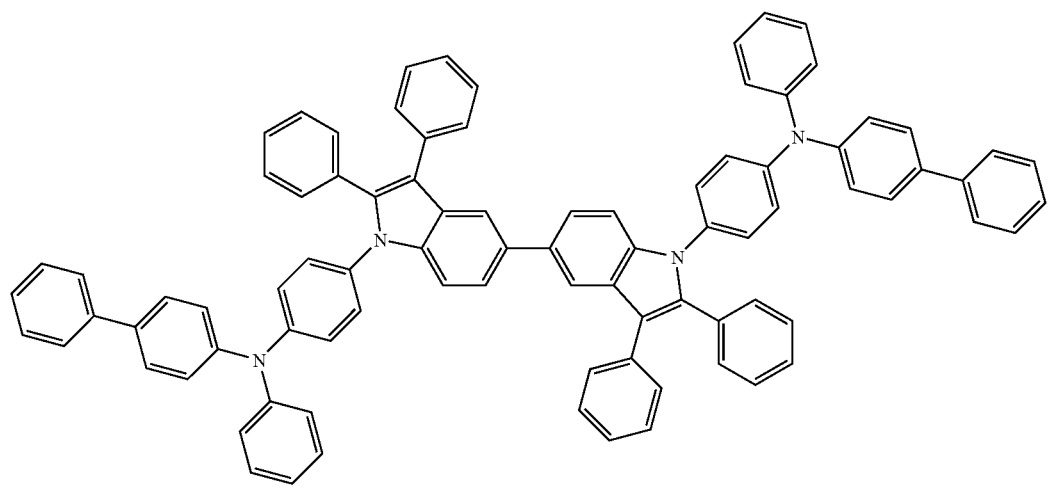

123
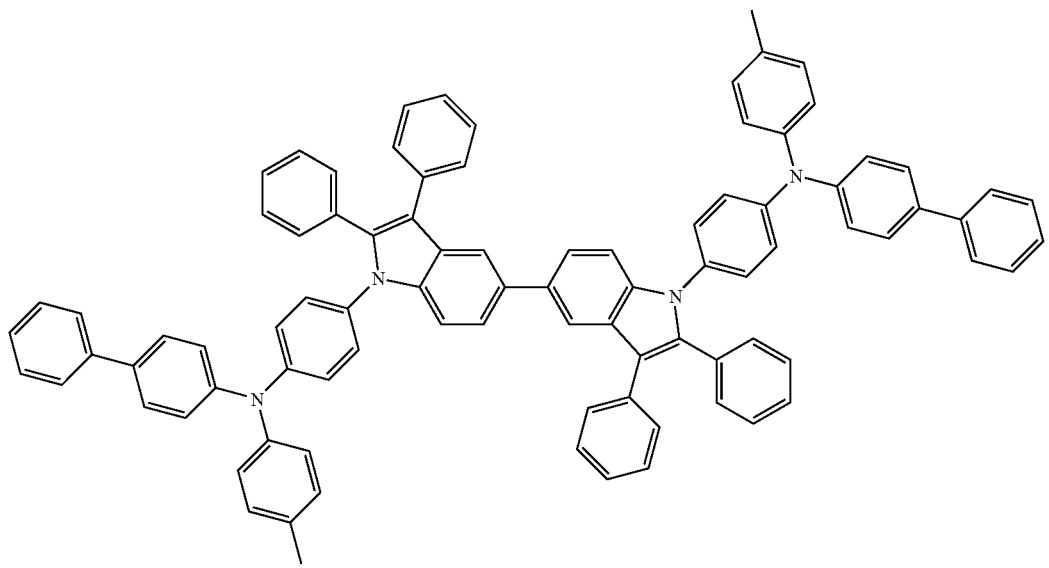
124
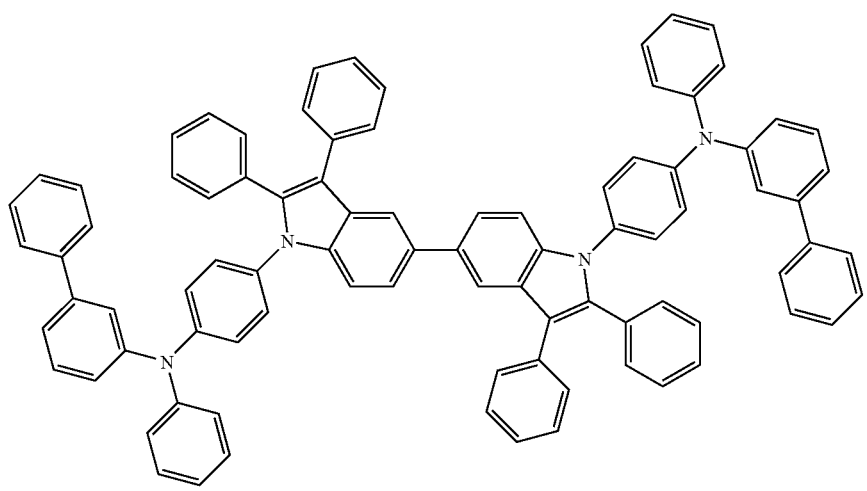

-continued
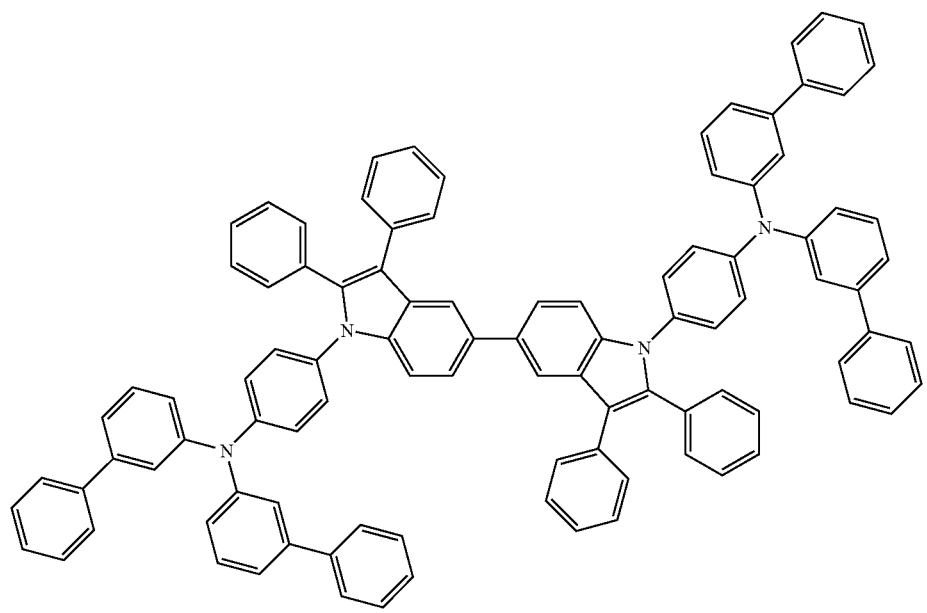
125
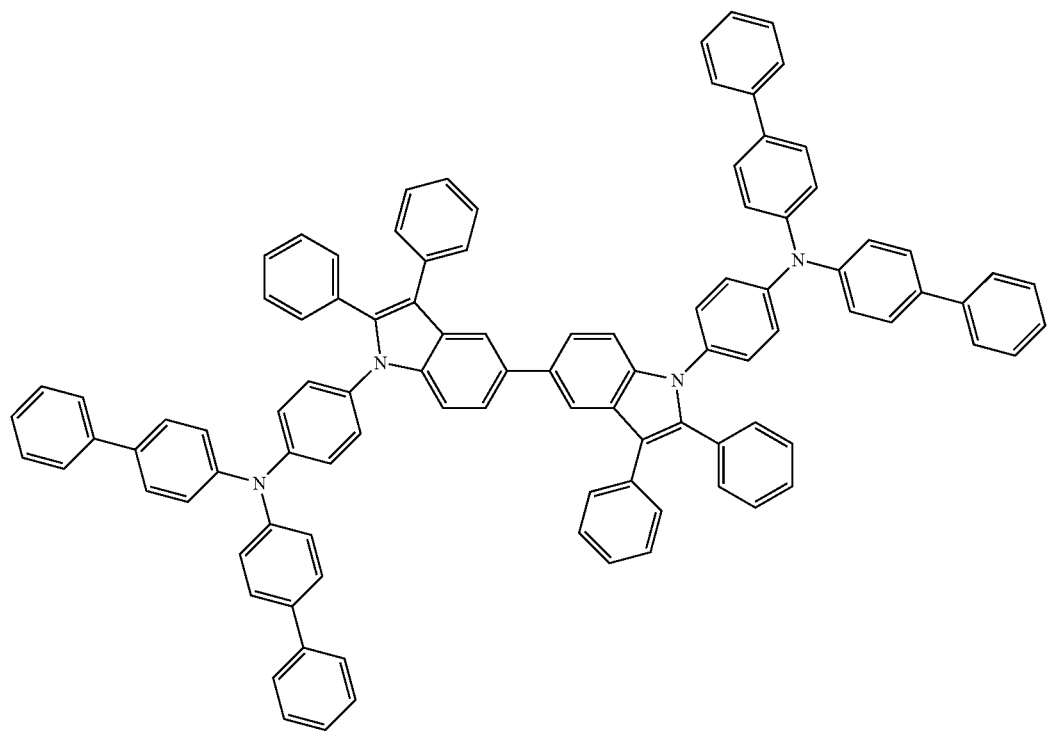
126

-continued
127
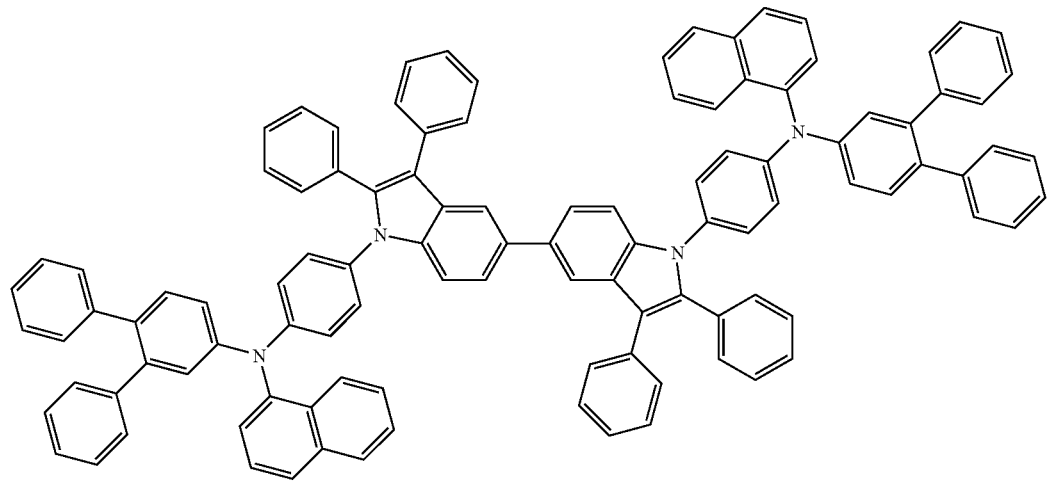
128
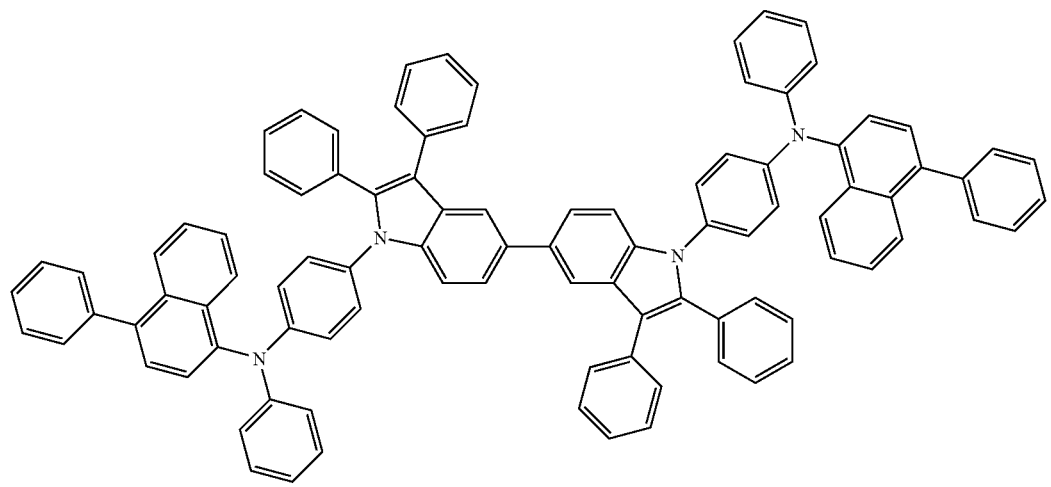
129
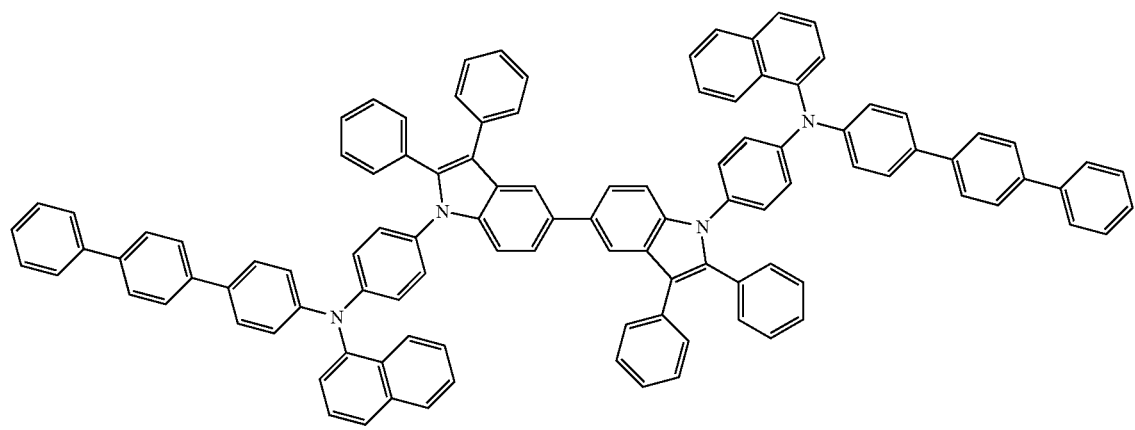

130
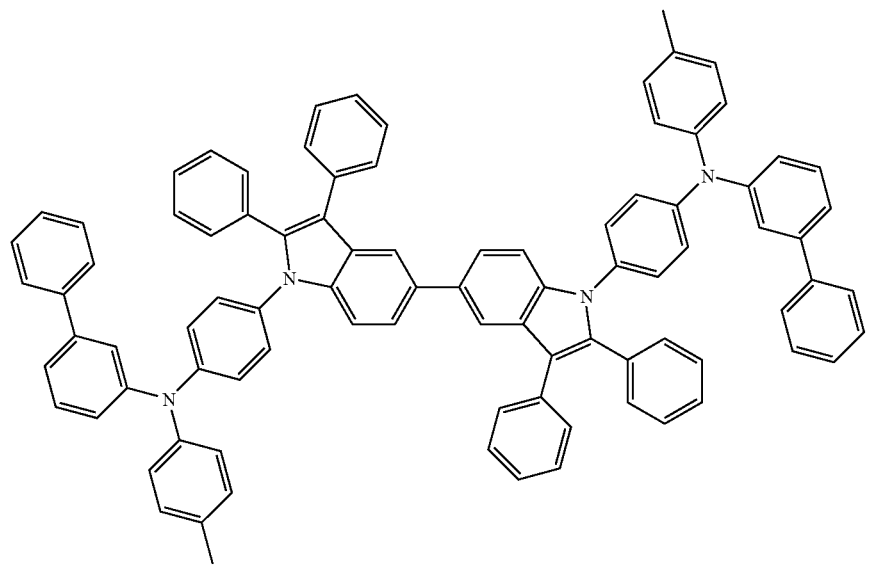
131
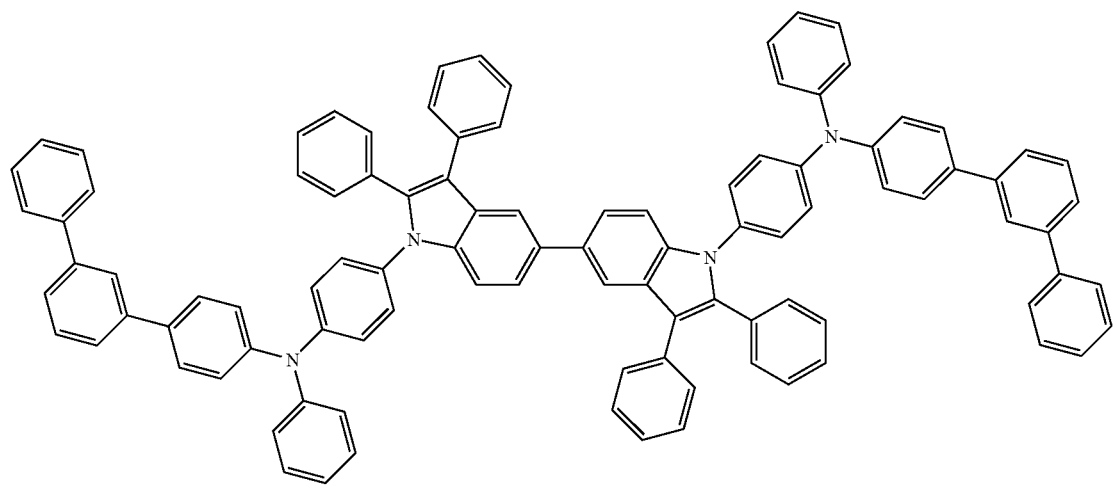
132
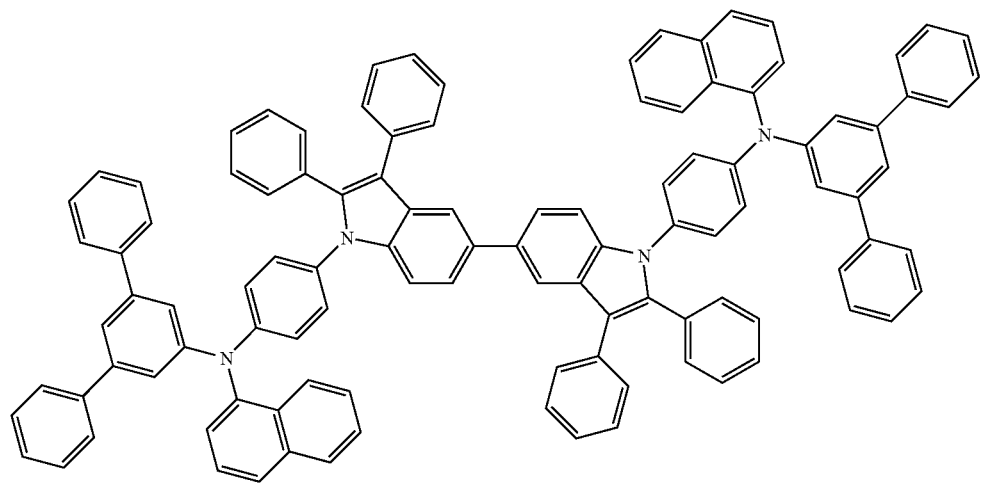

133
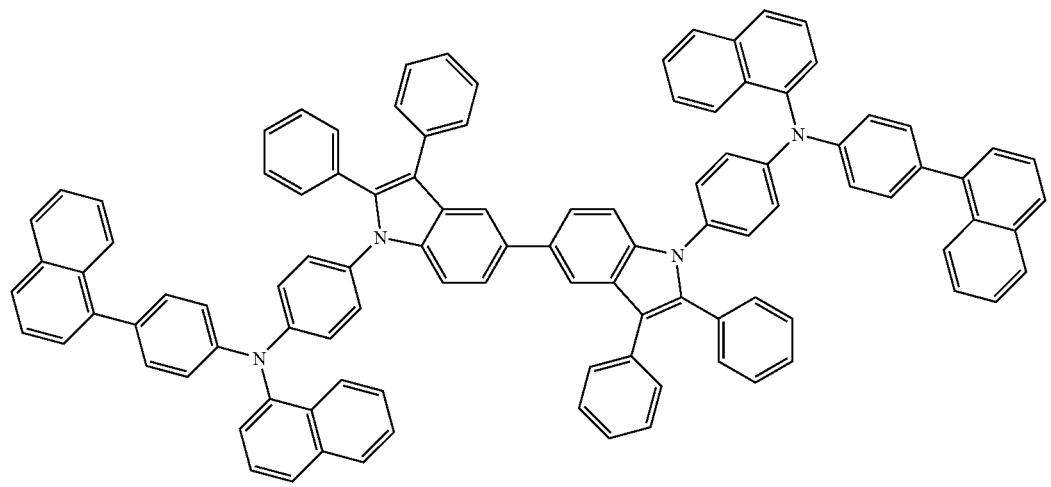
134
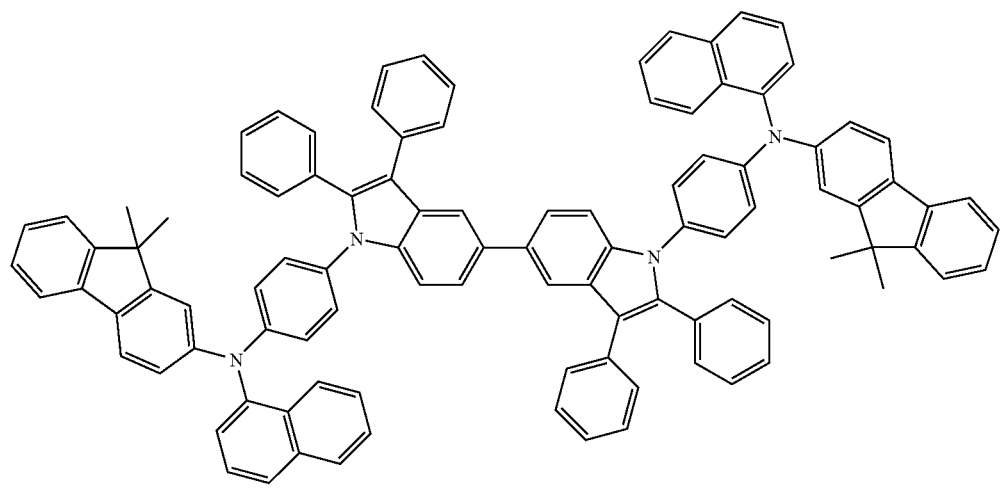
135
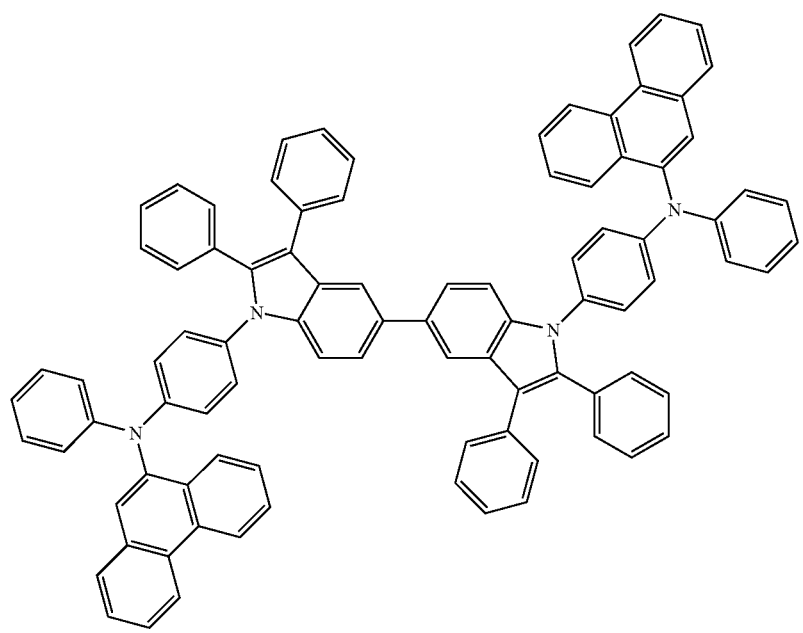

136
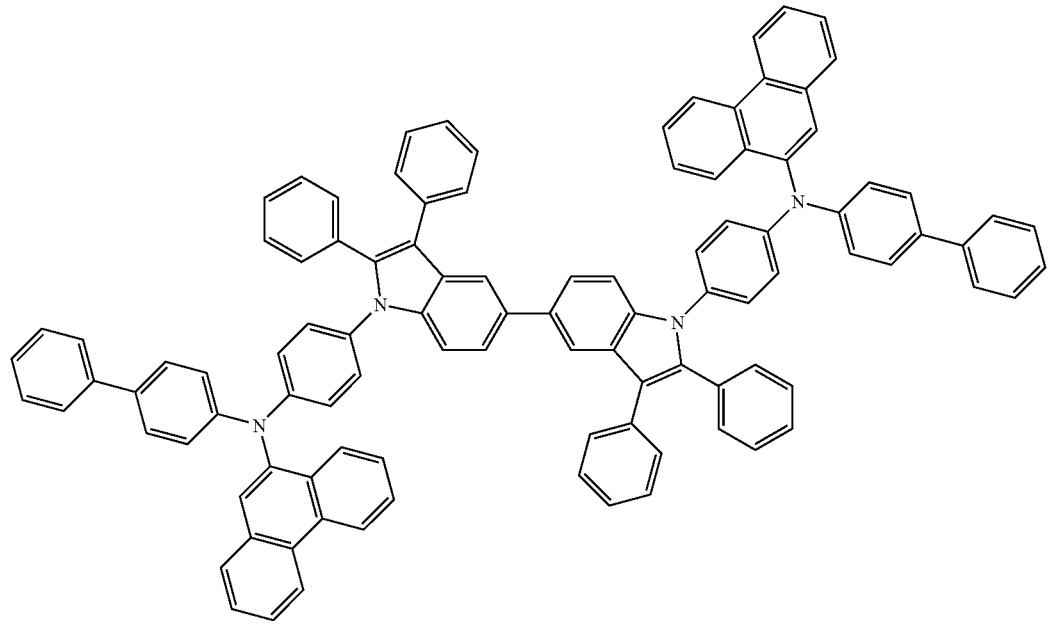
137
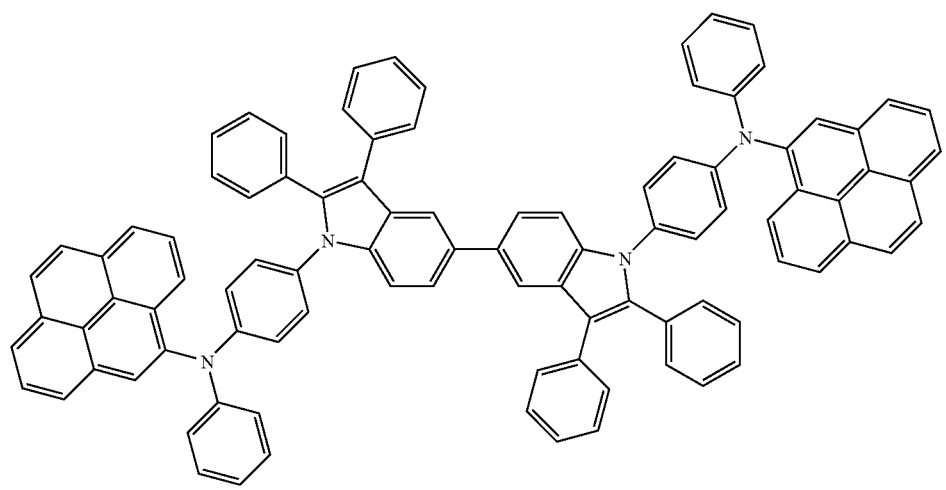
138
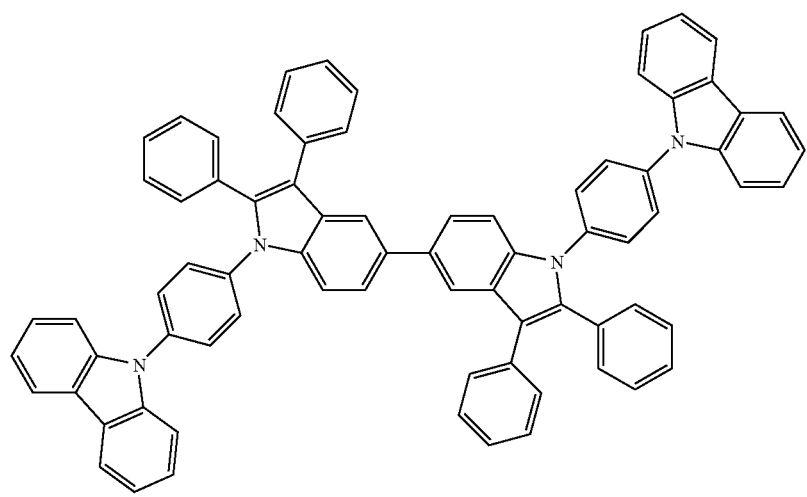

139
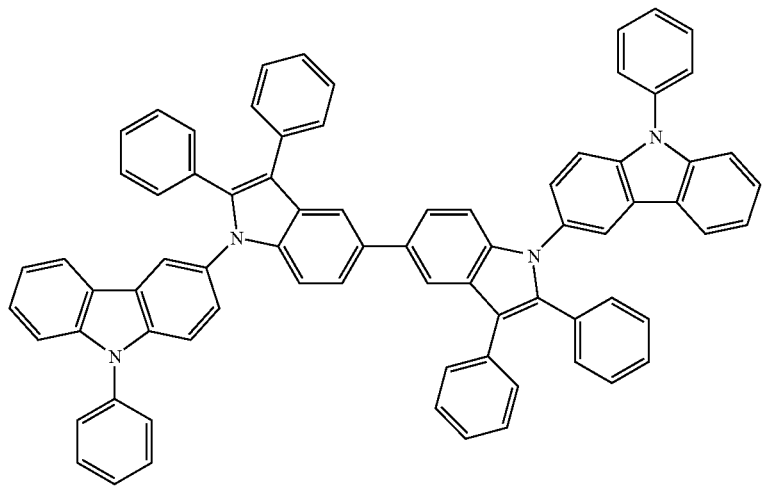
140
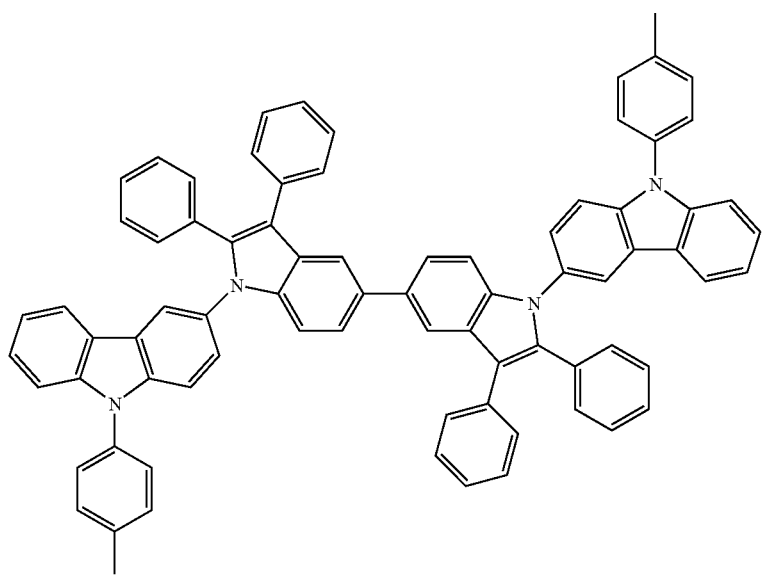
141
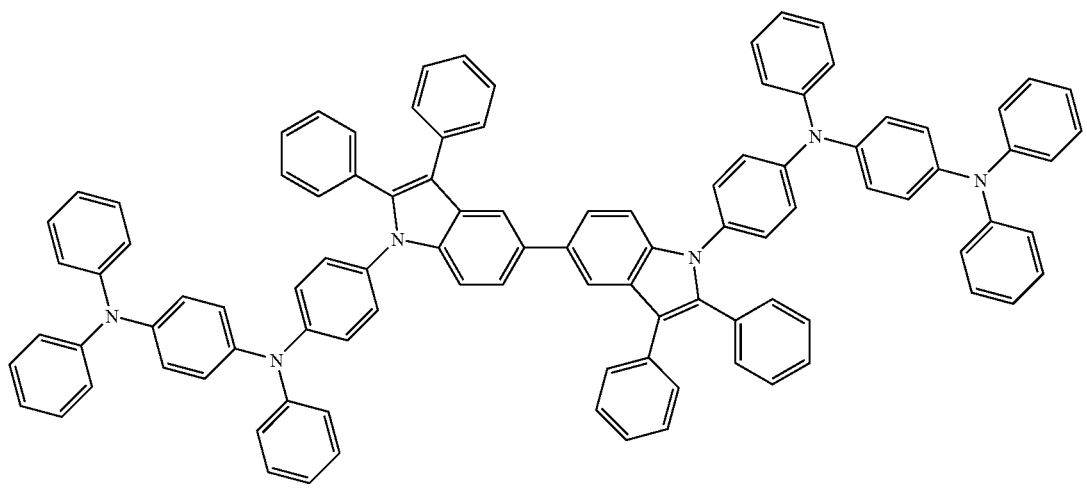

-continued
142
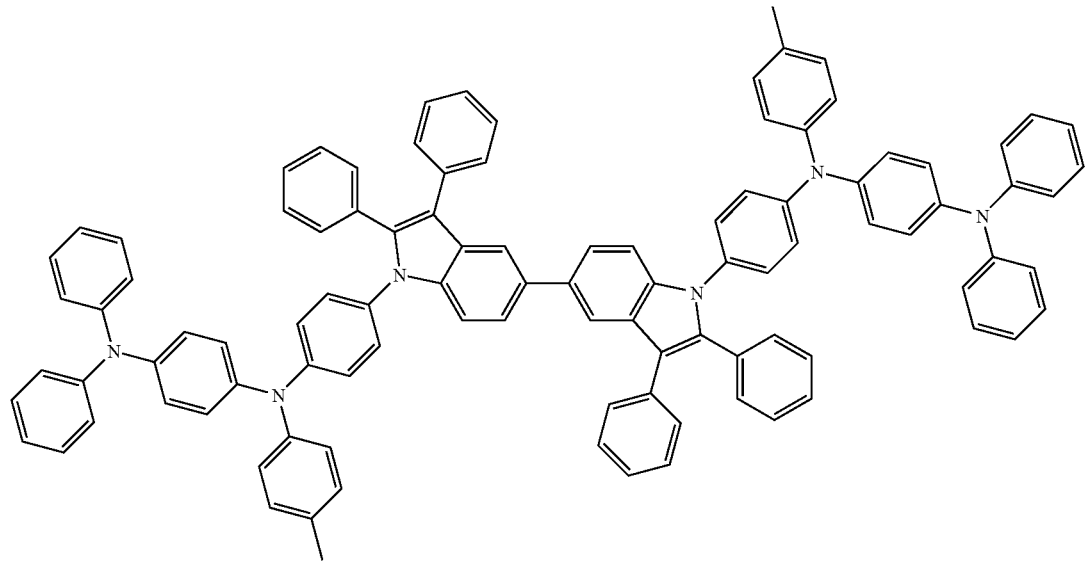
143
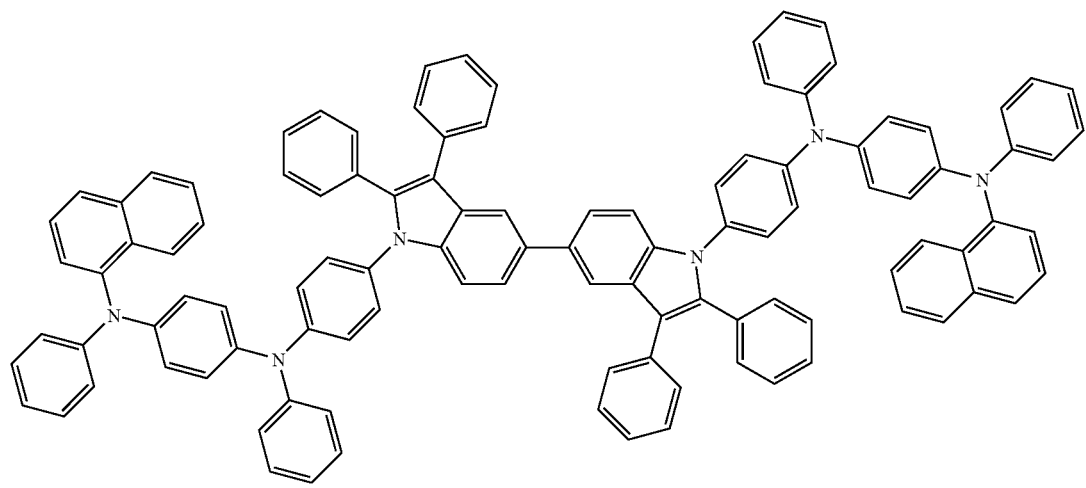
144
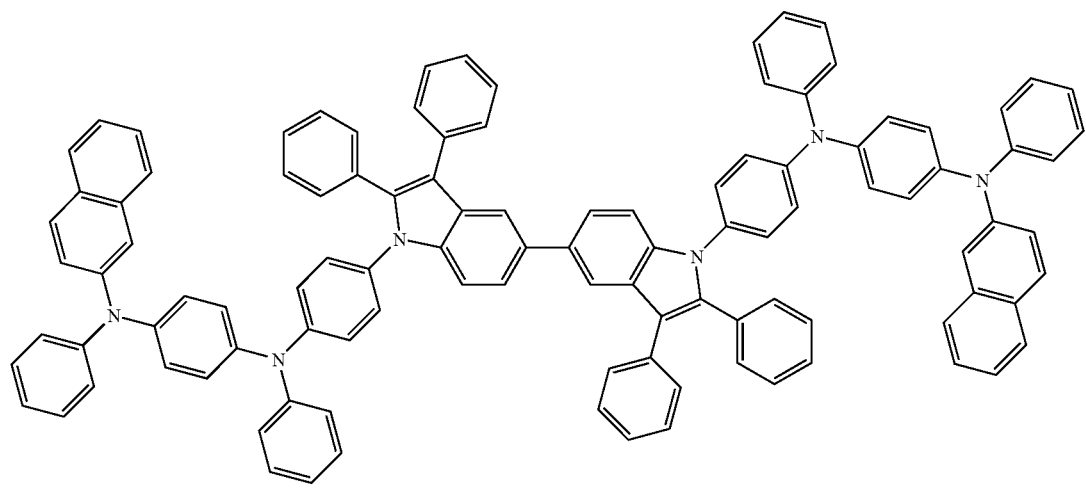

Another embodiment provides an organic electroluminescent device including a first electrode, a second electrode, and an organic layer interposed between the first electrode and the second electrode, wherein the organic layer comprises the heterocyclic compound represented by Formula 1. The heterocyclic compound of Formula 1 has excellent hole injecting properties and hole transporting properties, and thus is suitable for use as a hole transporting material, and may be used as a host material for a blue, green, or red fluorescent or phosphorescent device.

The organic electroluminescent device will now be described in detail. The organic layer comprising the heterocyclic compound of Formula 1 may be a hole injection layer, a hole transport layer, or an emitting layer, or may be a single layer having a hole injecting capability and a hole transporting capability. The heterocyclic compound of Formula 1 may be used as a host material for a blue, green, or red fluorescent or phosphorescent device.

Desirably, the organic layer comprising the heterocyclic compound of Formula 1 is a hole injection layer or a hole transport layer.

The organic electroluminescent device described above may further include at least one layer selected from a hole injection layer, a hole transport layer, an electron blocking layer, an emitting layer, a hole blocking layer, an electron transport layer, and an electron injection layer. If necessary, each of these organic layers may be a double layer.

Specifically, an organic electroluminescent device according to an embodiment may include a structure of first electrode/hole injection layer/emitting layer/second electrode, a structure of first electrode/hole injection layer/hole transport layer/emitting layer/electron transport layer/second electrode or a structure of first electrode/hole injection layer/hole transport layer/emitting layer/electron transport layer/electron injection layer/second electrode. The organic electroluminescent device may also have a structure of first electrode/a single layer having a hole injecting capability and a hole transporting capability/emitting layer/electron transport layer/second electrode or a structure of first electrode/a single layer having a hole injecting capability and a hole transporting capability/emitting layer/electron transport layer/electron injection layer/second electrode.

The organic electroluminescent device according to the present embodiments may have a variety of structures, such as a top-emission type, or a rear-emission type.

Hereinafter, a method of manufacturing an organic electroluminescent device according to an embodiment will now be described in detail with reference to an organic electroluminescent device illustrated in FIG. 1. The organic electroluminescent device illustrated in FIG. 1 includes a substrate, a first electrode(anode), a hole injection layer, a hole transport layer, an emitting layer, an electron transport layer, an electron injection layer and a second electrode(cathode).

The first electrode may be formed by depositing or sputtering a first electrode forming material having a high work function on the substrate. The first electrode may be an anode or a cathode. In this regard, the substrate may be any substrate that is used in a conventional organic electroluminescent device. For example, the substrate may be a glass or transparent plastic substrate that has mechanical strength, thermal stability, a flat surface, and convenience for handling, and is transparent and waterproof The first electrode forming material may be a highly-conductive material, such as indium tin oxide (ITO), indium zinc oxide (IZO), thin oxide ($SnO_2$), zinc oxide (ZnO), Al, Ag, or Mg, etc. and the first electrode may be a transparent electrode or a reflective electrode.

The hole injection layer (HIL) may be formed on the first electrode using a vacuum-deposition method, a spin-coating method, a casting method, or a Langmuir-Blodgett (LB) deposition method.

If the HIL is formed using the vacuum-deposition method, deposition conditions may differ according to a HIL forming material, the target layer structure, and thermal characteristics. In this regard, in general, the deposition temperature may be 100 to 500° C., a degree of a vacuum may be $10^{-8}$ to $10^{-3}$ torr, the deposition rate may be 0.01 to 100 Å/sec, and the thickness of the HIL may be 10 Å to 5 µm.

If the HIL is formed using the spin-coating method, coating conditions may differ according to the HIL forming material, the target layer structure, and thermal characteristics. In this regard, in general, the coating rate may be about 2000 rpm to 5000 rpm, and the heat treatment temperature at which a solvent used is removed after the coating may be about 80° C. to 200° C.

The HIL forming material may be the heterocyclic compound represented by Formula 1 described above. The HIL forming material may also be any known hole injecting material. Examples of the known HIL forming material include phthalocyanine compounds such as copper phthalocyanine disclosed in U.S. Pat. No. 4,356,429, starburst type amine derivatives such as TCTA, m-MTDATA, or m-MTDAPB disclosed in Advanced Material, 6, p. 677(1994), and soluble conductive polymers such as polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA) or (polyaniline)/poly(4-styrenesulfonate) (PANI/PSS).

The thickness of the HIL may be about 100 Å to 10000 Å, specifically 100 Å to 1000 Å. If the thickness of the HIL is less than 100 Å, hole injecting characteristics may be degraded. On the other hand, if the thickness of the HIL is greater than 10000 Å, the driving voltage may be increased.

The hole transport layer (HTL) may be formed on the HIL using any known method, such as a vacuum-deposition method, a spin-coating method, a casting method, or a LB deposition method. When the HTL is formed using the vacuum-deposition method or the spin-coating method, deposition conditions and coating conditions may differ according to a HTL forming material. In this regard, deposition conditions and coating conditions may be almost the same as those described with reference to the HIL.

The HTL forming material may be the heterocyclic compound represented by Formula 1 described above. The HTL forming material may also be any known HTL forming material. Examples of the known HTL forming material include carbazole derivatives such as N-phenylcarbazole or polyvinylcarbazole, and amine derivatives having an aromatic condensation ring, such as 4,4'-bis[N-(1-naphthyl)-N-phenylamino]biphenyl(NPB), N,N'-bis(3-methylphenyl)-N,N'-diphenyl-[1,1-biphenyl]-4,4'-diamine(TPD), or N,N'-di(naphthalene-1-yl)-N,N'-diphenyl benzidine(α-NPD).

The thickness of the HTL may be about 50 Å to 1000 Å, specifically 100 Å to 600 Å. If the thickness of the HTL is less than 50 Å, hole transporting characteristics may be degraded. On the other hand, if the thickness of the HTL is greater than 1000 Å, the driving voltage may be increased.

Then, the emitting layer (EML) may be formed on the HTL using any known method, such as a vacuum-deposition method, a spin-coating method, a casting method, or a LB deposition method. When the EML is formed using the vacuum-deposition method or the spin-coating method, deposition conditions and coating conditions may differ according to an EML forming material. In this regard, in general, deposition conditions and coating conditions may be almost the same as those described with reference to the HIL.

The EML may comprise the heterocyclic compound represented by Formula 1 described above. In particular, the heterocyclic compound of Formula 1 may be used as a host of the EML. The EML may be formed using various known luminescent materials, such as known hosts and dopants. For the dopants, known fluorescent dopants and known phosphorescent dopants all can be used to form the EML.

Examples of the host include $Alq_3$, 4,4'-N,N'-dicarbazole-biphenyl (CBP), poly(n-vinylcarbazole) (PVK), and distyrylarylene (DSA). However, the host is not limited to those materials.

With respect to dopants, examples of fluorescent dopants include DPVBi, a C-545T, and DCJTB, and examples of phosphorescent dopants include $Ir(ppy)_3$ where ppy is an abbreviation of phenylpyridine (green), $(4,6-F2ppy)_2Irpic$ (see Chihaya Adachi etc. *Appl. Phys. Lett.,* 79, 2082-2084, 2001), TEB002 produced by (Covion), platinum(II) octaethylporphyrin (PtOEP), a compound represented by Formula 3 (see KR Patent Publication No. 2005-0078472), Firpric, and RD 61 that is a red phosphorescent dopant produced by UDC Co. However, dopants are not limited to those materials.

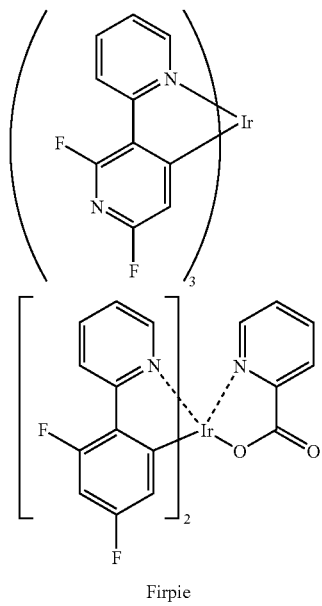

Formula 3

Firpie

The amount of the dopant may be 0.1 to 20 parts by weight, specifically 0.5 to 12 parts by weight based on 100 parts by weight of the EML forming material (that is, the total weight of the host and dopant is set at 100 parts by weight). If the amount of the dopant is less than 0.1 parts by weight, the dopant-addition-effect is insignificant. On the other hand, if the amount of the dopant is greater than 20 parts by weight, in both phosphorescent and fluorescent cases, concentration quenching may occur.

The thickness of the EML may be about 100 Å to about 1000 Å, preferably from about 200 Å to about 600 Å.

When the EML is formed using a phosphorescent dopant, diffusion of triplet exitons or holes into the ETL can be prevented by forming a hole blocking layer (HBL) (not shown in FIG. 1) on the EML. In this case, an available HBL forming material is not limited and may be selected from known HBL forming materials. Examples of the HBL forming material include an oxadiazole derivative, a triazole derivative, a phenanthroline derivative, a hole blocking material disclosed in JP 11-329734(A1), Balq, and BCP.

The thickness of the HBL may be about 50 Å to about 1000 Å, preferably from about 100 Å to about 300 Å.

Then, the electron transport layer (ETL) may be formed using any known method, such as a vacuum-deposition method, a spin-coating method, or a casting method. When the ETL is formed using the vacuum-deposition method or the spin-coating method, deposition conditions and coating conditions may differ according to an ETL forming material. In this regard, in general, deposition conditions and coating conditions may be almost the same as those described with reference to the HIL.

The ETL forming material is not limited and may be selected from known ETL forming materials. Examples of the ETL forming material include quinoline derivatives, such as tris(8-quinolinolate)aluminum ($Alq_3$) or TAZ.

The thickness of the ETL may be about 100 Å to about 1000 Å, preferably from about 100 Å to about 500 Å.

In addition, an electron injection layer (EIL) that allows electrons to be easily injected from an anode may be formed on the ETL.

The EIL may be formed using any known EIL forming material, such as LiF, NaCl, CsF, $Li_2O$, or BaO. The deposition conditions and coating conditions of the EIL may differ according to the EIL forming material. In general, however, the deposition conditions and coating conditions may be almost the same as those described with reference to the HIL.

The thickness of the EIL may be about 1 Å to 100 Å, specifically 5 Å to 90 Å. If the thickness of the EIL is less than 1 Å, electron injecting characteristics may be degraded. On the other hand, if the thickness of the EIL is greater than 100 Å, the driving voltage may be increased.

Finally, the second electrode is formed on the EIL using a vacuum-deposition method or a sputtering method. The second electrode may function as a cathode or an anode. The second electrode may be formed using metal, alloy, an electrically conductive compound, or mixtures thereof, each of which has a low work function. Examples of such materials include lithium (Li), magnesium (Mg), aluminum (Al), aluminum-lithium (Al—Li), calcium (Ca), magnesium-indium (Mg—In), and magnesium-silver (Mg—Ag). In addition, to produce a top emission type display device, the second electrode may be formed using a transparent material such as ITO or IZO.

The organic electroluminescent device according to the present embodiments may be included in various types of flat panel devices, such as passive matrix organic light emitting display devices or active matrix organic light emitting display devices. Specifically, when the organic electroluminescent device according to the present embodiments is used in active matrix organic light emitting display devices, the first electrode disposed on a substrate side may function as a pixel electrode and may be electrically connected to a source electrode or drain electrode of a thin film transistor. In addition, the organic electroluminescent device according to the present embodiments may also be used in a flat panel display device that includes screens on opposite sides.

Hereinafter, synthesis examples and examples of the heterocyclic compound represented by Formula 1 will be described in detail. However, the present embodiments will not be limited to those examples.

EXAMPLES
Synthesis Example 1
Preparation of Compound 1
Compound 1 was synthesized through a reaction pathway illustrated in Reaction Scheme 1 below.
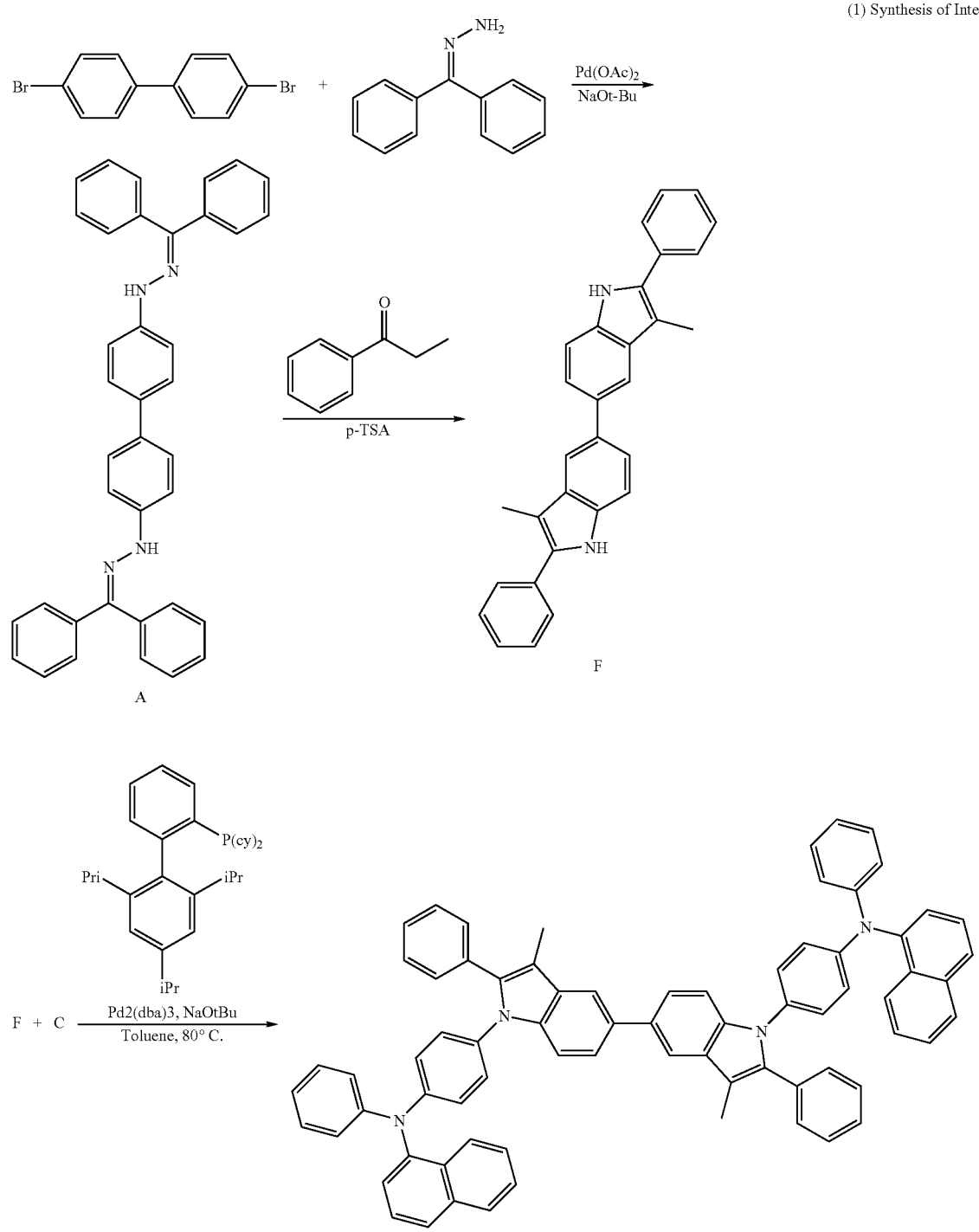
(1) Synthesis of Intermediate A 31.2 g of dibromo biphenyl (0.10 mole) and 43.2 g of benzophenone hydrazone (0.22 mole) were dissolved in 400 ml of toluene. Then, 1.12 g of Pd(OAc)$_2$ (5.0 mole %), 2.6 g of phosphine ligand (5.5 mole), and 28.8 g of NaOtBu (0.30 mole) were added to the mixture and the resultant mixture was stirred while refluxing for 12 hours in a nitrogen atmosphere. After the reaction was terminated, methylene chloride was added to the reaction solution at room temperature and the resultant solution was filtered using cellite. The solution was then extracted using 50 ml of ethylether three times. The collected organic layer was dried over magnesium sulfate and a solvent was evaporated to obtain the residue. The residue was purified by silicagel column chromatography to obtain 4.21 g (yield 85%) of a white solid Intermediate A.

$^1$H NMR (CD2Cl2, 400 MHz) δ (ppm) 7.52-7.63 (m, 8H), 7.46 (d, 4H), 7.27-7.35 (m, 10H), 7.12 (d, 4H); $^{13}$C NMR (CD2CL2, 100 MHz) δ (ppm) 190.8, 133.2, 132.5, 130.5, 129.8, 129.3, 128.2, 128.0, 127.2, 126.5, 113.3.

(2) Synthesis of Intermediate B 10.8 g of the prepared Intermediate A (20.0 mmole) and 15.2 g of p-toluenesulfonic acid monohydrate (80.0 mmole) were added to 150 ml of methylethylketone, and the mixture was stirred while refluxing for 15 hours in a nitrogen atmosphere. After the reaction was terminated, water was added to the reaction solution and the resultant solution was extracted using 150 ml of methylene chloride three times. The collected organic layer was dried over magnesium sulfate and a solvent was evaporated to obtain the residue. The residue was purified by silicagel column chromatography to obtain 3.7 g (yield 65%) of a light brown solid Intermediate B.

$^1$H NMR (DMSO-d6, 400 MHz) δ (ppm) 11.6 (s, 2H), 7.23-7.45 (m, 6H), 2.39, (s, 3H), 2.30 (s, 3H); $^3$C NMR (DMSO-d6, 100 MHz) δ (ppm) 127.5, 126.7, 122.7, 122.3, 121.5, 120.6, 116.7, 109.9, 11.1, 8.9.

(3) Synthesis of Compound 1

3.64 g of Intermediate B (12.0 mmole), 8.56 g of 4-bromophenyl-diphenyl amine (26.4 mmole), 220 mg of Pd$_2$dba$_3$ (2.0 mole %), 95 mg of phosphine ligand (2.0 mole %), and 3.46 g of NaOtBu (36.0 mmole) were added to 80 ml of toluene, and then the mixture was stirred while refluxing for 8 hours in a nitrogen atmosphere. After the reaction was terminated, water was added to the reaction solution and the resultant solution was extracted using 200 ml of methylene chloride twice. The collected organic layer was dried over magnesium sulfate and a solvent was evaporated to obtain the residue. The residue was purified by silicagel column chromatography to obtain 6.0 g (yield 65%) of a white solid Compound 1.

$^1$H NMR (CD2Cl2, 400 MHz) δ (ppm) 7.80 (d, 2H), 7.74 (d, 2H), 7.38-7.53 (m, 10H), 7.1-7.27 (m, 18H), 6.90 (t, 2H), 2.34 (s, 6H), 2.24 (s, 6H); $^{13}$C NMR (CD2Cl2, 100 MHz) δ (ppm) 147.9, 147.6, 136.5, 135.3, 134.1, 133.5, 129.2, 128.5, 126.4, 126.1, 124.3, 122.1, 122.0, 116.6, 109.6, 107.5, 11.0, 8.9. 127.5, 126.7, 122.7, 122.3, 121.5, 120.6, 116.7, 109.9, 11.1, 8.9.

Synthesis Example 2

Preparation of Compound 7

Compound 7 was synthesized through a reaction pathway illustrated in Reaction Scheme 2 below.

Reaction Scheme 2

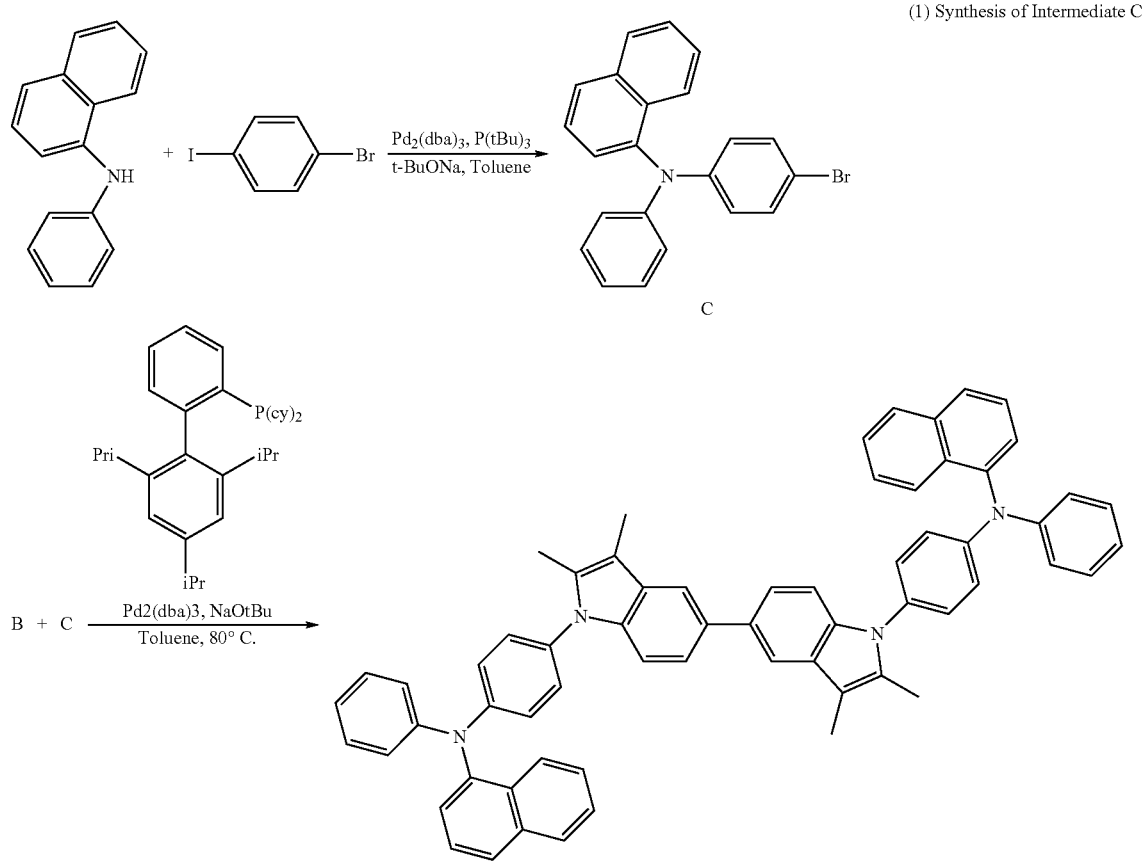

6.58 g of 1-naphthyl-phenylamine (30.0 mmole) and 12.7 g of 4-bromoiodobenzene (45.0 mmole) were dissolved in 150 ml of toluene. Then, 550 mg of Pd$_2$dba$_3$ (2.0 mole %), 300 mg of phosphine ligand (2.0 mole %), and 4.32 g of NaOtBu (45.0 mole) were added to the mixture and the resultant mixture was stirred while refluxing for 4 hours in a nitrogen atmosphere. After the reaction was terminated, water was added to the reaction solution at room temperature and the resultant solution was extracted using 200 ml of methylene chloride twice. The collected organic layer was dried over magnesium sulfate and a solvent was evaporated to obtain the residue. The residue was purified by silicagel column chromatography to obtain 4.7 g (yield 42%) of a light yellow solid Irtermediate C.

$^1$H NMR (CD2Cl2, 400 MHz) δ (ppm) 8.10 (d, 2H), 7.91 (d, 2H), 7.80 (d, 2H), 7.74 (d, 2H), 7.1-7.55 (m, 28H), 6.90 (t, 2H), 2.31 (s, 6H), 2.21 (s, 6H); $^{13}$C NMR (CD2Cl2, 100 MHz) δ (ppm) 147.7, 147.4, 143.2, 136.5, 135.3, 134.7, 133.4, 131.4, 131.2, 129.2, 129.0, 128.5, 128.4, 127.4, 126.8, 126.5, 126.4, 126.2, 124.1, 122.4, 122.3, 121.4, 121.3, 116.4, 109.7, 107.8, 11.2, 8.9.

Synthesis Example 3

Preparation of Compound 9

Compound 9 was synthesized through a reaction pathway illustrated in Reaction Scheme 3 below.

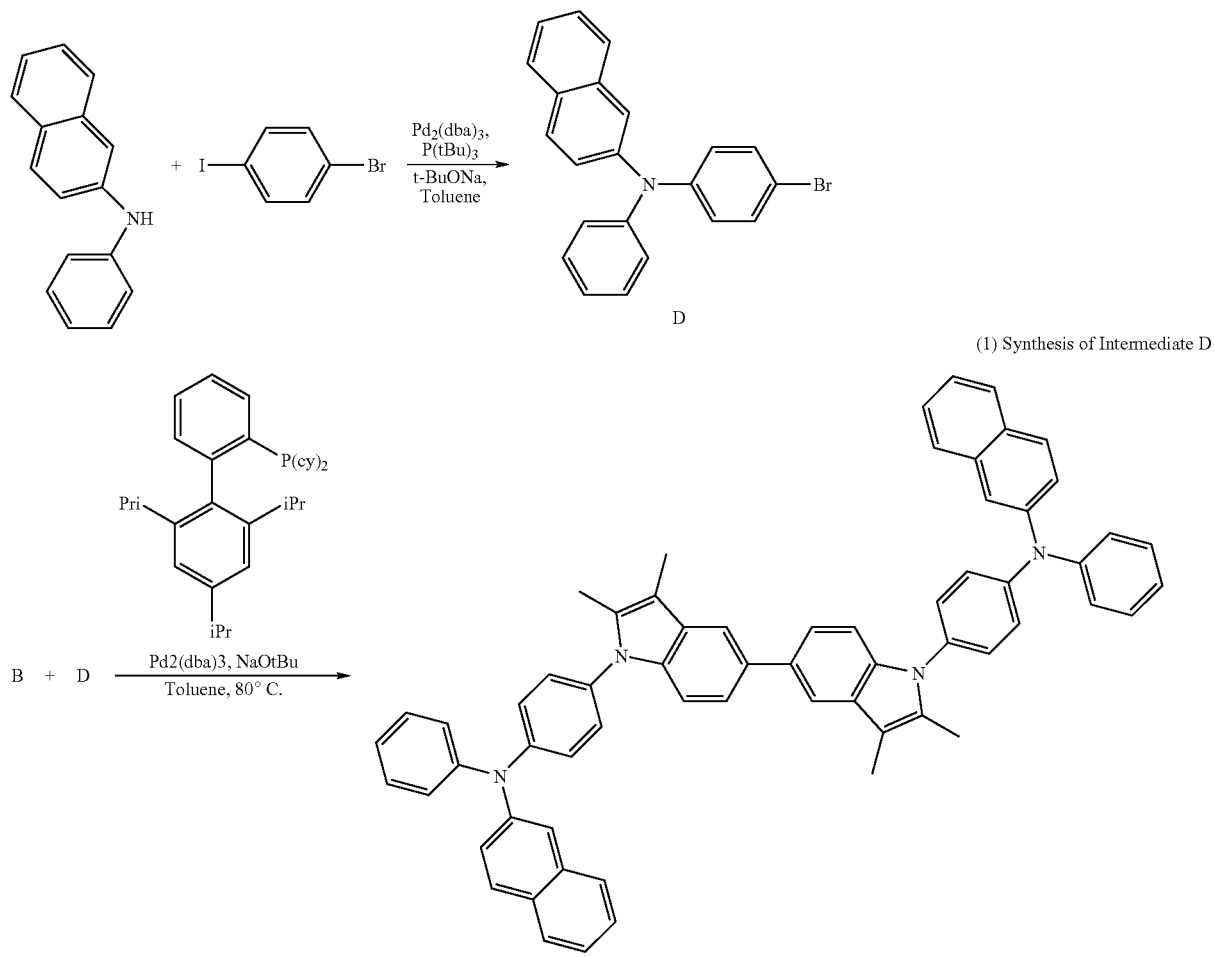

$^1$H NMR (CD2Cl2, 400 MHz) δ (ppm) 7.63 (d, 2H), 7.01-7.30 (m, 8H), 6.35-6.62 (m, 6H); $^{13}$C NMR (CD2CL2, 100 MHz) δ (ppm) 142.0, 141.6, 140.6, 134.2, 132.7, 129,4, 128.3, 126.2, 125.6, 124.6, 123.7, 123.4, 121.3, 120.7, 118.7, 117.5, 109.4.

(2) Synthesis of Compound 7

Compound 7 (yield 68%) was synthesized using the same method as that used in the synthesis of Compound 1, except that Intermediate C was used instead of 4-bromophenyl-diphenyl amine.

Intermediate D (yield 45%) was synthesized using the method similar to that used in the synthesis of Intermediate C.

$^1$H NMR (CD2Cl2, 400 MHz) δ (ppm) 7.51-7.44 (m, 2H), 7.01-7.23 (m, 8H), 6.35-6.76 (m, 6H); $^{13}$C NMR (CD2CL2, 100 MHz) δ (ppm) 142.6, 141.6, 140.4, 133.5, 132.7, 129.4, 127.8, 126.6, 126.4, 125.0, 124.5, 123.7, 122.9, 121.5, 121.1, 117.5, 117.0, 107.4.

(2) Synthesis of Compound 9

Compound 9 (yield 73%) was synthesized using the same method as that used in the synthesis of Compound 1, except that Intermediate D was used instead of 4-bromophenyl-diphenyl amine.

$^1$H NMR (CD2Cl2, 400 MHz) δ (ppm) 7.76-7.80 (m, 6H), 7.65 (d, 2H), 7.54 (d, 2H), 7.20-7.46 (m, 28H), 7.10 (t, 2H), 2.37 (s, 6H), 2.29 (s, 6H); $^{13}$C NMR (CD2Cl2, 100 MHz) δ (ppm) 147.5, 146.8, 145.1, 136.4, 134.7, 134.4, 133.4, 132.5, 130.3, 129.4, 129.2, 129.1, 128.6, 127.6, 127.0, 126.3, 124.8, 124.7, 124.6, 123.7, 123.5, 121.3, 121.0, 116,5, 109.7, 108.0, 11.1, 8.9.

Synthesis Example 4

Preparation of Compound 18

Compound 18 was synthesized through a reaction pathway illustrated in Reaction Scheme 4 below.

Intermediate E (yield 52%) was synthesized using the method similar to that used in the synthesis of Intermediate C.

$^1$H NMR (CD2Cl2, 400 MHz) δ (ppm) 7.18-7.48 (m, 16H), 6.35-6.52 (m, 6H); $^{13}$C NMR (CD2CL2, 100 MHz) δ (ppm) 140.6, 140.5, 136.6, 132.7, 131.0, 129.0, 128.3, 127.4, 127.2, 123.7, 122.0, 117.5.

(2) Synthesis of Compound 18

Compound 18 (yield 69%) was synthesized using the same method as that used in the synthesis of Compound 1, except that Intermediate E was used instead of 4-bromophenyl-diphenyl amine.

$^1$H NMR (CD2Cl2, 400 MHz) δ (ppm) 7.56-7.80 (m, 8H), 7.42-7.50 (m, 8H), 7.16-7.38 (m, 30H), 7.06-7.10 (m, 4H), 2.39 (s, 6H), 2.30 (s, 6H); $^{13}$C NMR (CD2Cl2, 100 MHz) δ (ppm) 146.5, 145.4, 138.4, 134.2, 133.4, 132.5, 130.3, 129.5, 129.1, 129.0, 128.4, 127.3, 126.3, 124.2, 124.0, 123.2, 121.2, 116,4, 109.3, 108.2, 11.1, 9.0.

Reaction Scheme 4

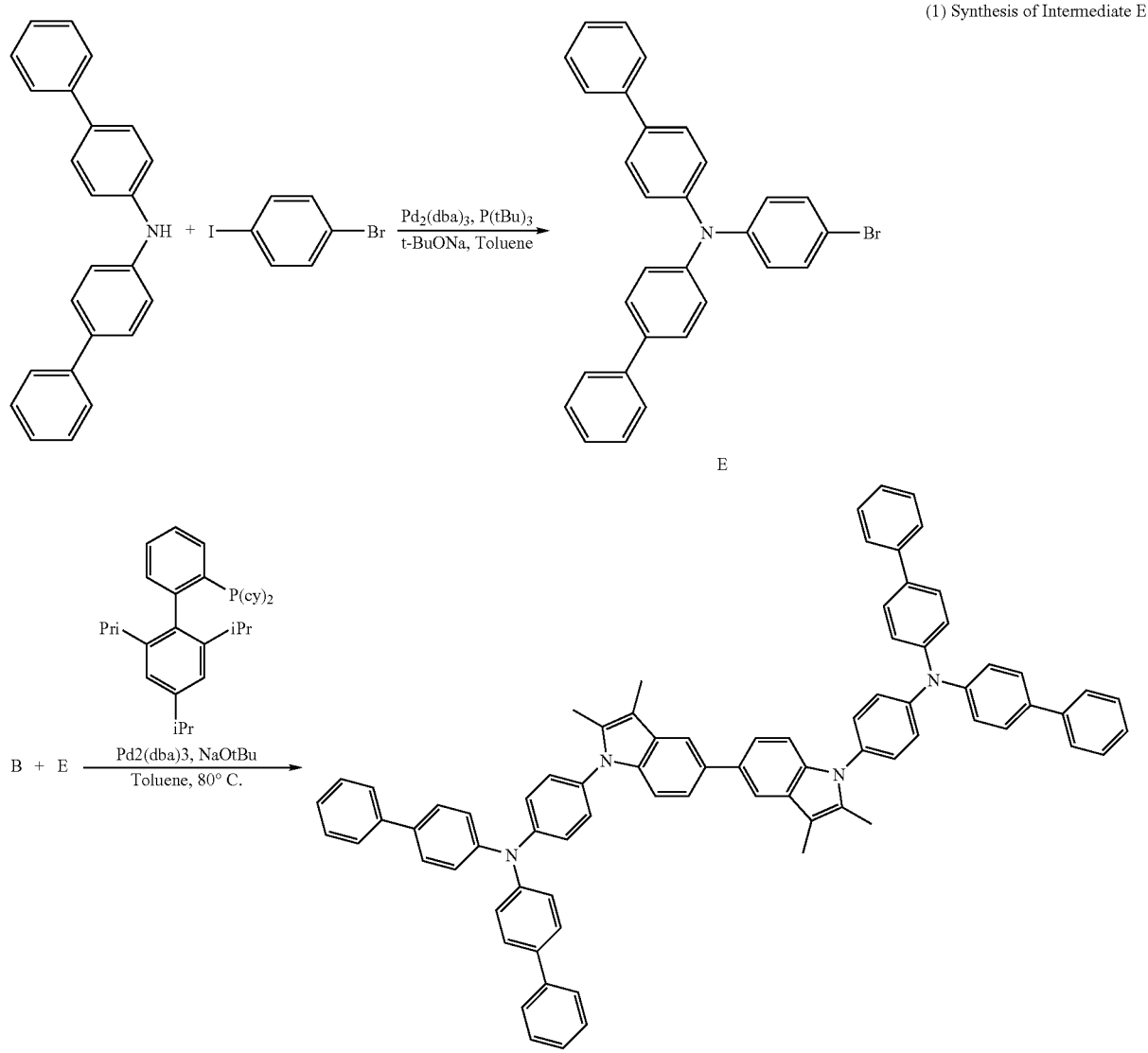

18

Synthesis Example 5
Preparation of Compound 79
Compound 79 was synthesized through a reaction pathway illustrated in Reaction Scheme 5 below.
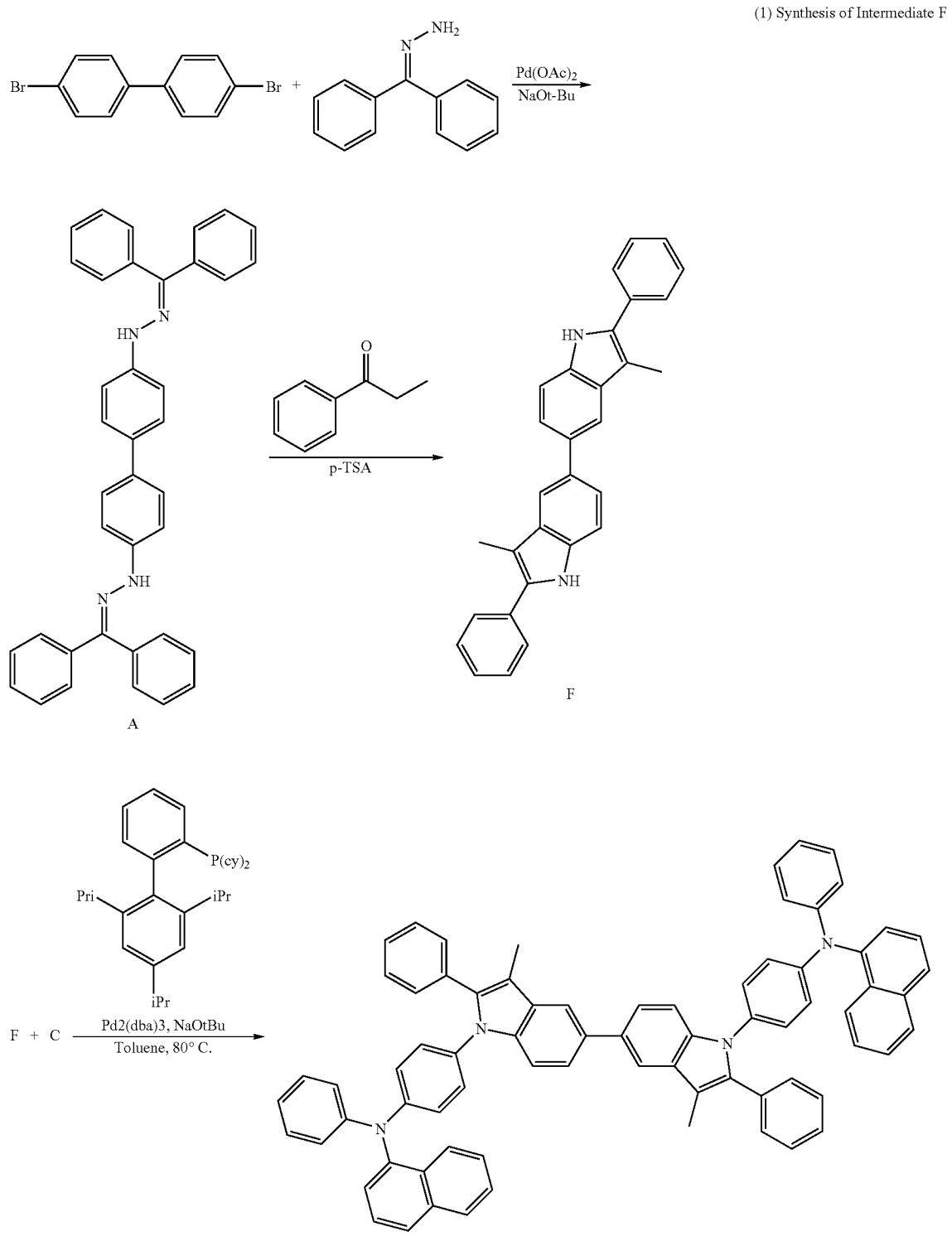
Reaction Scheme 5
(1) Synthesis of Intermediate F 10.8 g of Intermediate A (20.0 mmole), 15.2 g of p-toluenesulfonic acid monohydrate (80.0 mmole), and 6.7 g of phenylethylketone (50.0 mmole) were added to 200 ml of ethanol, and the mixture was stirred while refluxing for 15 hours in a nitrogen atmosphere. After the reaction was terminated, water was added to the reaction solution and the resultant solution was extracted using 150 ml of methylene chloride three times. The collected organic layer was dried over magnesium sulfate and a solvent was evaporated to obtain the residue. The residue was purified by silicagel column chromatography to obtain 1.9 g (yield 67%) of a light brown solid Intermediate B.

$^1$H NMR (DMSO-d6, 400 MHz) δ (ppm) 11.2 (s, 2H), 7.43-7.48 (m, 4H), 7.20-7.40 (m, 12H), 2.30 (s, 6H); $^{13}$C NMR (DMSO-d6, 100 MHz) δ (ppm) 136.5, 135.0, 132.2, 130.4, 129.2, 128.5, 124.3, 123.2, 119.9, 119.5, 112.2, 10.8.

(2) Synthesis of Compound 79

Compound 79 (yield 71%) was synthesized using the same method as that used in the synthesis of Compound 1, except that Intermediate F and Intermediate C were respectively used instead of Intermediate B and 4-bromophenyl-diphenyl amine.

$^1$H NMR (CD2Cl2, 400 MHz) δ (ppm) 7.91-7.95 (m, 6H), 7.81 (d, 2H), 7.47-7.58 (m, 6H), 7.28-7.44 (m, 16H), 7.23 (t, 4H), 6.96-7.10 (m, 14H) 2.48 (s, 6H); $^{13}$C NMR (CD2Cl2, 100 MHz) δ (ppm) 132.2, 132.1, 131.1, 130.7, 129.6, 129.2, 128.6, 128.5, 127.9, 127.3, 127.1, 126.7, 126.5, 126.4, 126.2, 124.1, 122.4, 122.3, 122.2, 121.5, 117.9, 110.5, 9.5.

Example 1

Manufacture of Organic Electroluminescent Device

To produce an anode, a corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resultant glass substrate was mounted on a vacuum deposition device.

Then, 4,4',4"-tris[2-naphthyl(phenyl)amino]triphenylaminere (2-TNATA) represented by the following structure was vacuum-deposited on the glass substrate to form a hole injection layer having a thickness of 600 Å, and then Compound 1 prepared in Synthesis Example 1 as a hole transporting compound was vacuum deposited on the hole injection layer to form a hole transport layer having a thickness of 300 Å.

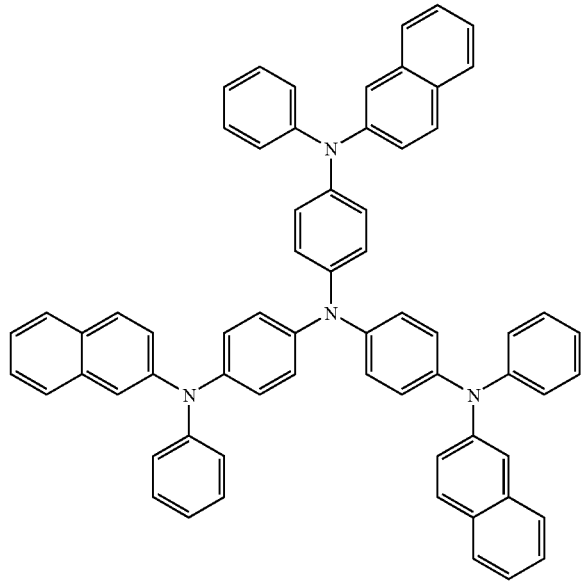

2-TNATA

On the hole transport layer, Alq$_3$ that is a known green fluorescent host and C545T that is a known green fluorescent dopant were simultaneously deposited in a weight ratio of 98:2 to form an emitting layer having a thickness of 300 Å.

Then, Alq$_3$ was deposited on the emitting layer to form an electron transport layer having a thickness of 300 Å, and then LiF that is halogenated alkali metal was deposited on the electron transport layer to form an electron injection layer having a thickness of 10 Å and Al was deposited on the electron injection layer to form a cathode having a thickness of 3000 Å, thereby forming an LiF/Al electrode. As a result, an organic electroluminescent device was completely manufactured.

The organic electroluminescent device had the driving voltage of 7.12 V at the current density of 50 mA/cm$^2$, high luminosity of 7,640 cd/m$^2$, a color coordinate of (0.310, 0.644), and a luminescent efficiency of 15.28 cd/A.

Example 2

Manufacture of Organic Electroluminescent Device

An organic electroluminescent device was manufactured in the same manner as in Example 1, except that the hole injection layer was formed using Compound 7 instead of Compound 1.

The organic electroluminescent device had the driving voltage of 6.98 V at the current density of 50 mA/cm$^2$, high luminosity of 8,891 cd/m$^2$, a color coordinate of (0.310, 0.643), and a luminescent efficiency of 17.78 cd/A.

Example 3

Manufacture of Organic Electroluminescent Device

An organic electroluminescent device was manufactured in the same manner as in Example 1, except that the hole injection layer was formed using Compound 9 instead of Compound 1.

The organic electroluminescent device had the driving voltage of 7.17 V at the current density of 50 mA/cm$^2$, high luminosity of 8,596 cd/m$^2$, a color coordinate of (0.309, 0.642), and a luminescent efficiency of 17.19 cd/A.

Example 4

Manufacture of Organic Electroluminescent Device

An organic electroluminescent device was manufactured in the same manner as in Example 1, except that the hole injection layer was formed using Compound 18 instead of Compound 1.

The organic electroluminescent device had the driving voltage of 7.472 V at the current density of 50 mA/cm$^2$, high luminosity of 7,472 cd/m$^2$, a color coordinate of (0.310, 0.642), and a luminescent efficiency of 14.94 cd/A.

Comparative Example 1

Manufacture of Organic Electroluminescent Device

An organic electroluminescent device was manufactured in the same manner as in Example 1, except that the hole transport layer was formed using known 4,4'-bis[N-(1-naphthyl)-N-phenylamino]biphenyl (NPB) instead of Compound 1.

The organic electroluminescent device had the driving voltage of 7.45 V at the current density of 50 mA/cm$^2$, high luminosity of 6,102 cd/m$^2$, a color coordinate of (0.309, 0.642), and a luminescent efficiency of 12.2 cd/A.

For the organic electroluminescent devices manufactured using the heterocyclic compounds represented by Formula 1 according to the present embodiments, the driving voltage was lower than when NPB was used. In addition, the organic electroluminescent devices manufactured using hetero-cyclic compounds represented by Formula 1 according to the present embodiments had significantly high efficiency and showed excellent I-V-L characteristics. Organic electroluminescent devices manufactured using heterocyclic compounds according to the present embodiments having an excellent hole injecting capability and hole transporting capability had a low driving voltage, a high efficiency, high luminosity, and a long lifetime.

According to the present embodiments, the heterocyclic compound represented by Formula 1 has excellent electrical characteristics and an excellent charge transporting capability, and thus the heterocyclic compound of Formula 1 can be used as a hole injecting material, a hole transporting material, and/or a light emitting material that are suitable for all-color fluorescent and phosphorescent organic light emitting devices such as red, green, blue, and white fluorescent and phosphorescent organic light emitting devices. When the heterocyclic compound of Formula 1 is used to manufacture an organic electroluminescent device, the organic electroluminescent device can have a high efficiency, a low driving voltage, high luminosity, and a long lifetime.

While the present embodiments have been particularly shown and described with reference to exemplary embodiments thereof, it will be understood by those of ordinary skill in the art that various changes in form and details may be made therein without departing from the spirit and scope of the present embodiments as defined by the following claims.

What is claimed is:

1. A heterocyclic compound represented by Formula 1 below:

Formula 1

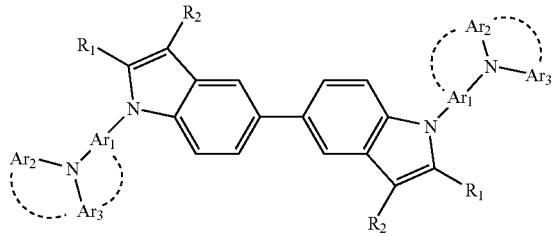

wherein Ar$_2$, and Ar$_3$ are each independently a substituted or unsubstituted C$_6$-C$_{20}$ aryl group, a substituted or unsubstituted C$_4$-C$_{20}$ heterocyclic group, or a substituted or unsubstituted C$_4$-C$_{20}$ condensed polycyclic group, wherein Ar$_1$ is a substituted or unsubstituted C$_6$-C$_{20}$ arylene group, a substituted or unsubstituted C$_4$-C$_{20}$ heterocyclic group, or a substituted or unsubstituted C$_4$-C$_{20}$ condensed polycyclic group, and R$_1$ and R$_2$ are each independently a substituted or unsubstituted C$_1$-C$_{10}$ alkyl group, a substituted or unsubstituted C$_1$-C$_{10}$ alkoxy group, fluorine, a cyano group, an amine group, a substituted or unsubstituted C$_6$-C$_{20}$ aryl group, a substituted or unsubstituted C$_6$-C$_{20}$ aryloxy group, a substituted or unsubstituted C$_4$-C$_{20}$ heterocyclic group, or a substituted or unsubstituted C$_4$-C$_{20}$ condensed polycyclic group.

2. The heterocyclic compound of claim 1, wherein Ar$_2$, and Ar$_3$ are each independently selected from the group consisting of a phenyl group, a naphthyl group, an anthryl group, a phenanthryl group, a pyrenyl group, a biphenyl group, a terphenyl group, a fluorenyl group, a carbazolyl group, and those in which at least one hydrogen thereof is substituted with a substituent selected from the group consisting of a C$_1$-C$_4$ alkyl group, a C$_1$-C$_5$ alkoxy group, a cyano group, an amine group, a phenoxy group, a phenyl group, and a halogen atom.

3. The heterocyclic compound of claim 1, wherein Ar$_2$, and Ar$_3$ are each independently selected from the group consisting of phenyl, methylphenyl, fluorophenyl, cyanophenyl, naphthyl, biphenyl, terphenyl, carbazolyl, fluorenyl, and pyrenyl.

4. The heterocyclic compound of claim 1, wherein R$_1$ and R$_2$ are each independently selected from the group consisting of methyl, phenyl, naphthyl, biphenyl, fluorophenyl, cyanophenyl, and methylphenyl.

5. The heterocyclic compound of claim 1, wherein Ar$_1$ and Ar$_3$ or Ar$_2$ and Ar$_3$ are bound to each other to form a ring.

6. The heterocyclic compound of claim 5, wherein Ar$_1$ and Ar$_3$ or Ar$_2$ and Ar$_3$ are bound to each other to form a carbazolyl group.

7. The heterocyclic compound of claim 1, wherein Formula 1 is selected from the following structural formulae:

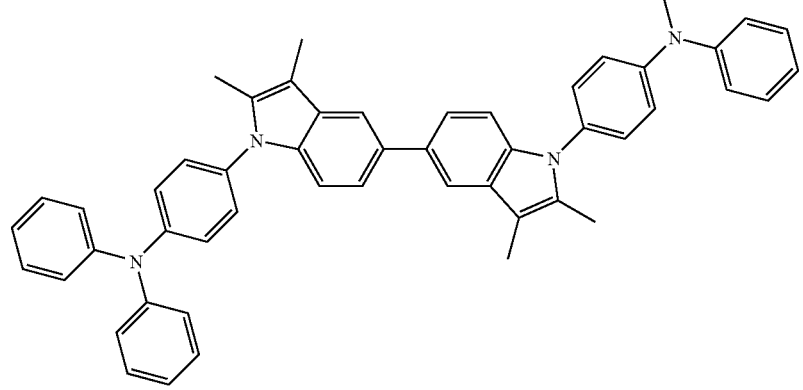

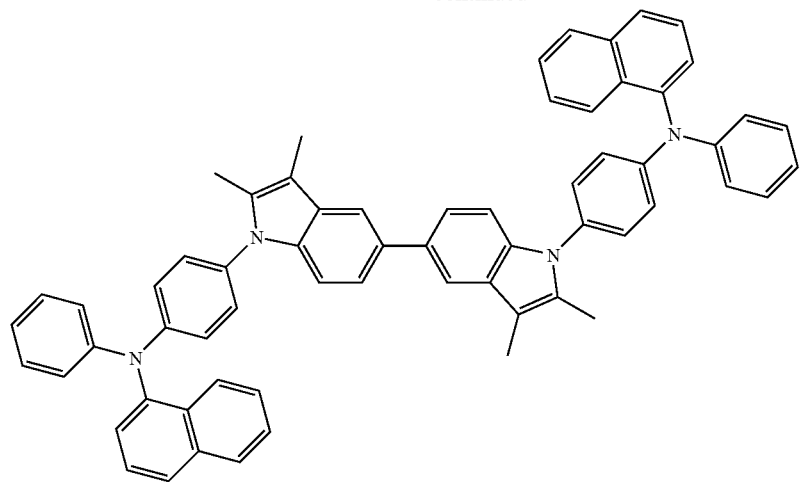
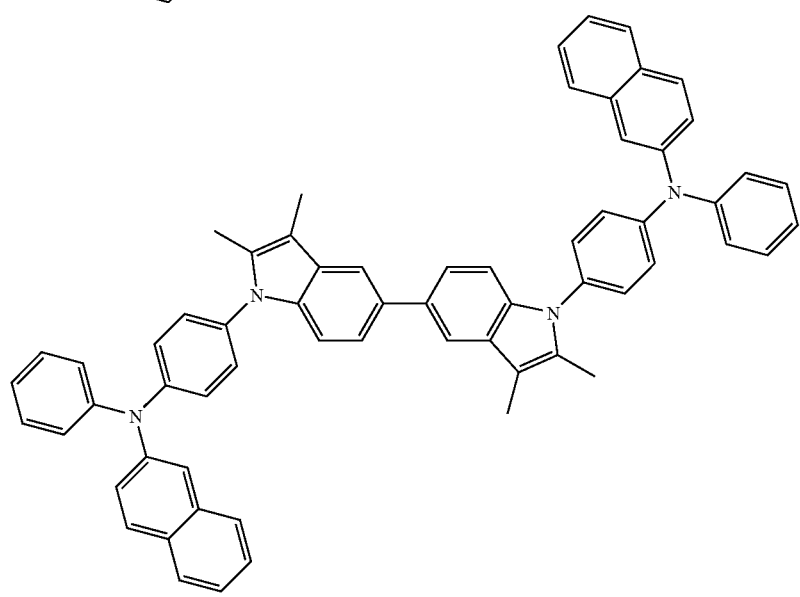
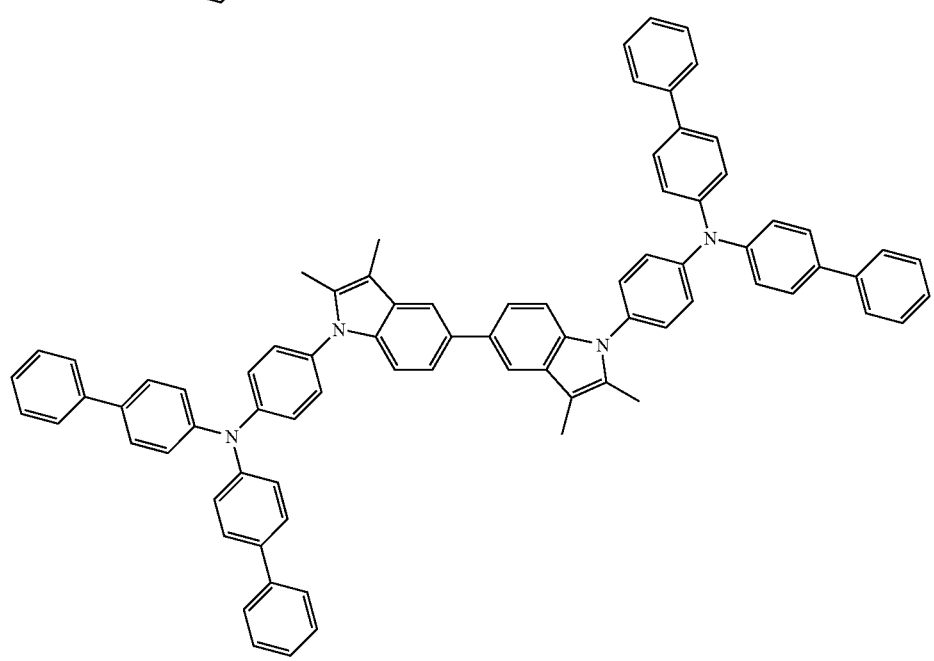

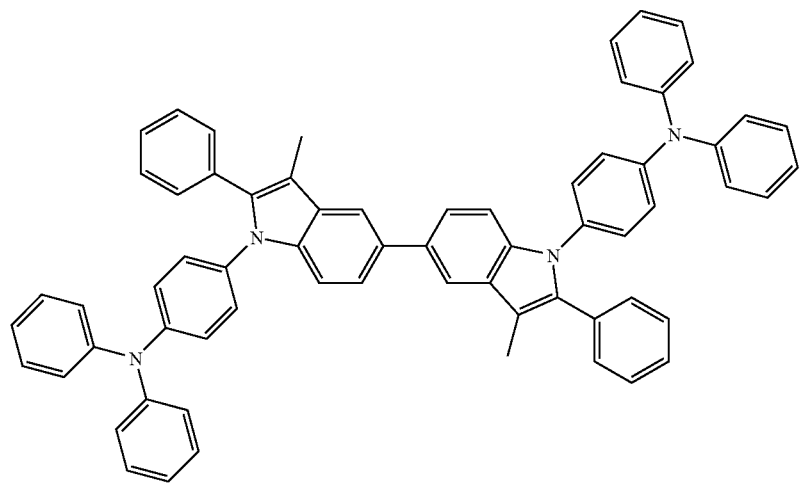
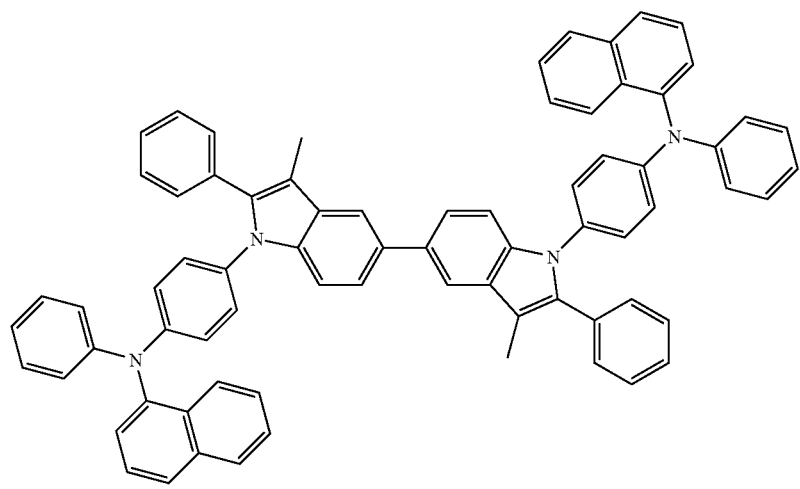
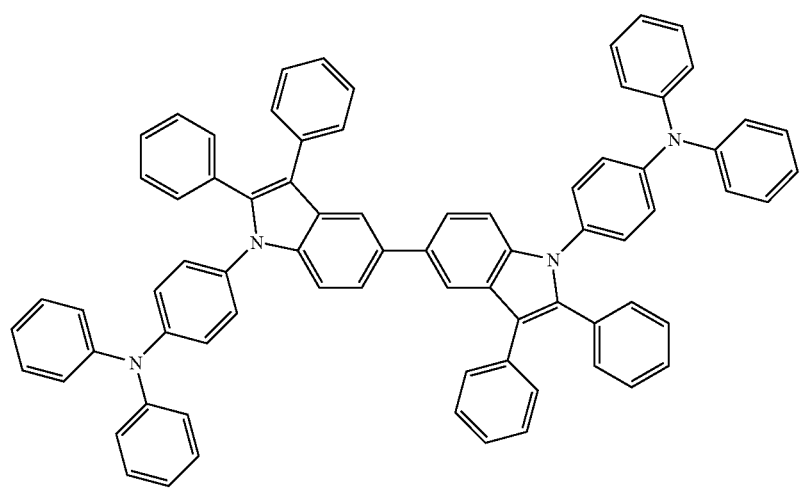

-continued
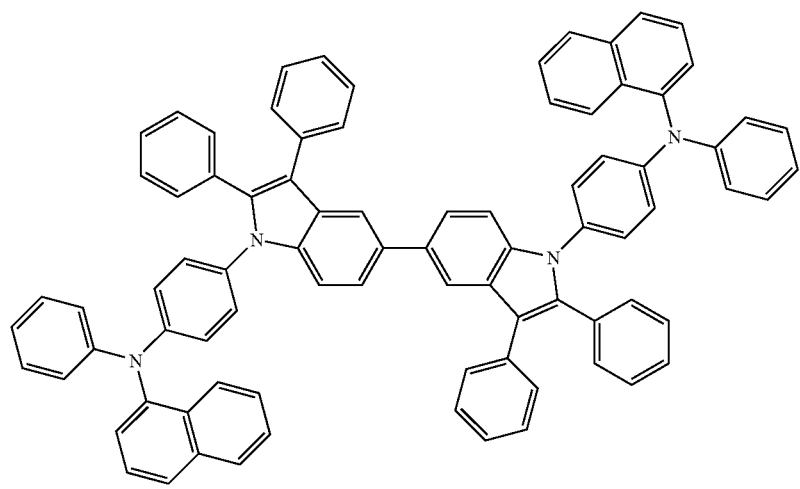
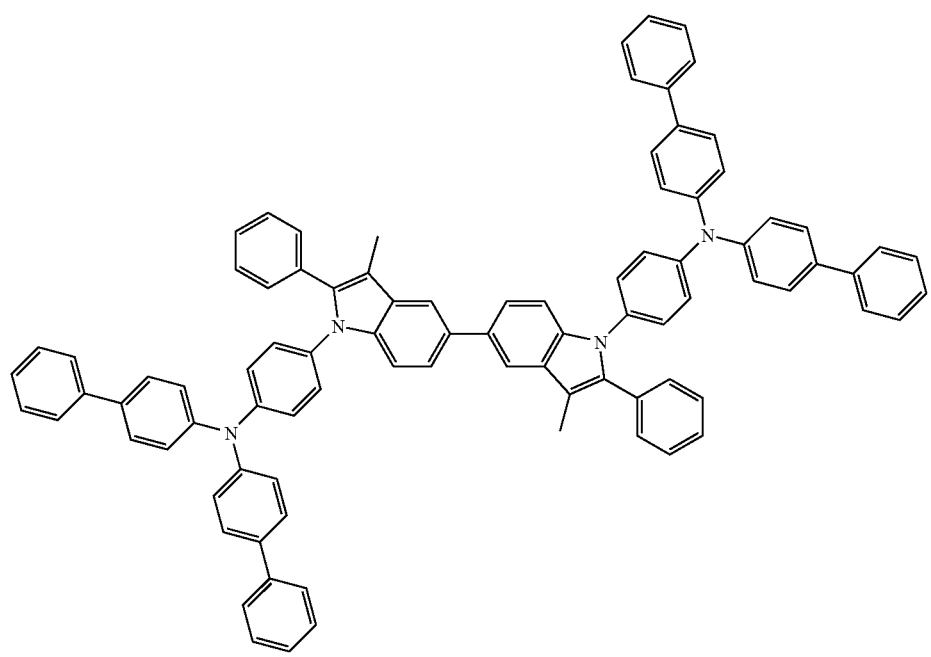

-continued

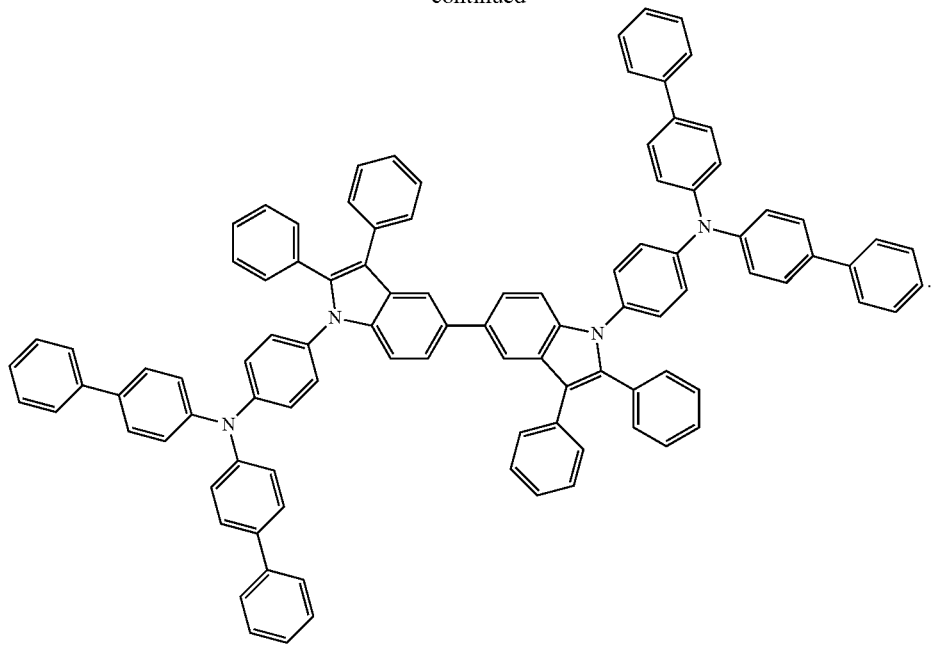

8. An organic electroluminescent device comprising: a first electrode; a second electrode; and an organic layer interposed between the first electrode and the second electrode, wherein the organic layer comprises the heterocyclic compound according to claim 1.

9. The organic electroluminescent device of claim 8, wherein the organic layer comprises a heterocyclic compound represented by Formula 1 below:

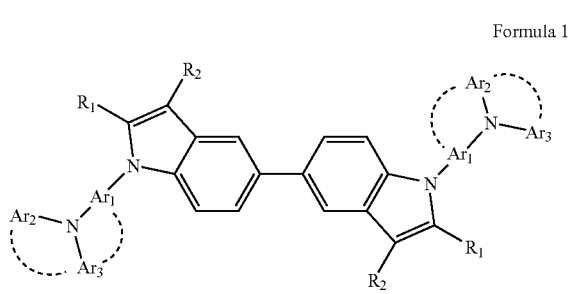

Formula 1 wherein $Ar_1$ is a substituted or unsubstituted $C_6$-$C_{20}$ arylene group, a substituted or unsubstituted $C_4$-$C_{20}$ heterocyclic group, or a substituted or unsubstituted $C_4$-$C_{20}$ condensed polycyclic group, and $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group, wherein $Ar_2$, and $Ar_3$ are each independently selected from the group consisting of a phenyl group, a naphthyl group, an anthryl group, a phenanthryl group, a pyrenyl group, a biphenyl group, a terphenyl group, a fluorenyl group, a carbazolyl group, and those in which at least one hydrogen thereof is substituted with a substituent selected from the group consisting of a $C_1$-$C_4$ alkyl group, a $C_1$-$C_5$ alkoxy group, a cyano group, an amine group, a phenoxy group, a phenyl group, and a halogen atom.

10. The organic electroluminescent device of claim 8, wherein the organic layer comprises a heterocyclic compound represented by Formula 1 below:

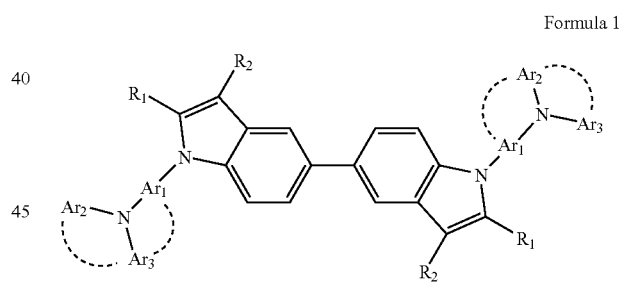

Formula 1 wherein $Ar_1$ is a substituted or unsubstituted $C_6$-$C_{20}$ arylene group, a substituted or unsubstituted $C_4$-$C_{20}$ heterocyclic group, or a substituted or unsubstituted $C_4$-$C_{20}$ condensed polycyclic group, and $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group, wherein $Ar_2$, and $Ar_3$ are each independently selected from the group consisting of phenyl, methylphenyl, fluorophenyl, cyanophenyl, naphthyl, biphenyl, terphenyl, carbazolyl, fluorenyl, and pyrenyl.

11. The organic electroluminescent device of claim 8, wherein the organic layer comprises a heterocyclic compound represented by Formula 1 below:

Formula 1

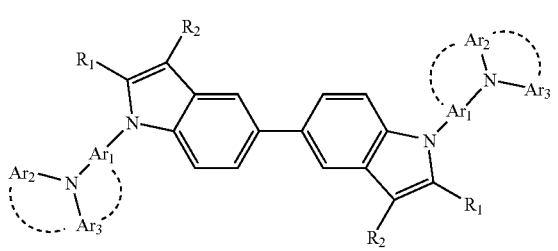

wherein Ar₂, and Ar₃ are each independently a substituted or unsubstituted C₆-C₂₀ aryl group, a substituted or unsubstituted C₄-C₂₀ heterocyclic group, or a substituted or unsubstituted C₄-C₂₀ condensed polycyclic group, wherein Ar₁ is a substituted or unsubstituted C₆-C₂₀ arylene group, a substituted or unsubstituted C₄-C₂₀ heterocyclic group, or a substituted or unsubstituted C₄-C₂₀ condensed polycyclic group, and wherein R₁ and R₂ are each independently selected from the group consisting of methyl, phenyl, naphthyl, biphenyl, fluorophenyl, cyanophenyl, and methylphenyl.

12. The organic electroluminescent device of claim 8, wherein the organic layer comprises a heterocyclic compound represented by Formula 1 below:

Formula 1

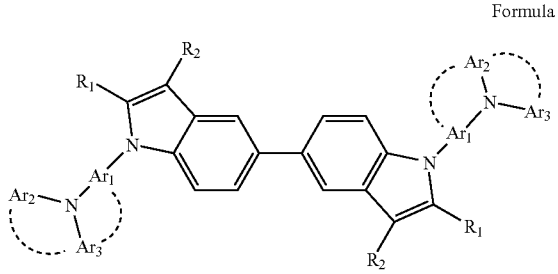

wherein Ar₂, and Ar₃ are each independently a substituted or unsubstituted C₆-C₂₀ aryl group, a substituted or unsubstituted C₄-C₂₀ heterocyclic group, or a substituted or unsubstituted C₄-C₂₀ condensed polycyclic group, wherein Ar₁ is a substituted or unsubstituted C₆-C₂₀ arylene group, a substituted or unsubstituted C₄-C₂₀ heterocyclic group, or a substituted or unsubstituted C₄-C₂₀ condensed polycyclic group, and R₁ and R₂ are each independently a substituted or unsubstituted C₁-C₁₀ alkyl group, a substituted or unsubstituted C₁-C₁₀ alkoxy group, fluorine, a cyano group, an amine group, a substituted or unsubstituted C₆-C₂₀ aryl group, a substituted or unsubstituted C₆-C₂₀ aryloxy group, a substituted or unsubstituted C₄-C₂₀ heterocyclic group, or a substituted or unsubstituted C₄-C₂₀ condensed polycyclic group, wherein Ar₁ and Ar₃ or Ar₂ and Ar₃ are bound to each other to form a ring.

13. The organic electroluminescent device of claim 8, wherein the organic layer comprises a heterocyclic compound represented by Formula 1 below:

Formula 1

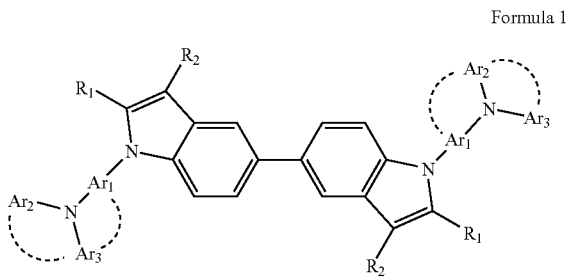

wherein Ar₂, and Ar₃ are each independently a substituted or unsubstituted C₆-C₂₀ aryl group, a substituted or unsubstituted C₄-C₂₀ heterocyclic group, or a substituted or unsubstituted C₄-C₂₀ condensed polycyclic group, wherein Ar₁ is a substituted or unsubstituted C₆-C₂₀ arylene group, a substituted or unsubstituted C₄-C₂₀ heterocyclic group, or a substituted or unsubstituted C₄-C₂₀ condensed polycyclic group, and R₁ and R₂ are each independently a substituted or unsubstituted C₁-C₁₀ alkyl group, a substituted or unsubstituted C₁-C₁₀ alkoxy group, fluorine, a cyano group, an amine group, a substituted or unsubstituted C₆-C₂₀ aryl group, a substituted or unsubstituted C₆-C₂₀ aryloxy group, a substituted or unsubstituted C₄-C₂₀ heterocyclic group, or a substituted or unsubstituted C₄-C₂₀ condensed polycyclic group, wherein Ar₁ and Ar₃ or Ar₂ and Ar₃ are bound to each other to form a carbazolyl group.

14. The organic electroluminescent device of claim 8, wherein the organic layer comprises a heterocyclic compound represented by one selected from the following structural formulae:

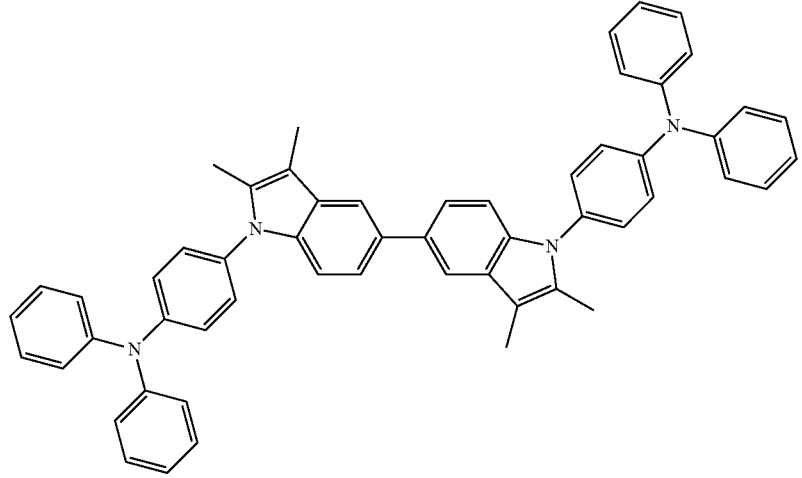

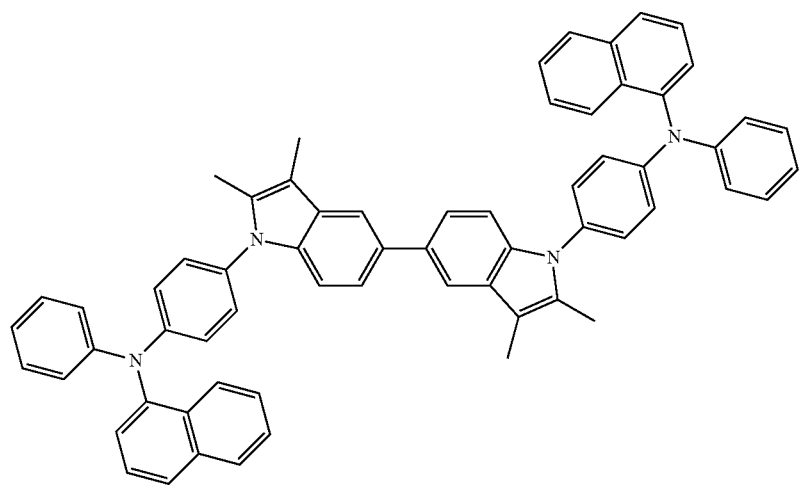
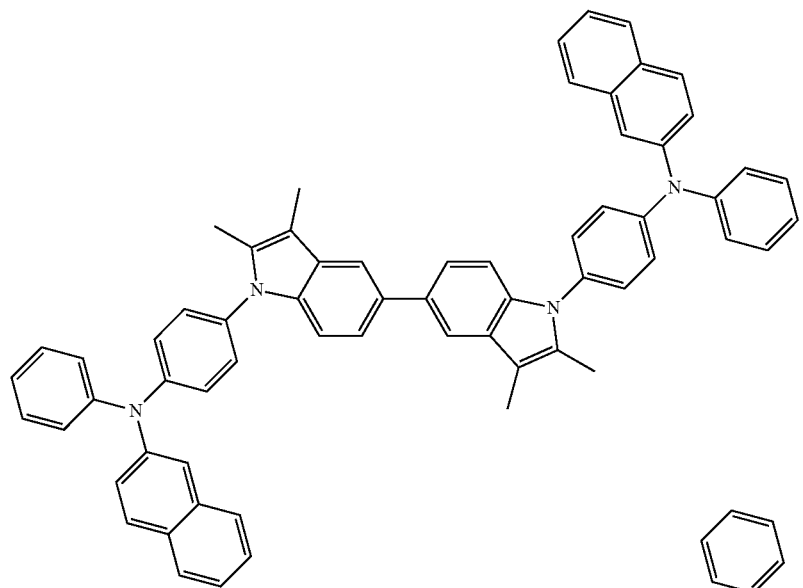
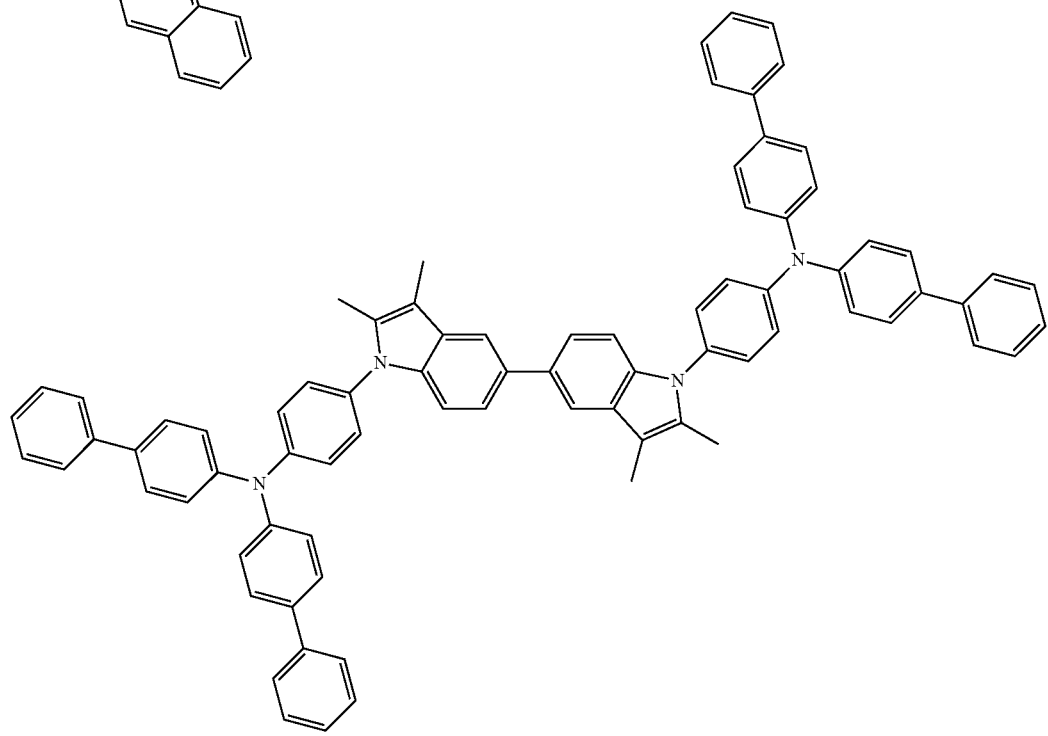

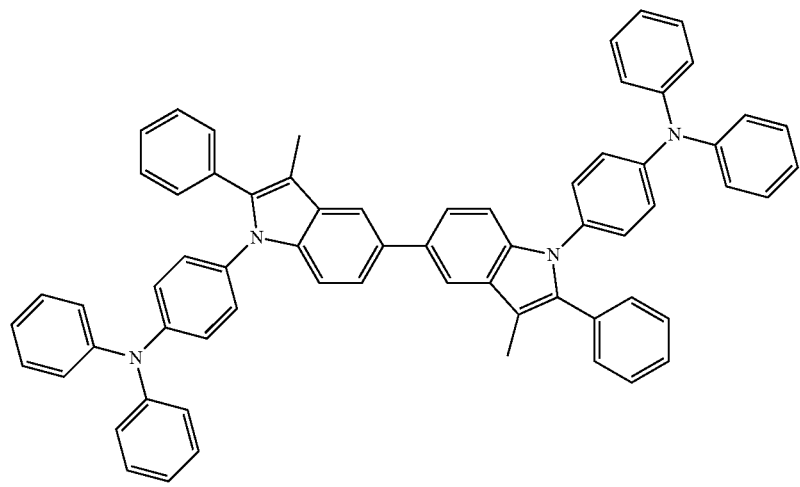
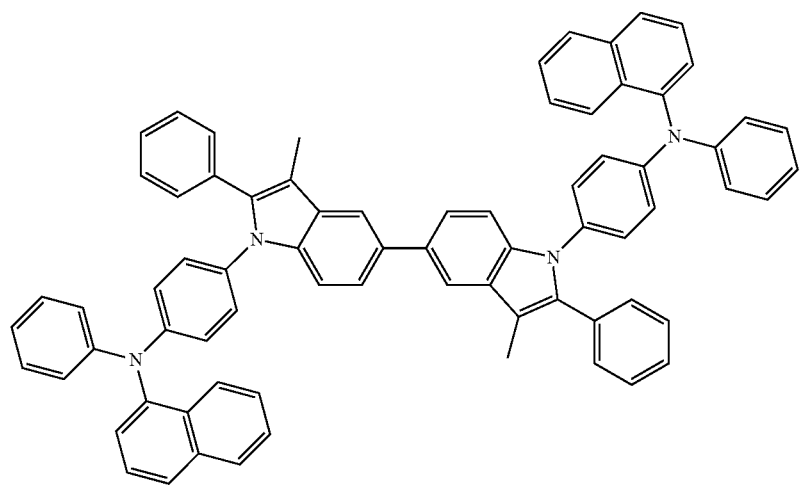
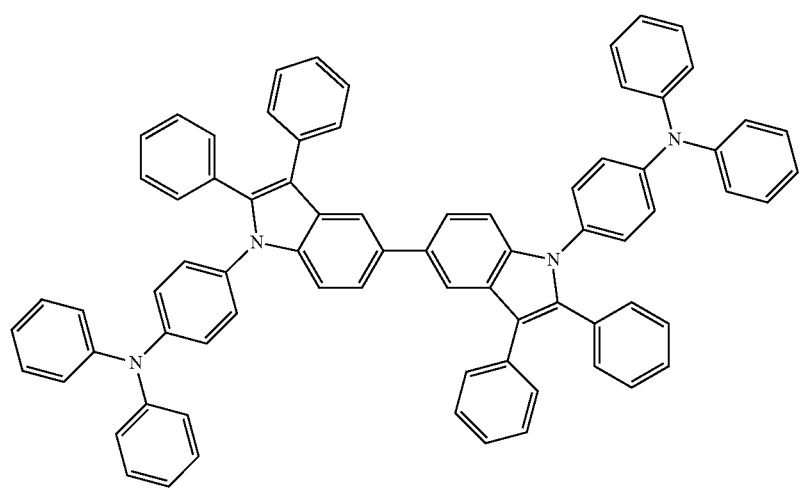

-continued
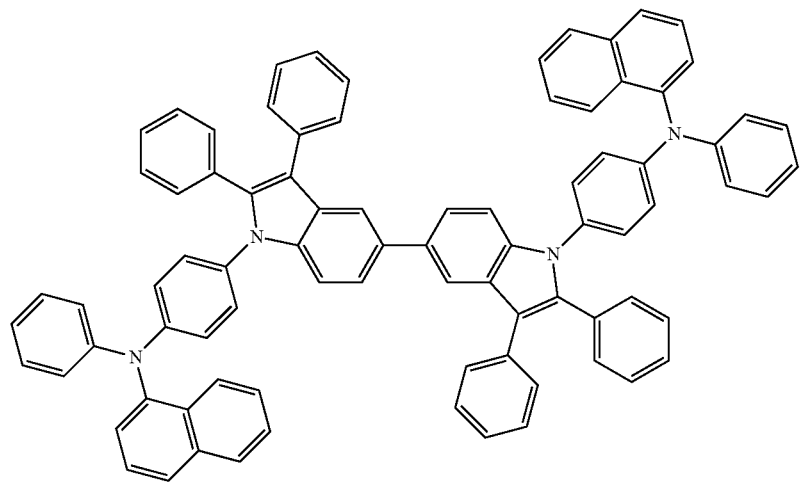
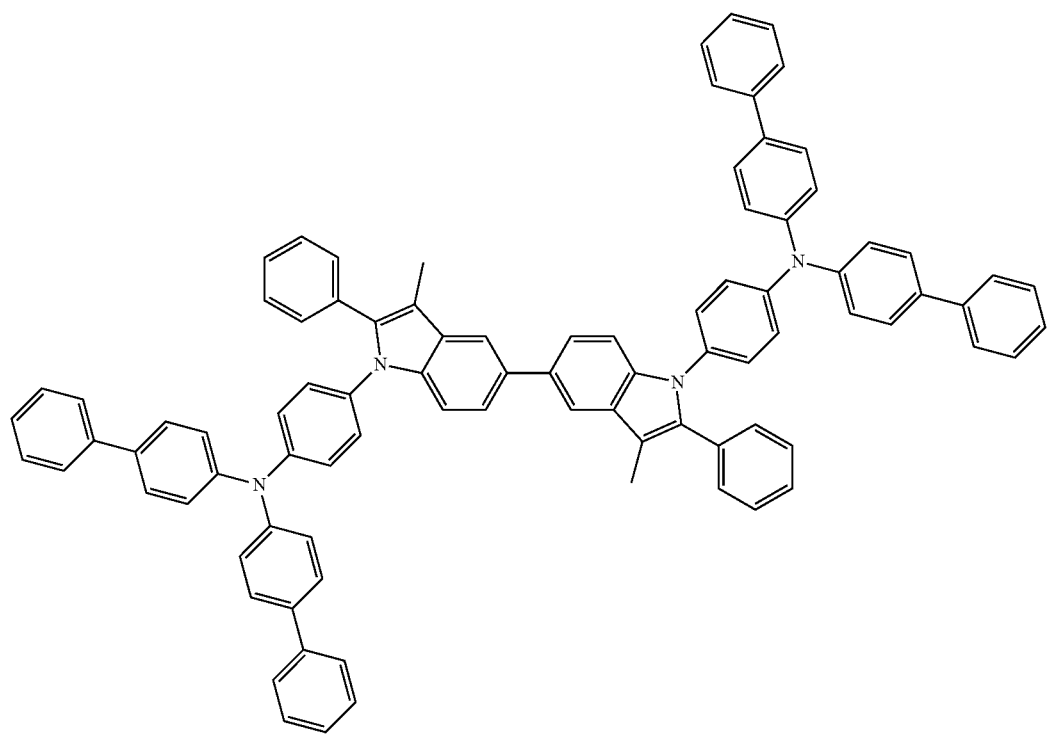

-continued

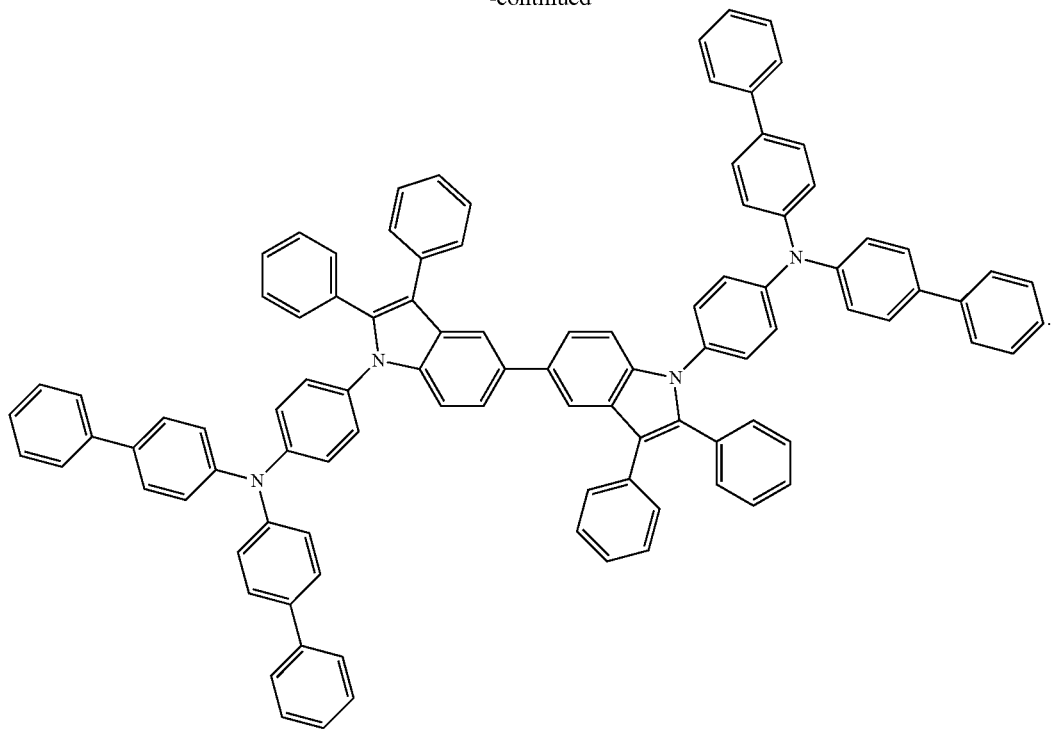

15. The organic electroluminescent device of claim 8, wherein the organic layer is a hole injection layer or a hole transport layer.

16. The organic electroluminescent device of claim 8, wherein the organic layer is an emitting layer.

17. The organic electroluminescent device of claim 16, wherein, in the emitting layer, the heterocyclic compound represented by Formula 1 is used as a fluorescent or phosphorescent host.

18. A flat panel display device comprising the organic electroluminescent device according to claim 8, wherein the first electrode of the organic electroluminescent device is electrically connected to a source electrode or drain electrode of a thin film transistor.

19. The flat panel display device of claim 18, comprising an organic electroluminescent device comprising a first electrode; a second electrode; and an organic layer interposed between the first electrode and the second electrode, wherein the organic layer comprises a heterocyclic compound represented by Formula 1 below:

Formula 1

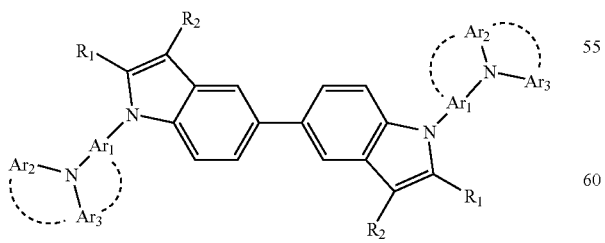

wherein $Ar_2$, and $Ar_3$ are each independently a substituted or unsubstituted $C_6$-$C_{20}$ aryl group, a substituted or unsubstituted $C_4$-$C_{20}$ heterocyclic group, or a substituted or unsubstituted $C_4$-$C_{20}$ condensed polycyclic group, wherein $Ar_1$ is a substituted or unsubstituted $C_6$-$C_{20}$ arylene group, a substituted or unsubstituted $C_4$-$C_{20}$ heterocyclic group, or a substituted or unsubstituted $C_4$-$C_{20}$ condensed polycyclic group, and $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group wherein the organic layer is a hole injection layer or a hole transport layer.

20. The flat panel display device of claim 18, comprising an organic electroluminescent device comprising a first electrode; a second electrode; and an organic layer interposed between the first electrode and the second electrode, wherein the organic layer comprises a heterocyclic compound represented by Formula 1 below:

Formula 1

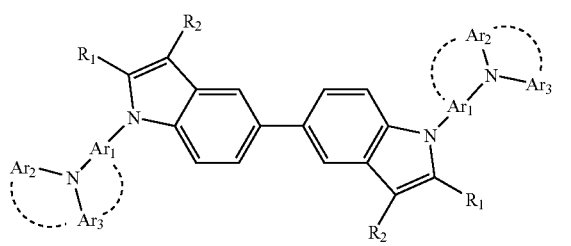

wherein $Ar_2$, and $Ar_3$ are each independently a substituted or unsubstituted $C_6$-$C_{20}$ aryl group, a substituted or unsubstituted $C_4$-$C_{20}$ heterocyclic group, or a substituted or unsubstituted $C_4$-$C_{20}$ condensed polycyclic group, wherein $Ar_1$ is a substituted or unsubstituted $C_6$-$C_{20}$ arylene group, a substituted or unsubstituted $C_4$-$C_{20}$ heterocyclic group, or a substituted or unsubstituted $C_4$-$C_{20}$ condensed polycyclic group, and $R_1$ and $R_2$ are each independently a substituted or unsubstituted $C_1$-$C_{10}$ alkyl group, a substituted or unsubstituted $C_1$-$C_{10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group wherein the organic layer is an emitting layer.

21. The flat panel display device of claim 18, comprising an organic electroluminescent device comprising a first electrode; a second electrode; and an organic layer interposed between the first electrode and the second electrode, wherein the organic layer comprises a heterocyclic compound represented by Formula 1 below:

Formula 1

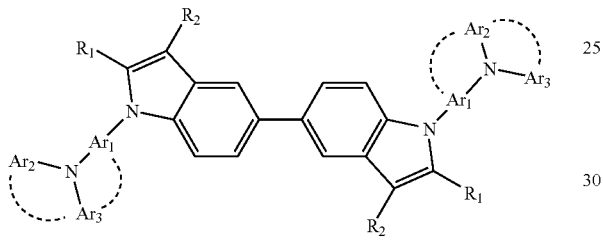

wherein $Ar_2$, and $Ar_3$ are each independently a substituted or unsubstituted $C_6$-$C_{20}$ aryl group, a substituted or unsubstituted $C_4$-$C_{20}$ heterocyclic group, or a substituted or unsubstituted $C_4$-$C_{20}$ condensed polycyclic group, wherein $Ar_1$ is a substituted or unsubstituted $C_6$-$C_{20}$ arylene group, a substituted or unsubstituted $C_4$-$C_{20}$ heterocyclic group, or a substituted or unsubstituted $C_4$-$C_{20}$ condensed polycyclic group, and $R_1$ and $R_2$ are each independently a substituted or unsubstituted $C_1$-$C_{10}$ alkyl group, a substituted or unsubstituted $C_{1-10}$ alkoxy group, fluorine, a cyano group, an amine group, a substituted or unsubstituted $C_6$-$C_{20}$ aryl group, a substituted or unsubstituted $C_6$-$C_{20}$ aryloxy group, a substituted or unsubstituted $C_4$-$C_{20}$ heterocyclic group, or a substituted or unsubstituted $C_4$-$C_{20}$ condensed polycyclic group wherein the organic layer is an emitting layer and, in the emitting layer, the heterocyclic compound represented by Formula 1 is used as a fluorescent or phosphorescent host.

* * * * *